US012590283B2

(12) United States Patent
Rashedi et al.

(10) Patent No.: US 12,590,283 B2
(45) Date of Patent: Mar. 31, 2026

(54) HYBRID PREDICTIVE MODELING FOR CONTROL OF CELL CULTURE

(71) Applicant: AMGEN INC., Thousand Oaks, CA (US)

(72) Inventors: Mohammad Rashedi, Edmonton (CA); Hamid Khodabandehlou, Thousand Oaks, CA (US); Seyedehmina Rafieishishavan, Windsor (CA); Matthew N. Demers, Glocester, RI (US); Aditya Tulsyan, Atlanta, GA (US); Tony Y. Wang, Tiverton, RI (US)

(73) Assignee: AMGEN INC., Thousand Oaks, CA (US)

( * ) Notice: Subject to any disclaimer, the term of this patent is extended or adjusted under 35 U.S.C. 154(b) by 431 days.

(21) Appl. No.: 18/113,967

(22) Filed: Feb. 24, 2023

(65) Prior Publication Data

US 2023/0279332 A1      Sep. 7, 2023

Related U.S. Application Data

(60) Provisional application No. 63/315,358, filed on Mar. 1, 2022.

(51) Int. Cl.
*C12M 1/36*          (2006.01)
*C12M 1/34*          (2006.01)

(52) U.S. Cl.
CPC ............ *C12M 41/48* (2013.01); *C12M 41/32* (2013.01)

(58) Field of Classification Search
CPC ...... C12M 41/48; C12M 41/32; C12M 29/00; C12M 41/46; C12M 41/44; G01N 21/65;
(Continued)

(56) References Cited

U.S. PATENT DOCUMENTS

2017/0355947 A9    12/2017    Berry et al.
2020/0377844 A1    12/2020    Paul et al.

FOREIGN PATENT DOCUMENTS

CA            3094078 A1 *  9/2019  ......... G01N 15/1429
WO    WO-2020086635 A1 *  4/2020  ........... C12M 41/48

OTHER PUBLICATIONS

Boudreau et al., New Directions in Bioprocess Modeling and Control: Maximizing Process Analytical Technology Benefits, ISA, Research Triangle Park, NC (2006).
(Continued)

*Primary Examiner* — Charles R Kasenge
(74) *Attorney, Agent, or Firm* — MARSHALL, GERSTEIN & BORUN LLP

(57)                ABSTRACT

A method of controlling a cell culture process uses hybrid predictive modeling in a model predictive controller. The method includes, for multiple time intervals, obtaining current values of cell culture attributes associated, and generating a control value for a physical input to the cell culture process. Generating the control value includes predicting future values of the cell culture attributes based on the current values, by using one or more data-driven models to predict future values of a first one or more attributes of the cell culture attributes, and using one or more first principle models to predict future values of a second one or more attributes of the cell culture attributes. Generating the control value also includes determining the control value by optimizing an objective function subject to the predicted future values. The method also includes using the control value to control the physical input to the cell culture process.

22 Claims, 43 Drawing Sheets

(58) Field of Classification Search
    CPC ........ G06N 3/0464; G06N 3/084; G06N 3/09;
                G06N 20/10; G01J 3/28; G01J 3/44
    See application file for complete search history.

(56)                  References Cited

OTHER PUBLICATIONS

Catlin et al., A roadmap for a digital transformation, McKinsey &
Company, 11 pages, Mar. 2017.
Chtourou et al., Control of a bioreactor using a neural network,
Bioprocess Engineering, 8:251-4 (1993).
Craven et al., Glucose concentration control of a fed-batch mam-
malian cell bioprocess using a nonlinear model predictive control-
ler, Journal of Process Control, 24:344-57 (2014).
Craven et al., Process model comparison and transferability across
bioreactor scales and modes of operation for a mammalian cell
bioprocess, Biotechnol. Prog., 29(1):186-96 (2013).
Jose et al., Developmental studies of an adaptive on-line softsensor
for biological wastewater treatments, Can. J. Chem. Eng., 77:707-
17 (1999).
Kiran et al., Control of continuous fed-batch fermentation process
using neural network based model predictive controller, Bioprocess
Biosyst. Eng., 32:801-8 (2009).
Patnaik, An integrated hybrid neural system for noise filtering,
simulation and control of a fed-batch recombinant fermentation,
Biochemical Engineering Journal, 15:165-75 (2003).
Qin et al., A survey of industrial model predictive control technol-
ogy, Control Engineering Practice, 11:733-64 (2003).
Sen et al., A hybrid MPC-PID control system design for the
continuous purification and processing of active pharmaceutical
ingredients, Processes, 2:392-418 (2014).
Sinclair et al., Fermentation Kinetics and Modelling, Open Univer-
sity Press, Milton Keynes, 44, xi-113 (1987).
Tulsyan et al., Advances in industrial biopharmaceutical batch
process monitoring: Machine-learning methods for small data prob-
lems, Biotechnology and Bioengineering, 115:1915-24 (2018).
Tulsyan et al., Spectroscopic models for real-time monitoring of cell
culture processes using spatiotemporal just-in-time Gaussian pro-
cesses, AICHE J., 67:317210 (2021).
Whitby et al., PID Control of Biochemical Reaction Networks,
IEEE Transactions on Automatic Control, vol. 67, Issue 2, 8 pages
(Feb. 2021).
Rio-Chanona et al., Comparison of physics-based and data-driven
modelling techniques for dynamic optimisation of fed-batch
bioprocesses, Biotechnology and Bioengineering, 116:2971-82 (2019).
Whelan et al., In situ Rama spectroscopy for simultaneous moni-
toring of multiple process parameters in mammalian cell culture
bioreactors, Biotechnology Progress, 28(5):1355-62 (2012).
International Application No. PCT/US2023/013763, International
Search Report and Written Opinion, mailed Jun. 19, 2023.

* cited by examiner

400

2500

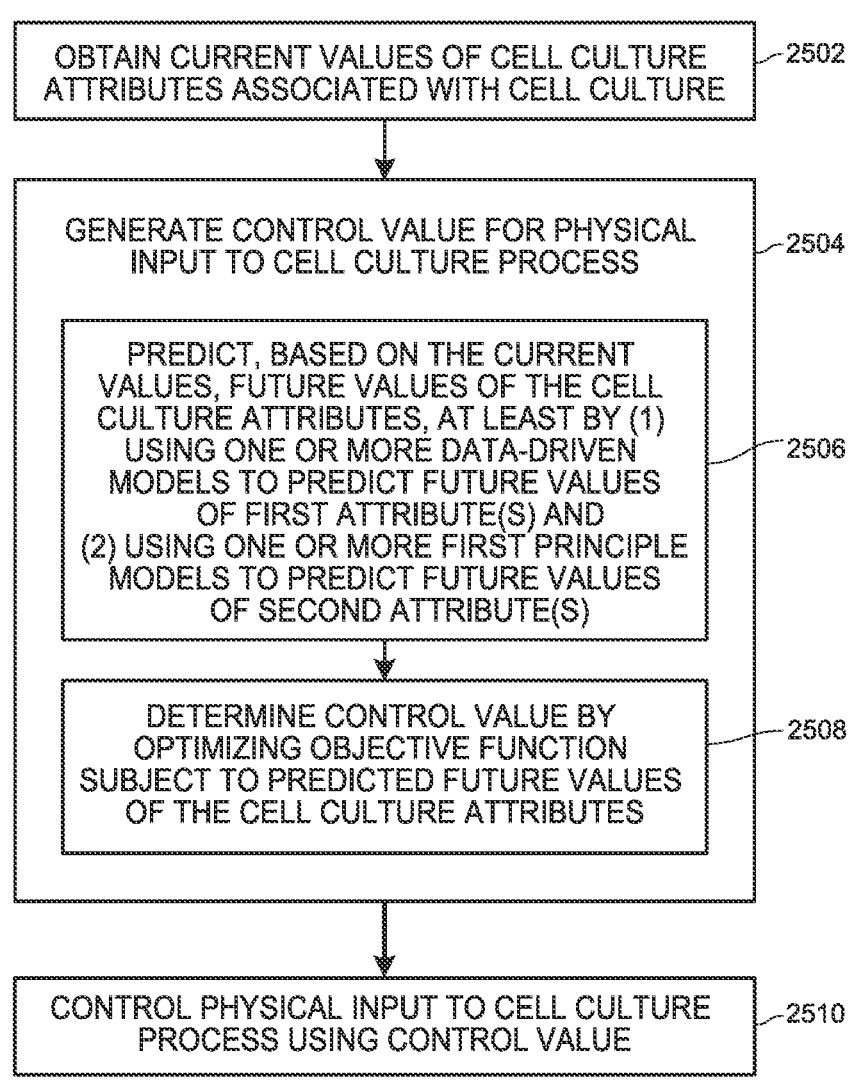

OBTAIN CURRENT VALUES OF CELL CULTURE ATTRIBUTES ASSOCIATED WITH CELL CULTURE ~2502

GENERATE CONTROL VALUE FOR PHYSICAL INPUT TO CELL CULTURE PROCESS ~2504

PREDICT, BASED ON THE CURRENT VALUES, FUTURE VALUES OF THE CELL CULTURE ATTRIBUTES, AT LEAST BY (1) USING ONE OR MORE DATA-DRIVEN MODELS TO PREDICT FUTURE VALUES OF FIRST ATTRIBUTE(S) AND (2) USING ONE OR MORE FIRST PRINCIPLE MODELS TO PREDICT FUTURE VALUES OF SECOND ATTRIBUTE(S) ~2506

DETERMINE CONTROL VALUE BY OPTIMIZING OBJECTIVE FUNCTION SUBJECT TO PREDICTED FUTURE VALUES OF THE CELL CULTURE ATTRIBUTES ~2508

CONTROL PHYSICAL INPUT TO CELL CULTURE PROCESS USING CONTROL VALUE ~2510

FIG. 25

HYBRID PREDICTIVE MODELING FOR CONTROL OF CELL CULTURE

CROSS-REFERENCE TO RELATED APPLICATIONS

The present application claims the benefit of U.S. Provisional Patent Application No. 63/315,358, filed on Mar. 1, 2022 and entitled "Hybrid Predictive Modeling for Control of Cell Culture", the entire disclosure of which is hereby incorporated herein by reference.

FIELD OF THE DISCLOSURE

The present application relates generally to cell cultures (e.g., in a bioreactor), and more specifically to the prediction and control of cell culture attributes.

BACKGROUND

The biopharmaceutical industry continuously strives to improve productivity while ensuring the process remains reliable and cost-effective. With the advent of capabilities such as new digital technologies, higher computational power, better integration flexibility, and artificial intelligence, new avenues have emerged to meet these objectives. One of these is by harnessing process data to improve the way the process is controlled. Recently, many smart factories have attempted to manage various process scenarios and process automation using adaptive models without human intervention. See Catlin et al., A Roadmap for a Digital Transformation, 2017, McKinsey. To achieve this successfully, advanced control of the processes in real-time is necessary.

Due to a variety of challenges such as scarcity of measurements and process complexities, the control of biopharmaceutical processes has in practice rarely evolved beyond simple PID (Proportional-Integral-Derivative) control of small sets of variables. See Whitby et al., PID Control of Biochemical Reaction Networks, 2019, 2019 IEEE 58<sup>th</sup> Conference on Decision and Control (CDC), 8372-8379; Sen et al., A Hybrid MPC-PID Control System Design for the Continuous Purification and Processing of Active Pharmaceutical Ingredients, 2014, Processes, 2, 392-418. In such processes, the traditional method of control aims to manipulate the extracellular environment to control the intracellular reactions of the culture. See Boudreau et al., New Directions in Bioprocess Modeling and Control: Maximizing Process Analytical Technology Benefits, 2006, ISA, Research Triangle Park, NC. Model predictive control (MPC) is an advanced multi-step control method that is not only efficient in multivariate process control, but can also address the constraints imposed by both the manipulated variables (inputs) and the controlled variables (outputs). See S. J. Qin, A Survey of Industrial Model Predictive Control Technology, 2003, Control Engineering Practice, 11, 733-764. The main component of the MPC is the dynamical model of the process which is used to determine the optimal control action, leading to an optimized and feasible objective ahead of time.

In the literature, there are a variety of first-principle and data-driven models for bioprocesses. See Craven et. al., Process Model Comparison and Transferability Across Bioreactor Scales and Modes of Operation for a Mammalian Cell Bioprocess, 2013, AICHE Journal, 29, 186-196; Tulsyan et al., Advances in Industrial Biopharmaceutical Batch Process Monitoring: Machine-Learning Methods for Small Data Problems, 2018, Biotechnol Bioeng, 115, 1915-1924. The first-principle models are mostly obtained based on Monod kinetics and enzymatic schemes which bring about nonlinear state models with many unknown free parameters. See Craven et al., Glucose Concentration Control of a Fed-Batch Mammalian Cell Bioprocess Using a Nonlinear Model Predictive Controller, 2014, Journal of Process Control, 24, 344-357. On the other hand, the use of data-driven methods for the purpose of process monitoring and control has been intensively studied. See Kiran et al., Control of Continuous Fed-Batch Fermentation Process Using Neural Network Based Model Predictive Controller, 2009, Bioprocess Biosyst Eng, 32, 801-808; Tulsyan et al., Spectroscopic Models for Real-Time Monitoring of Cell Culture Processes Using Spatiotemporal Just-in-Time Gaussian Processes, 2021, AICHE Journal, 67, e17210. The choice of model is important as it affects the computational load as well as the accuracy and reliability of the control policy. Neural network models have been used in many works for the purpose of controller design in fed-batch fermentation processes. See Chtourou et al., Control of a Bioreactor Using a Neural Network, 1993, Bioprocess Eng., 8, 251-254; Patnaik, An Integrated Hybrid Neural System for Noise Filtering, Simulation and Control of a Fed-Batch Recombinant Fermentation, 2003, Biochem Eng J., 15, 165-175. Unfortunately, due to the time-varying characteristics of the fed-batch fermentation and limited amount of training data, the models typically do not have high accuracy.

As stated above, models such as Monod kinetics may result in a large number of unknown parameters. However, the discrete feed stream in fed-batch processes may cause insensitivity of the target variables to the feed strategy. Furthermore, the complex multilevel reactions in the process, quick adaptability of cells in the process (see Sinclair et al., Fermentation Kinetics and Modelling, 1987, Open University Press, Milton Keynes, 44, xi-113), and random variability that occurs during a batch operation may also decrease the accuracy of these simplified models. See Jose et al., Developmental Studies of an Adaptive On-Line Softsensor for Biological Wastewater Treatments, 1999, Can. J. Chem. Eng., 77, 707-717.

BRIEF SUMMARY

Bioprocesses can often be characterized by their nonlinearity, variability, and complexity that arise due to metabolic network pathways inside the cells. Once there is an acceptable understanding of the process, sophisticated advanced control strategies can be employed to increase the reliability and efficiency of the process. Model predictive control (MPC) uses a real-time process model to make predictions, by optimizing an objective (cost) function at each time interval while preserving custom constraints. By predicting upcoming disturbances and guaranteeing prediction stability, MPC results in prescriptive control actions. In the MPC framework, the prediction of the process under consideration computes control actions based on future outcomes as it relates to the model objectives and constraints, and the future behavior of the dynamic model is based on the prediction model. Hence, the prediction model plays a crucial role in MPC.

Systems and methods described herein generally provide a hybrid approach to prediction in an MPC system by using both first-principles and data-driven modeling. For example, the systems and methods may use data-driven models (e.g., a linear regressor and/or neural network) trained on historical data from real-world cell culture processes to predict future values of certain metabolite concentrations and/or other cell culture attributes (e.g., viable cell density (VCD), osmolality, etc.), while also using a first principle (e.g., mass balance) model to predict future values of glucose concentration, with the latter predictions being based on feed rate as well as data-driven model predictions (e.g., VCD predictions). Use of the first principle model mitigates shortcomings of data-driven models when predicting glucose concentration (e.g., poor sensitivity of the model to the feed), while use of the data-driven model mitigates the inability of first principle models (for example, current mass balance models) to accurately and consistently model relationships between glucose and other metabolites.

As a whole, the hybrid model can more accurately and consistently predict future cell culture attributes for the predictive stage of a MPC over a desired prediction horizon. An optimization stage of the MPC can then calculate control values (e.g., glucose feed rate values) over a control horizon by solving an optimization problem for an objective function subject to certain constraints (e.g., minimum and maximum feed rates). At any given time interval, the first control value determined by the MPC (i.e., the value for the earliest time interval of the control horizon) is used to control a physical input to the cell culture process (e.g., a glucose feed rate provided by a glucose pump), and the prediction and optimization stages repeat/update for each time interval (e.g., each day, or each hour, etc.).

The techniques disclosed herein may obviate the need for manual adjusting of control set-points. Moreover, by mitigating shortcomings of both data-driven and first-principles models, these techniques may provide improved prediction accuracy relative to other modeling techniques, thereby allowing for control actions that lead to better performance of the cell culture process (e.g., superior product quality attributes).

BRIEF DESCRIPTION OF THE DRAWINGS

The skilled artisan will understand that the figures described herein are included for purposes of illustration and are not limiting on the present disclosure. The drawings are not necessarily to scale, emphasis instead being placed upon illustrating the principles of the present disclosure. It is to be understood that, in some instances, various aspects of the described implementations may be shown exaggerated or enlarged to facilitate an understanding of the described implementations. In the drawings, like reference characters throughout the various drawings generally refer to functionally similar and/or structurally similar components.

FIG. 25 is a flow diagram of an example method of controlling a cell culture process using hybrid predictive modeling in a model predictive controller.

DETAILED DESCRIPTION

The various concepts introduced above and discussed in greater detail below may be implemented in any of numerous ways, and the described concepts are not limited to any particular manner of implementation. Examples of implementations are provided for illustrative purposes.

Figure 1:
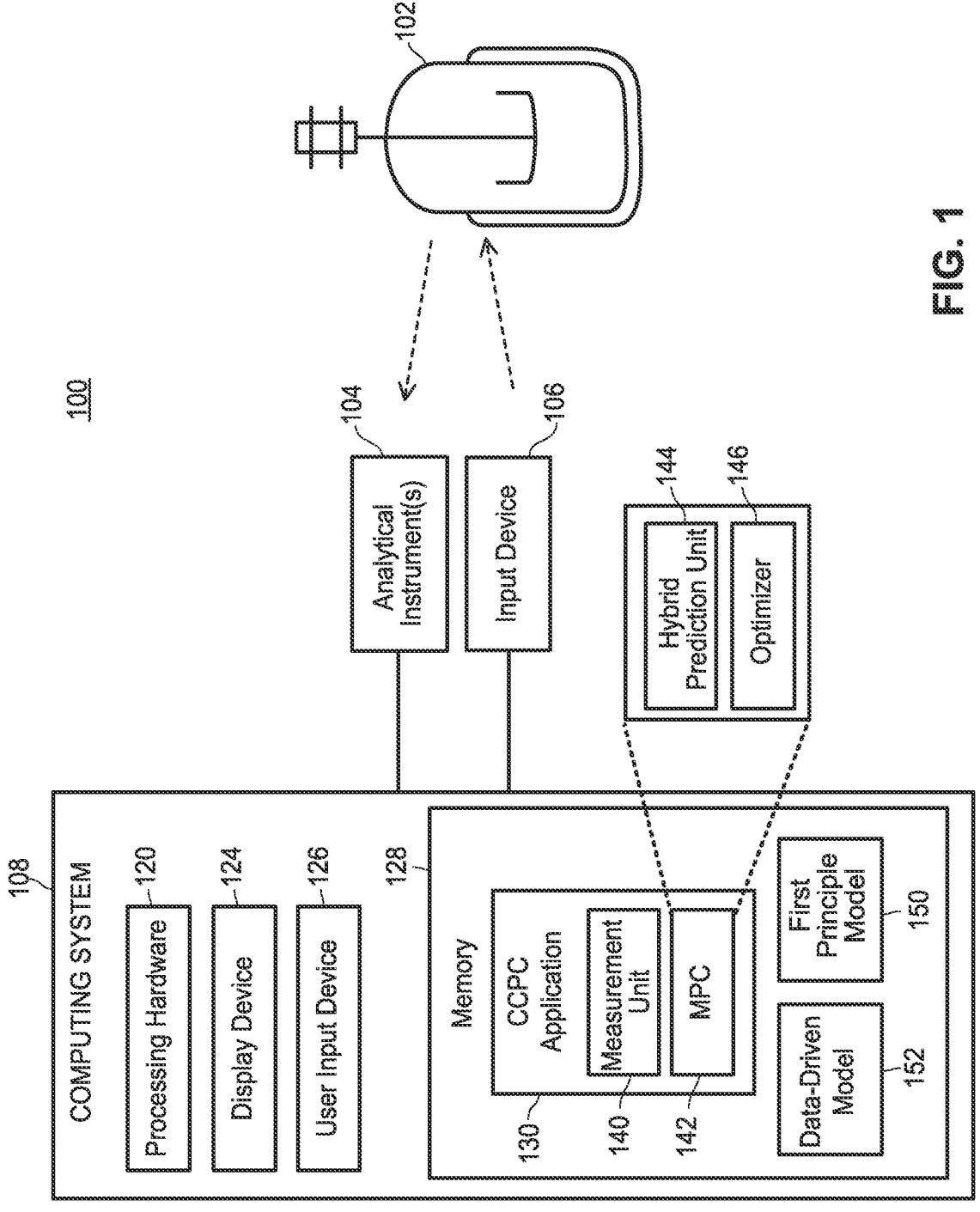
FIG. 1 is a simplified block diagram of an example system that may be used to monitor and control a cell culture process according to the techniques disclosed herein.

FIG. 1 is a simplified block diagram of an example system 100 that may be used to manually monitor and control a cell culture process. The system 100 includes a bioreactor 102, one or more analytical instruments 104, an input device 106, and a computing system 108.

The bioreactor 102 may be any suitable vessel, device, or system that supports a cell culture, which may include living organisms and/or substances derived therefrom within a media. The bioreactor 102 may contain recombinant proteins that are being expressed by the cell culture, e.g., such as for research purposes, clinical use, commercial sale, or other distribution. Depending on the biopharmaceutical process being monitored, the media may include a particular fluid (e.g., a "broth") and specific nutrients, and may have a target pH level or range, a target temperature or temperature range, and so on.

The analytical instrument(s) 104 are communicatively coupled to the computing system 108, and may include any in-line, at-line, and/or off-line instrument, or instruments, configured to measure one or more attributes of the cell culture within the bioreactor 102. For example, the analytical instrument(s) 104 may measure one or more media component concentrations, such as metabolite concentrations (e.g., glucose, lactate, sodium, potassium, glutamine, ammonium, etc.). Additionally or alternatively, the analytical instrument(s) 104 may measure osmolality, packed cell volume (PCV), viable cell density (VCD), total cell density (TCD), viability, and/or one or more other cell culture attributes (e.g., biomass) associated with the contents of the bioreactor 102.

While in some embodiments the analytical instrument(s) 104 may use destructive measurement/analysis techniques, in other embodiments one, some, or all of the analytical instrument(s) 104 use non-destructive measurement/analysis techniques based on optical or imaging technologies. For example, the analytical instrument(s) 104 may include a Raman analyzer with a spectrograph and one or more probes or Near-Infrared (NIR) spectroscopy. The Raman analyzer may include a laser light source that delivers the laser light to the probe(s) via respective fiber optic cables, and may also include a charge-coupled device (CCD) or other suitable camera/recording device to record signals that are received from probe(s) via other channels of the respective fiber optic cables. Alternatively, the laser light source(s) may be integrated within the probe(s). Each probe may be an immersion probe or any other suitable type of probe (e.g., a reflectance probe or transmission probe). The analyzer and probe(s) may non-destructively scan for the relevant cell culture attribute within the bioreactor 102 by exciting, observing, and recording a molecular "fingerprint" of the cell culture process. The molecular fingerprint corresponds to the vibrational, rotational and/or other low-frequency modes of molecules within the biologically active contents when those contents are excited by the laser light delivered by the probe(s). As a result of this scanning process, the Raman analyzer generates one or more Raman scan vectors that each represent intensity as a function of Raman shift (frequency). The Raman analyzer may then analyze the Raman scan vector(s) in order to determine (e.g., infer) values of corresponding cell culture attributes (e.g., glucose and/or other metabolite concentrations).

The Raman spectra approach discussed above may be considered a type of "soft" sensing. In other soft sensing embodiments, one, some, or all of the analytical instrument(s) 104 may include computing/processing devices utilizing one or more models, with the model(s) combining different types of analytical data to predict one or more results based on correlations among those types of analytical data. Such results may be directly or indirectly related to the model inputs (i.e., the analytical data). Alternatively, the computing system 108 itself, or another computing system or device, may perform some or all of this processing for one or more of the analytical instrument(s) 104.

The input device 106 is communicatively coupled to the computing system 108, and may be (or include) any electronically-controllable actuator(s) or component(s) that provide a physical input to the contents of the bioreactor 102. For example, the input device 106 may be a distributed control system (DCS) that includes, or is coupled to, an actuator that provides a direct physical input to the bioreactor 102. As a more specific example, the input device 106 may include a glucose pump that adds a controlled amount or rate of glucose feed to the bioreactor, or a device that provides heat and/or cooling to the bioreactor 102 and its contents, etc. Generally, the input device 106 may include a pump, valve actuator, and/or any other suitable type of control element or combination of control elements. The input device 106 may include a Proportional-Integral-Derivative (PID) controller, and receive set-points from the computing system 108 as inputs to the PID controller, for example. In some embodiments, the system 100 includes two or more electronically-controllable input devices that are controlled by the computing system 108.

The computing system 108 may be a server, a desktop computer, a laptop computer, a tablet device, or any other suitable type of computing device or devices. In the example embodiment shown in FIG. 1, the computing system 108 includes processing hardware 120, a display device 124, a user input device 126, and memory 128. In some embodiments, however, the computing system 108 includes two or more computers that are co-located or remote from each other, or some combination thereof. In these distributed embodiments, the operations described herein relating to the processing hardware 120 and/or the memory 128 may be divided among multiple processing units and/or memories, respectively.

The processing hardware 120 includes one or more processors, each of which may be a programmable microprocessor that executes software instructions stored in the memory 128 to execute some or all of the functions of the computing system 108 as described herein. Alternatively, some of the processors in the processing hardware 120 may be other types of processors (e.g., application-specific integrated circuits (ASICs), field-programmable gate arrays (FPGAs), etc.), and some of the functionality of the computing system 108 as described herein may instead be implemented, in part or in whole, by such hardware. The memory 128 may include one or more physical memory devices or units containing volatile and/or non-volatile memory. Any suitable memory type or types may be used, such as read-only memory (ROM), solid-state drives (SSDs), hard disk drives (HDDs), and so on.

The display device 124 may use any suitable display technology (e.g., LED, OLED, LCD, etc.) to present information to a user, and the user input device 126 may be a keyboard, mouse, trackpad, graphics/drawing tablet, or other suitable input device. In some embodiments, the display device 124 and the user input device 126 are integrated within a single device (e.g., a touchscreen display). Generally, the display device 124 and the user input device 126 may jointly enable a user to interact with graphical user interfaces (GUIs) provided by the computing system 108, e.g., for purposes such as monitoring the cell culture process occurring within the bioreactor 102. In some embodiments, however, the computing system 108 does not include the display device 124 and/or the user input device 126.

The memory 128 stores the instructions of one or more software applications, including a cell culture process control (CCPC) application 130. The CCPC application 130, when executed by the processing hardware 120, is generally configured to communicate with the analytical instrument(s) 104 and the input device 106 to obtain measured values of cell culture attributes and control one or more inputs to the cell culture process, respectively. The time intervals may be any suitable length of time (e.g., once per day, once per hour, etc.). Moreover, the time intervals may be of fixed or variable length/duration (e.g., having a set/predetermined length, or instead having a length that depends on manual and/or variable inputs). Furthermore, regardless of whether the time intervals are fixed/predetermined, the time intervals may: (1) all be of the same length/duration; or (2) include two or more different lengths/durations (e.g., with a first time interval lasting one hour, a second time interval lasting three hours, etc.). To this end, the CCPC application 130 includes a measurement unit 140 and a model predictive controller (MPC) 142. It is understood that the various units of the CCPC application 130 may be distributed among different software applications, and/or that the functionality of any one such unit may be divided among different software applications.

The measurement unit 140 may obtain (e.g., request, or otherwise monitor) the measurements produced by the analytical instrument(s) 104 once per time interval for any desired number of time intervals. In some embodiments, the measurement unit 140 determines one or more cell culture attribute values by processing values obtained from the analytical instrument(s) 104. For example, the measurement unit 140 may determine an average metabolite concentration once per time interval (e.g., once per day) based on metabolite measurements provided on a more frequent basis (e.g., once every 15 minutes, once per hour, etc.) by one of the analytical instrument(s) 104. As another example, the measurement unit 140 may analyze Raman scan vectors provided by a spectrograph of analytical instrument(s) 104 to determine or infer the values of one or more cell culture attributes (as discussed above). Generally, for ease of explanation, terms such as "measured" and "measurement" are broadly used herein to refer to a physically/directly measured value, a soft-sensed value, or a value derived from (e.g., calculated using) a physically/directly measured or soft-sensed value, unless the context of their use clearly indicates a more specific meaning.

The MPC 142 may apply the cell culture attribute values obtained by the measurement unit 140 as inputs to a hybrid prediction unit 144, which predicts future cell culture attribute values for a prediction horizon (e.g., a predetermined number of days or other time intervals). Based on these predicted values, an optimizer 146 of the MPC 142 determines control values for each time interval (e.g., each day) of a control horizon, which is generally some number of time intervals greater than or equal to one, but not greater than the prediction horizon. Specifically, the optimizer 146 determines the control values for each time interval of the control horizon by optimizing (e.g., minimizing) an objective function, subject to various constraints (e.g., maintaining the variables between minimum and maximum values) and the predicted attribute values provided by the hybrid prediction unit 144. At each time interval, in some embodiments, the CCPC application 130 uses the first control value within the control horizon (i.e., the control value corresponding to the current time interval) to control the input device 106, by generating a control signal and sending the control signal to the input device 106. For example, the control signal may conform to a particular protocol understood by the input device 106, and may include the control value in an appropriate field of a protocol message. If the input device 106 is a glucose pump, for example, the CCPC application 130 may generate a control message that specifies a particular glucose feed rate set-point in a certain field of the message.

The hybrid prediction unit 144 utilizes at least two models to generate its predictions. For example, the hybrid prediction unit 144 can utilize a first principle model 150 that was developed based on an understanding of first principles for the cell culture process, and a data-driven model 152 that was trained offline using suitable historical data. In this example, the hybrid prediction unit 144 uses the first principle model 150 to predict values of one or more cell culture attributes for which first-principles modeling has been found to perform better (e.g., be more accurate) than data-driven approaches, and uses the data-driven model 152 to predict values of one or more cell culture attributes for which data-driven (machine learning) models have been found to perform better (e.g., be more accurate) than first-principles models. In some embodiments, for example, the data-driven model 152 predicts future concentrations of certain metabolite concentrations and/or other cell culture attributes over the prediction horizon using past measurements (e.g., past, measured metabolite concentrations as measured by the analytical instrument(s) 104), and the first principle model 150 predicts future glucose concentrations based on past measurements, the known glucose feed rate, and one or more outputs from the data-driven model 152.

The first principle model 150 may model a single phenomenon, or may be a collection of multiple first principle models that model multiple phenomena in the cell culture process, depending on the embodiment. The data-driven model 152 may be a linear model, such as a linear regressor, or a nonlinear model, such as a feed-forward neural network. In some embodiments, the data-driven model 152 comprises two or more data-driven models. For example, the data-driven model 152 may include a different data-driven model to predict values for each of multiple cell culture attributes, with each such model being trained on historical data of the appropriate type. Moreover, the data-driven model 152 may include two or more different types of models to make predictions. For example, the data-driven model 152 may include linear regressors for predicting future values for each of a first set of metabolite concentrations, and include feed-forward neural networks for predicting future values for each of a second set of metabolite concentrations and/or other cell culture attributes (e.g., osmolality, etc.). For ease of explanation, the following description refers primarily to a single first principle model and a single data-driven model. It is understood, however, that the principles discussed below can be extended to the use of multiple first principle models and/or multiple data-driven models.

In some embodiments, the data-driven model 152 predicts values of a cell culture attribute based on past (measured) values of that attribute, as well as one or more known (past or current) control values. For example, the data-driven model 152 may predict a current sodium concentration based only on past, measured sodium concentrations and known glucose feed rates. Additionally, in some embodiments, the data-driven model 152 may predict the values of a cell culture attribute based on past (measured) values of other cell culture attributes. For example, the data-driven model 152 may predict a current sodium concentration based on past, measured concentrations of multiple metabolites (e.g., sodium, glucose, lactate, etc.) and known glucose feed rates.

The data-driven model 152 may be of any suitable order (e.g., second-order, third-order, etc.), where the term "order" as used herein refers to the maximum number of different time intervals reflected in the measurements that are used as the model inputs when forming a prediction of one or more future time interval values. Thus, for example, a regression model that operates on current day and previous day measured metabolite concentrations would be referred to as a second-order regression model, while a regression model that operates on metabolite concentrations from the current day, the previous day, and the day before the previous day would be referred to as a third-order regression model. More generally, a second-order model would, for at least one cell culture attribute used as a model input, operate on measurements obtained at time intervals i and (i–x), and a third-order regression model would, for at least one cell culture attribute used as a model input, operate on measurements obtained at time intervals i, (i–x), and (i–y), where x is any integer greater than zero and y is any integer greater than x. The model may be linear or nonlinear, depending on the embodiment.

Because third-order regression models require measurements from two earlier time intervals (e.g., the two preceding days), it may not be possible to use such a model for the first two time intervals (e.g., Day 0 and Day 1). In some embodiments, therefore, the hybrid prediction unit 144 of FIG. 1 uses a second-order regression model initially (e.g., starting at the second time interval), and then switches to a third-order regression model thereafter (e.g., starting at the third time interval). In other embodiments, the hybrid prediction unit 144 uses other techniques for the initial time interval(s) (e.g., at the first time interval, simply setting two "previous measurement" values equal to the current measurement value).

Arrangements of the system 100, other than that shown in FIG. 1, are also possible. In some embodiments, for example, the system 100 includes a server (not shown in FIG. 1) that trains and/or updates the data-driven model 152, and/or a server that implements the hybrid prediction unit 144 (and possibly also the optimizer 146) and exchanges data with the computing system 108 as part of a web services model. As another example, the system 100 may include one or more additional electronically-controllable input devices, similar to input device 106 but possibly of a different type, and the CCPC application 130 includes multiple MPCs (each similar to the MPC 142, and that each are responsible for controlling a different one of the input devices), i.e., a MIMO (Multi-Input Multi-Output) MPC. For example, the MPC 142 may control a glucose pump, while a second MPC of the CCPC application 130 (or a separate, similar application stored in the memory 128 or another memory) may control the speed of an impeller. For ease of explanation, however, the description that follows focuses primarily on embodiments with a single MPC 142 and a single input device 106.

In some embodiments, the CCPC application 130 also arranges for the presentation (to a user) of information such as the measured values (e.g., values obtained by the measurement unit 140) and/or the future values output by the hybrid prediction unit 144 (e.g., to enable concurrent manual monitoring/oversight of the cell culture process). For example, the CCPC application 130 may generate and/or populate a graph showing past, current, and predicted/future values of cell culture attributes, and cause the display device 124 to display the graph. Alternatively or additionally, the CCPC application 130 may cause the display device 124 to show the values in a table format, and/or in some other suitable format. In still other embodiments, the CCPC application 130 does not display any information to users.

Figure 2:
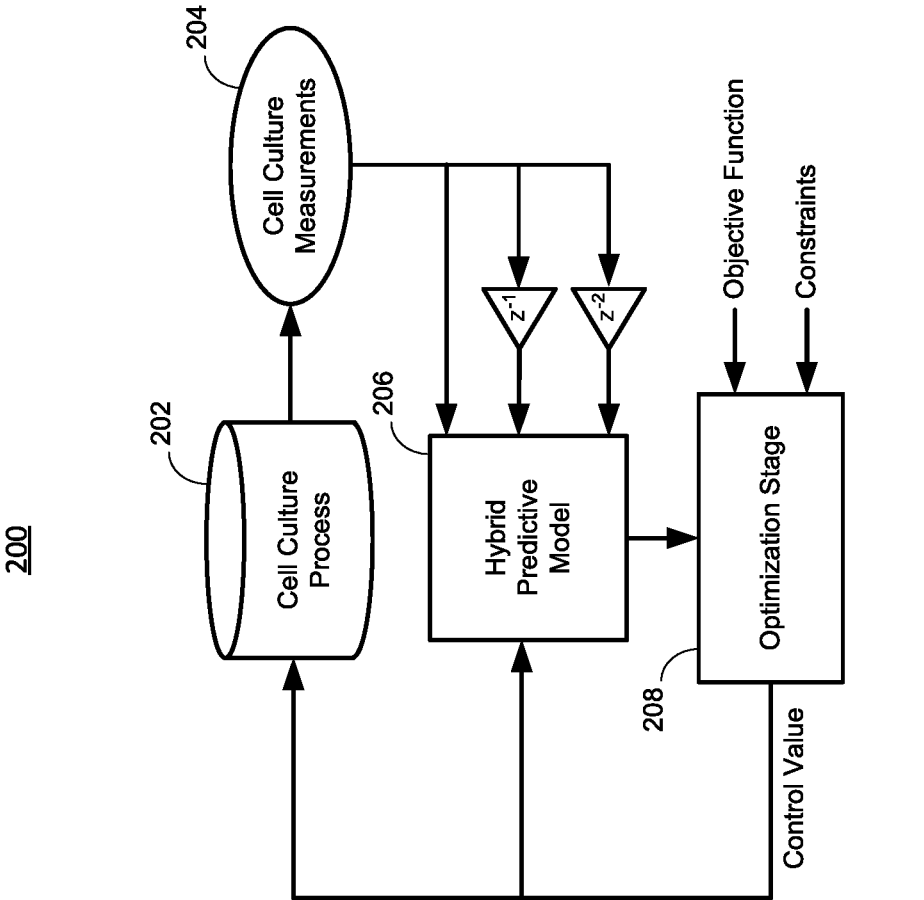
FIG. 2 is a block diagram of an example architecture that may be implemented in the system of FIG. 1.

FIG. 2 is a block diagram of an example architecture 200 that may be implemented in the system 100 of FIG. 1. In FIG. 2, a cell culture process 202 takes place in the bioreactor 102 of FIG. 1. Various cell culture measurements 204 (i.e., measured cell culture attribute values) are obtained by the measurement unit 140, using the analytical instrument(s) 104 of FIG. 1. As noted above, the cell culture measurements 204 may include concentrations of one, some, or all of a set of metabolites in the cell culture (e.g., glucose, lactate, sodium, potassium, ammonium, and/or glutamine), and possibly one or more other types of measured cell culture attributes, such as VCD, TCD, viability, osmolality, etc. A data driven model such as JIT (Just in Time) or CNN (convolutional neural network) may be used to provide an approximation of cell culture measurement.

The cell culture measurements 204 are inputs to a hybrid predictive model 206, which includes the first principle model 150 and data-driven model 152 of FIG. 1 (either or both of which may include multiple models, as discussed above). In FIG. 2, delay elements ($z^{-1}$ and $z^{-2}$) are used to indicate that past cell culture measurements 204 are also provided as inputs to the hybrid predictive model 206. FIG. 2 shows a third-order (regression or neural network) model embodiment in which at least the data-driven model(s) of the hybrid predictive model 206 operates on values from the current time interval (e.g., current day, or current hour, etc.) and the previous two time intervals (e.g., past two days) for all of the cell culture measurements 204. In other embodiments, however, past values are only used for a subset of the cell culture measurements 204, and/or the predictive model is of a different order (e.g., second-order, fourth-order, etc.).

At each time interval, the hybrid predictive model 206 processes the inputs (i.e., current and past measured values) to generate predicted values of a cell culture attribute over a finite prediction horizon (e.g., the next four time intervals, or the next six time intervals, etc.) of the MPC 142, using the data-driven model 152 and first principle model 150 as discussed above.

At each time interval, in an optimization stage 208, the optimizer 146 operates on the predicted future values, and possibly also other information, to generate a control value (e.g., a set-point) for the input device 106, e.g., using predictive batch-trajectory optimization. The optimizer 146 (and the MPC 142 as a whole) strives to minimize the difference between the quantities of the cell culture variables and the set-points while ensuring that the variables remain within the specification. Thus, an optimization problem over a finite time horizon can be formulated as a constrained optimization problem for every batch.

The optimizer 146 applies the predicted values (at each time interval of the prediction horizon) as inputs to an objective function, which determines control values at each time interval of the control horizon. The optimal control values are those that optimize (e.g., minimize) the objective (cost) function, subject to a number of constraints on the dependent and/or independent variables. Constraints may include, for example, a minimum glucose feed (infusion) rate or metabolite concentration, a maximum glucose feed rate, and/or other suitable constraints. The objective function may operate on each cell culture attribute that has a desired (set-point) value, such as different desired concentrations for different metabolites. The optimizer 146 may then determine the control value (e.g., set-point for a glucose pump feed rate) to guide the cell culture process to the desired objective(s).

The primary goal, in some embodiments, is to maximize productivity of the bioprocess while the byproducts are minimized (i.e., by manipulating the times, amount and ways to feed glucose to the culture). As a result, desired thresholds may be defined for each variable, and the objective function (solved by the optimizer 146) may be developed as the summation of quadratic errors between the variables and their desired set points over the time horizon, $$\min J(X_j[i], \text{feed}[i])$$

$$s \cdot t : X_j (j=1, \ldots, M), \text{feed} \qquad \text{(Equation 1A)}$$

where $$J(X_j(i), \text{feed}[i]) = \Sigma_{k=1}^{Np} \Sigma_{j=1}^{M} W_j (X_j[i+k] - X_j^{ref}[i+k])^2 + \Sigma_{l=1}^{Nc} W_{feed}(\text{feed}[i+l-1] - \text{feed}[+l-2])^2 \qquad \text{(Equation 1B)}$$

where $i$ is the time interval, $N_p$ is the number of time intervals in the prediction horizon, $N_c$ is the number of time intervals in the control horizon, M is the number of variables for which set-points/targets are known (e.g., 11 if the objective function accounts for VCD, TCD, viability, osmolality, and glucose, lactate, glutamate, glutamine, ammonium, potassium, and sodium concentrations), $W_j$ and $W_{feed}$ are weight parameters for the state $X_j[i]$ and feed (input), respectively, and $X_j^{ref}$ is the set-point for the state $X_j[i]$. The parameters in Equation 1B should preferably be tuned for the specific cell culture process under consideration. As one example, normalized set-point values for VCD, TCD, viability, glucose, lactate, glutamine, glutamate, ammonium, sodium, potassium, and osmolality may be 2, 2, 85, 0.3, 0.1, 0.16, 0.08, 0.08, 0.22, 0.26, and 0.6, respectively.

Every bioprocess is productive when the cell culture variables vary with a predefined specification. If the cell culture variables go beyond the specification, the process would deviate from the norm and the quality of the product may be adversely impacted. Moreover, it generally does not make sense for concentrations of cell culture variables to become negative. Consequently, based on the bioprocess expectations, the normalized value of all bioprocess variables may be constrained, by the optimizer 146, to remain in particular boundaries (e.g., VCD and TDC no less than zero, lactate, glutamine, glutamate, ammonium, and potassium concentrations no greater than 1, glucose concentration between 0.2 and 0.8, viability between 0.4 and 1, sodium concentration between 0.18 and 1, and osmolality between 0.33 and 1).

In some embodiments, the linear and/or nonlinear models implemented by the hybrid prediction unit 144 have only one input: feed. In embodiments where non-zero weights are given (in Equation 1B) for variables other than VCD, this means that the controller is driving multiple variables toward their set-points with only a single input. Moreover, if the main objective is to maximize VCD, a high threshold value can be used while the other variables are constrained so that they remain within the desired ranges.

Notably, linear MPC is a convex optimization, while nonlinear MPC is non-convex. In order to solve either convex or non-convex problems, at each time interval/step, the optimizer 146 may iterate the gradient descent for Lagrangian function to optimize the process input over the prediction horizon (e.g., as discussed in Kiran et al., Control of Continuous Fed-Batch Fermentation Process Using Neural Network Based Model Predictive Controller, 2009, *Bioprocess Biosyst Eng,* 32, 801-808). For the convex problem, these iterations end up with a global minimum at each time step, while the non-convex problem has the potential of never converging. Additionally, the optimizer 146 in nonlinear MPC embodiments may truncate the iterations if the gradient descent method does not converge to global minima, which could report an incorrect value. Furthermore, the solution to the linear MPC is globally optimal when the state constraints are considered as soft constraints. If these constraints are hard constraints, then the solution to the optimization problem might become infeasible. As a result, the global optima obtained by the linear model in linear MPC may be considered as another advantage over the nonlinear models in MPC problems.

Returning now to the example of FIG. 2, the optimizer 208 provides the control value (e.g., feed rate, or feed volume, or feed rate or feed volume change, etc.) as a set-point to the cell culture process 202 (more specifically, to the input device 106), and also provides the control value to the hybrid predictive model 206. The hybrid predictive model 206, in this example, uses the control value as one of the model inputs along with the cell culture measurements 204.

Figure 3:
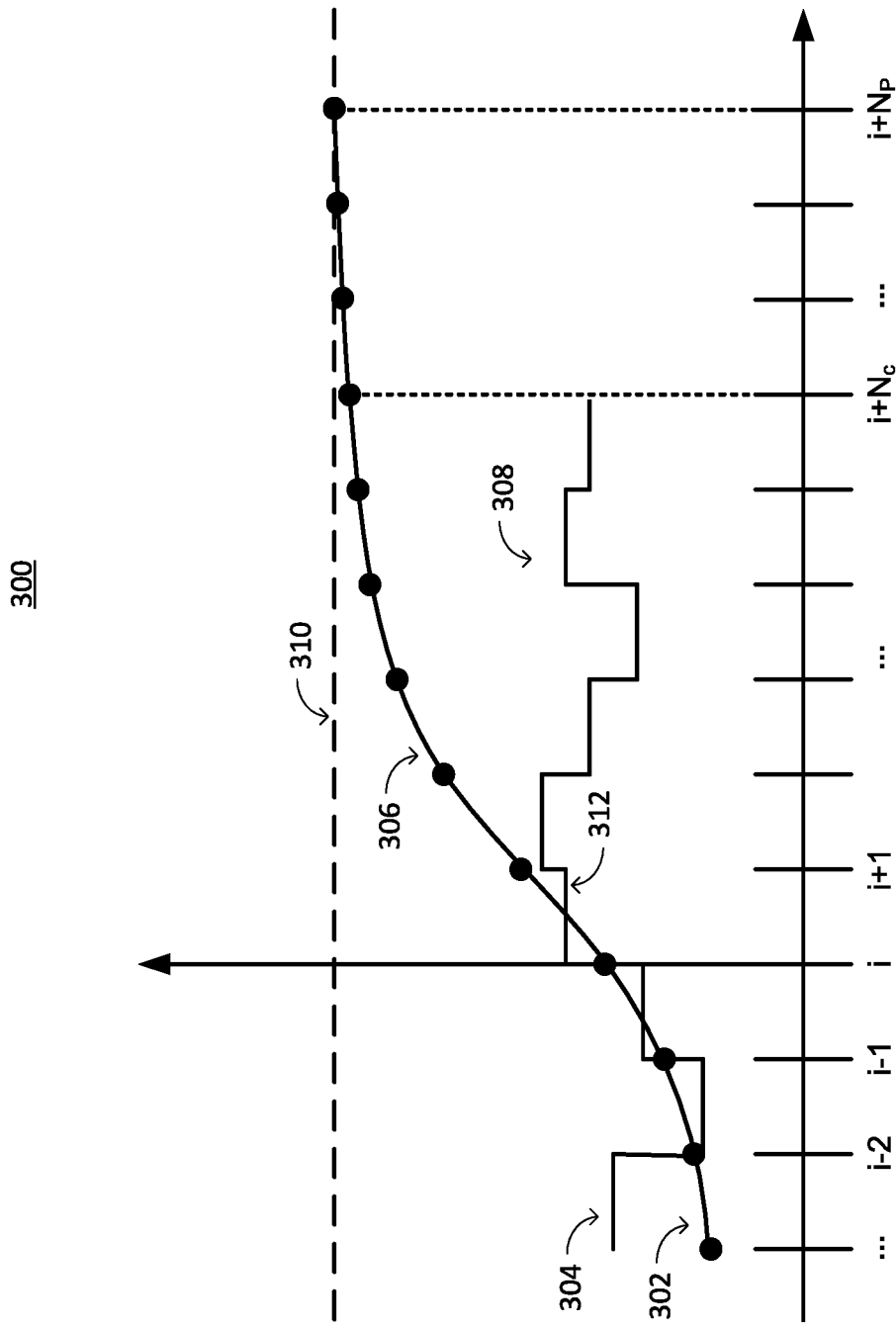
FIG. 3 depicts example operation of a model predictive controller that may be used as the model predictive controller of FIG. 1 and/or FIG. 2.

FIG. 3 depicts the operation 300 of an example MPC, such as the MPC 142 of FIG. 1, in a particular embodiment and scenario. In FIG. 3, the x-axis represents time intervals (i, i+1, etc.) while the y-axis represents amplitudes of various measured, predicted, or controlled values. The area to the left of the y-axis (i−1, i−2, etc.) represents past time intervals, the area to the right of the y-axis (i+1, i+2, etc.) represents future time intervals, and i represents the current time interval. FIG. 3 shows past (measured) cell culture attribute values 302 and past control values (set-points) 304, as well as future cell culture attribute values 306 predicted by the hybrid predictive model 206 (e.g., by first principle model 150 or data-driven model 152) over the prediction horizon $N_p$ and future control values/set-points 308 calculated by the MPC 142 over the control horizon $N_c$. In some embodiments, the CCPC application 130 only uses the first control value 312 within the control horizon to control the input device 106 at time i, and the prediction/optimization/control process is then repeated at the next time interval (with time i+1 in FIG. 3 becoming time i, time i+2 becoming time i+1, and so on).

Figure 4:
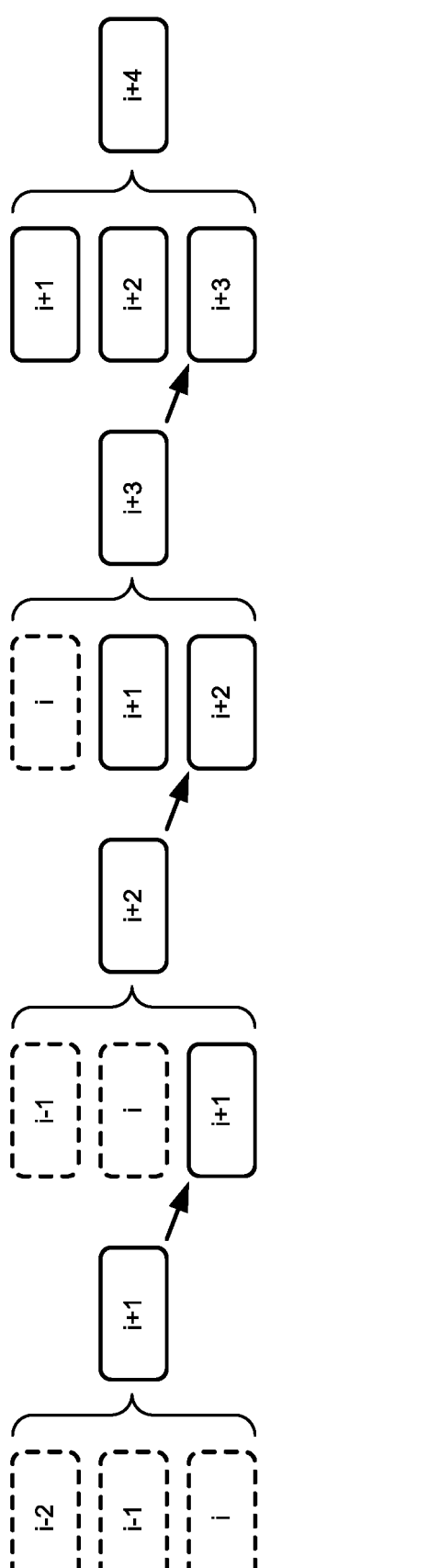
FIG. 4 depicts an example sequence of predictions made by the predictive model of FIG. 1 and/or FIG. 2.

FIG. 4 depicts an example sequence 400 of predictions that may be made by the hybrid prediction unit 144 of FIG. 1 (i.e., the first principle model 150 and/or the data-driven model 152). In FIG. 4, the parameter i represents the current time interval. Thus, in an example where each time interval is one day, i is the current day, i+1 is the next day, i−1 is the previous day, and so on. The sequence 400 shows the prediction of a third-order predictive model (e.g., a neural network or third-order regression model for the data-driven model 152) for the current time interval i. Boxes with a dashed outline represent analytical measurements (e.g., time intervals at which the analytical instrument(s) 104 take the measurements), while boxes with solid outlines represent values predicted by the third-order predictive model. As seen in this example, analytical measurements of a cell culture attribute for the current (i) and past two (i−1 and i−2) time intervals are input to the predictive model (possibly along with measurements of other cell culture attributes), which allow the predictive model to predict the value of the cell culture attribute at the next time interval i+1. The predictive model then uses the predicted value for time interval i+1, along with the measured values for i and i−1, to predict the value of the cell culture attribute at the next time interval i+2. The predictive model then uses the predicted values for time intervals i+1 and i+2, along with the measured value for i, to predict the value of the cell culture attribute at the next time interval i+3, and so on, out to a prediction horizon of four time intervals (to i+4), in this particular example.

First principle models have been found to show a physical relationship between feed and cell culture variables. To model this relationship properly, at each time point, the data of each model parameter generally needs to be available and identified. In order to identify the model parameters, the parameter data should preferably be collected with uniform time intervals. Adding bolus feed in a fed-batch bioprocess means that the feed level added might be zero at some sample times, which causes the process to have non-uniform feed input and, as a result, the model parameters may not be identified appropriately. That is, the sparse and non-uniform feed addition in the feed dataset can make the model insensitive to the feed, which is not desirable for controller design. However, in embodiments where glucose is the metabolite of interest, and is a major composition of the feed, one can simplify the feed complexity and focus on evaluating the mass balance between feed and glucose levels as follows:

(for a non-volume based dataset)

$$GLC[i+1] = GLC[i] + u[i] - k_s[i]\left(\frac{VCD[i+1]}{VCD[i]}\right) \qquad \text{(Equation 2a)}$$

(for a volume-based dataset)

$$GLC[i+1] =  \qquad \text{(Equation 2b)}$$
$$\left(GLC[i]V[i] + u[i]V[i] - k_s[i]V[i]\left(\frac{VCD[i+1]V[i+1]}{VCD[i]V[i]}\right)\right)/V[i+1]$$

where $k_s[i]$ is the consumption rate at time interval i, u[i] is the feed rate at time interval i, GLC [i] is the glucose concentration at time interval i, V[i] is the working volume of the media in the bioreactor at time interval i, and VCD [i] is the viable cell density at time interval i. All of the quality attributes may be in non-volume based format, and the last term on the right hand side of Equation 2a updates the consumption rate on a per-cell basis.

The consumption rate, $k_s[i]$ in Equations 2a and 2b is an internal process variable that is not easily measured. Thus, it may be estimated using Equations 2a and 2b and based on past values of glucose concentration and feed as follows:

$$k_s[i] = (u[i-1] + GLC[i-1] - GLC[i])\left(\frac{VCD[i-1]}{VCD[i]}\right) \qquad \text{(Equation 3)}$$

The consumption rate $k_s[i]$ is estimated based on the latest measurement, as this property normally has smooth changes over the culture. However, if rapid changes occur, it can be filtered using Monte-Carlo estimation of $k_s[i]$ by taking the average of the estimations from the beginning of the batch until time i.

The first principle model 150 can predict the future glucose concentration value for the next time interval using Equations 2 and 3, and then make a sequence of iterative predictions (e.g., similar to sequence 400) to predict glucose concentration for all time intervals 1, . . . , $N_p$ within the prediction horizon. In other embodiments, a different first principle model is used to predict glucose concentration, and/or first principle models are instead (or also) used to predict cell culture attributes other than glucose concentration.

Data-driven models (e.g., data-driven model 142) can similarly suffer from the sparsity in the feed data set if feed is used as an input in the model structure. Since glucose levels vary over time (i.e. do not suffer from sparsity) and have a physical relationship with the glucose feed, glucose can also be used as an input in the data-driven model. Thus, to have a comprehensive model of the whole bioprocess, a hybrid approach combines the data-driven model with the glucose mass balance model of Equations 2 and 3.

In some embodiments, as noted above, the data-driven model 152 is a linear model such as a linear regressor. For example, the data-driven model 152 may predict one or more cell culture attribute states as:

$$X_j[i+1] = a_j X_j[i] + b_j GLC[i] + c_j, \qquad \text{(Equation 4)}$$

where $X_j[\,\cdot\,]$ is an array with elements for each of j different cell culture attributes (e.g., VCD, metabolites other than glucose, viability, etc.), and where $a_j$, $b_j$, and $c_j$ are suitable constants (or arrays of j constants). Alternatively, the data-driven model 152 may use a model similar to Equation 4, but that includes additional terms for one or more past values (i.e., for time i−1, i−2, etc.) of $X_j[\cdot]$ and/or GLC[·]. In the example embodiment of Equations 2-4, the VCD at time interval i+1 predicted by the data-driven model 152 may be used as an input to the first principle model 150 (e.g., as an input to Equations 2 and 3).

Figure 5:
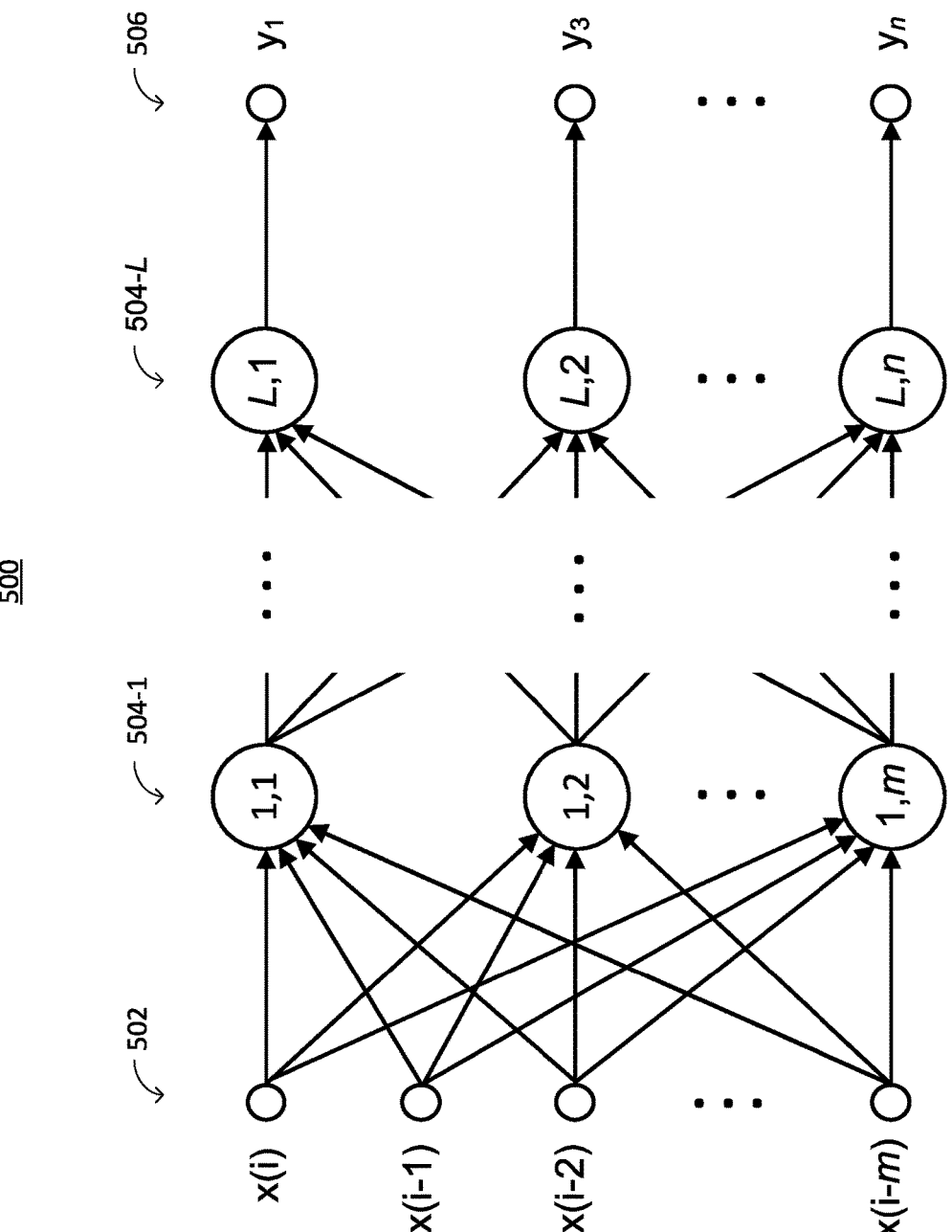
FIG. 5 depicts an example neural network that may be used as the data-driven model of FIG. 1.

The data-driven model 152 may instead be a feed-forward neural network. A two-layer neural network has been found to perform better than other neural networks. A simplified example of a feed-forward neural network 500 is shown in FIG. 5. Neural networks are proven general function approximators. That is, a neural network can approximate any nonlinear input-output behavior by manipulating the number of layers and the availability of training data, and by using the appropriate training method. As seen in FIG. 5, the neural network 500 includes a number of inputs in an input layer 502, internal nodes at each of a number of internal or hidden layers 504-1 through 504-L (with L being any suitable integer greater than zero), and a number of outputs in an output layer 506. In this example, the neural network 500 is an (m+1)-th order neural network that operates on inputs from the current day or other time interval (x(i)) as well as each previous time interval back to (and including) the previous m-th time interval x(i−m), where m is any suitable integer greater than zero. While FIG. 5 shows n outputs in layer 506, in some embodiments the neural network 500 at each iteration only includes a predicted value at the next time interval (i.e., y(i+1)). A prediction sequence similar to sequence 400 of FIG. 4 may then be used to run multiple iterations of the neural network 500, thereby generating additional predicted values (e.g., y(i+2), y(i+3), etc.) over the length of the desired prediction horizon.

The governing equation of the neural network 500 can be expressed as:

$$\hat{y}(i)=U\varphi(W(x(i-1)))$$ (Equation 5)

In Equation 5, x(i) and ŷ(i) are network input vectors applied at layer 502 and network output vectors produced at layer 506, respectively, and U and W are network weight matrices found by optimizing the training cost function. The neural network training cost function can be assumed to be a traditional "sum of squared errors" (SSE):

$$J = \frac{1}{2}\sum_{i=1}^{N}\|y(i) - \hat{y}(i)\|^2$$ (Equation 6)

In Equation 6, y(i) is the measured output and N is the number of training samples. Various local and global optimization approaches have been proposed to find network weight parameters by optimizing the training cost function such as the function of Equation 6. While local optimization approaches are relatively fast, they tend to be trapped in local minima of the optimization problem, which leads to poor generalization performance. In some embodiments, a scaled conjugate gradient approach is used to optimize the training cost function and find the network weight parameters. "Scaled conjugate gradient" is a fast and automated training algorithm that, unlike many other training algorithms, does not have any user-dependent parameters and is less likely to be trapped in the local minima of the optimization problem.

As noted above, in some embodiments, the neural network 500 is trained to predict a cell culture attribute (e.g., metabolite concentration, VCD, osmolality, etc.) at a given time interval i based on inputs at layer 502 that include values for that concentration/attribute at one or more earlier time intervals, and glucose concentration values at those one or more earlier time intervals (e.g., measured values). In some embodiments, for example, the neural network function for predicting cell attributes $X_j[\cdot]$ may be:

$$X_j[i+1]=NN(X_j[i],X_j[i-1],X_j[i-2],GLC[i],GLC[i-1],$$
$$GLC[i-2])$$ (Equation 7)

This third-order example may also be referred to as a "three-regressor neural network." The outputs $X_j[i+1]$ may be different outputs of a single neural network, or outputs of different neural networks operating in parallel. The hybrid prediction unit 144 may repeat Equation 7 via a prediction sequence similar to sequence 400 of FIG. 4 in order to predict values for all time intervals 1, . . . , $N_p$ within the prediction horizon.

Training of the data-driven model 152, whether a neural network or a regression model, can be challenging given the limited availability of granular, real-world historical data from cell culture processes. Metabolite concentrations may not have been measured and recorded each day, for example. In some embodiments, therefore, linear interpolation is used to provide more data points (i.e., "missing" values) for a larger training data set, although such interpolation tends to be inaccurate. In some embodiments, the data-driven model 152 continuously adapts by using measured and predicted values of a cell culture attribute as labels and inputs, respectively, in subsequent training of the data-driven model 152 (i.e., after the predictive model has been initially trained and put into use). In this manner, the predictive accuracy may continue to increase over time.

FIGS. 6-20 illustrate the performance of various embodiments of the intelligent control techniques discussed herein, for various embodiments of the MPC 142 and for various cell culture processes (e.g., different drug products and/or process parameters).

Figure 6A:
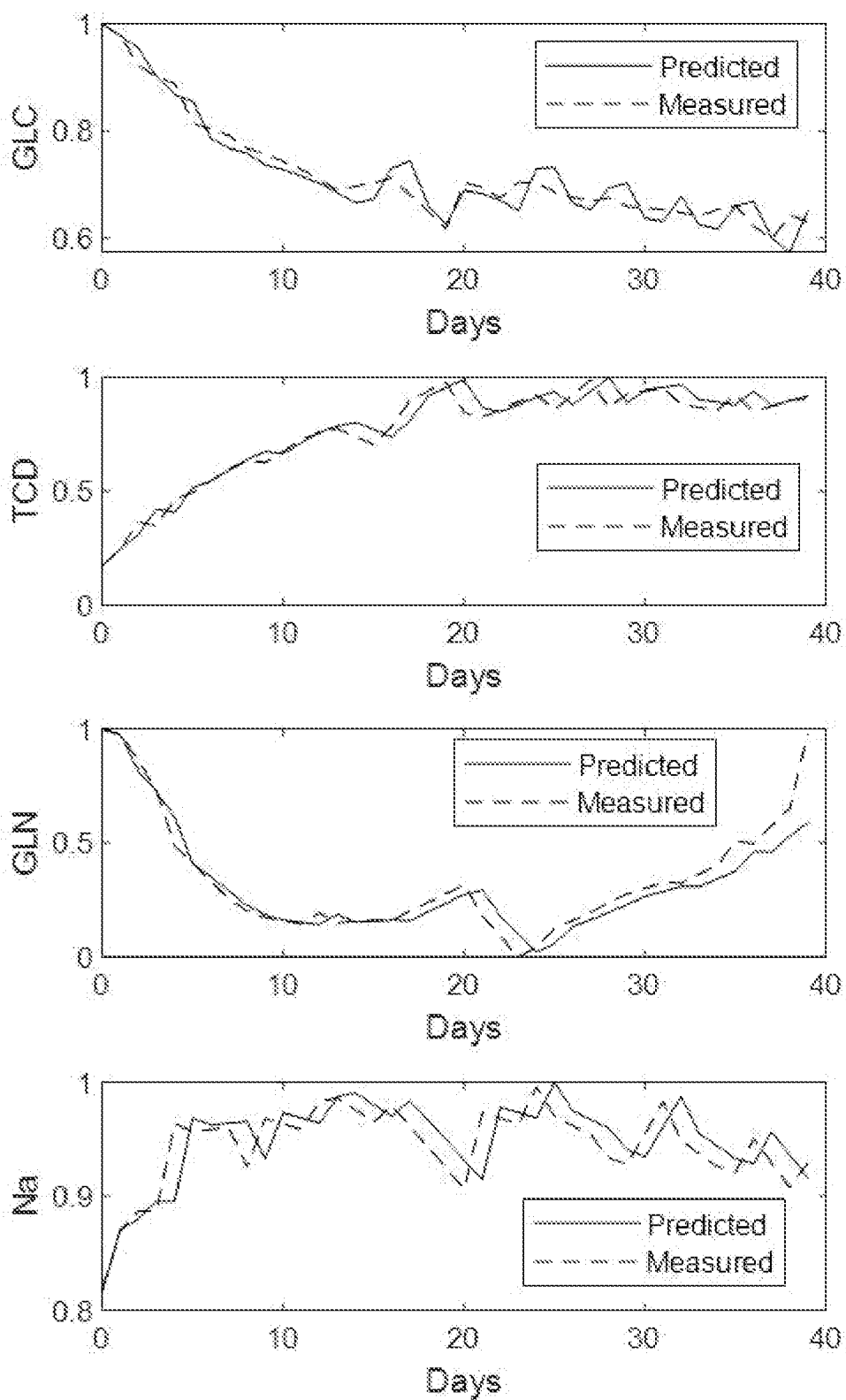
FIGS. 6A-C are normalized plots showing prediction performance for various cell culture attributes when using a linear regressor with a first principle model, for a first cell culture process.
Figure 6B:
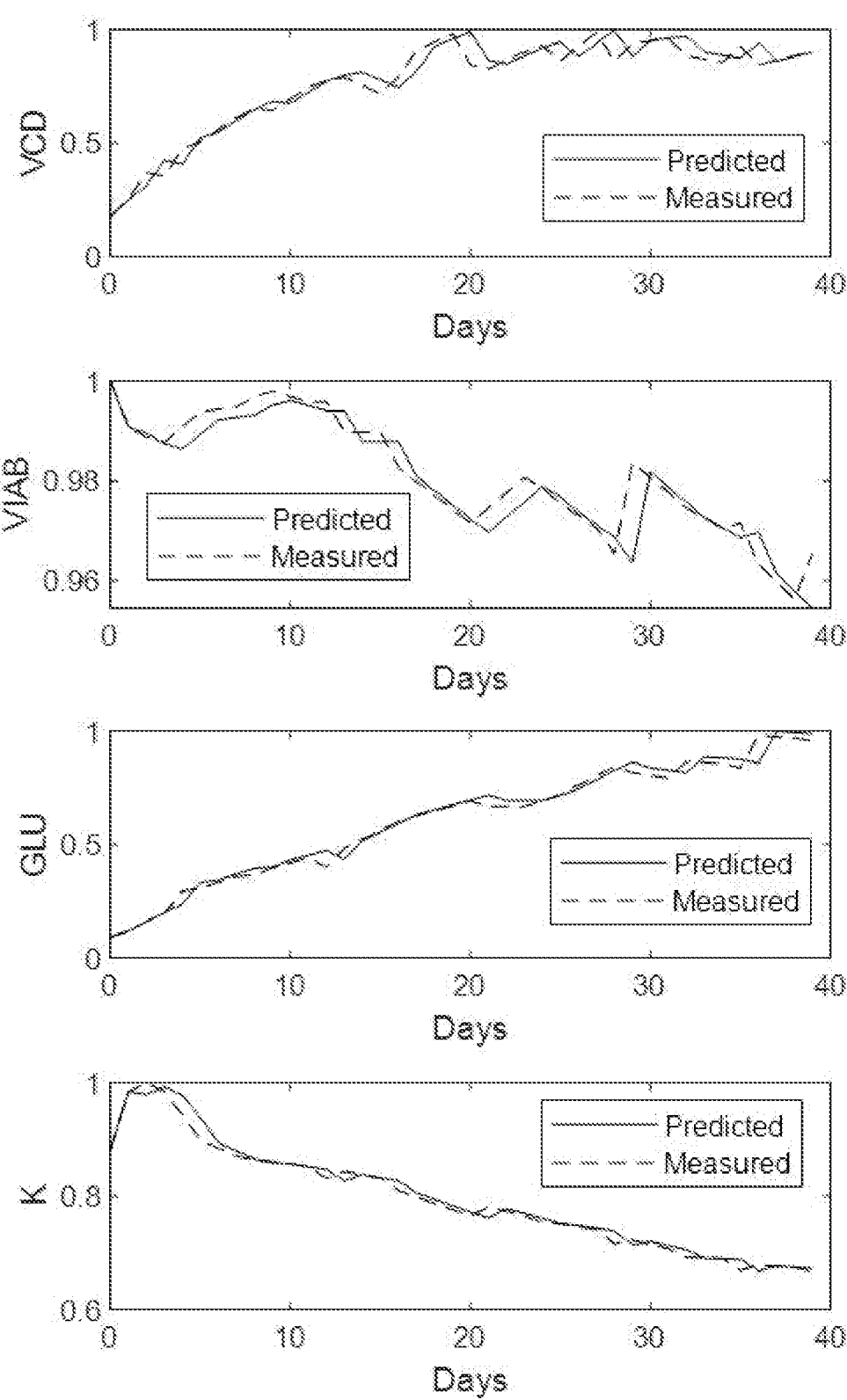
Figure 6C:
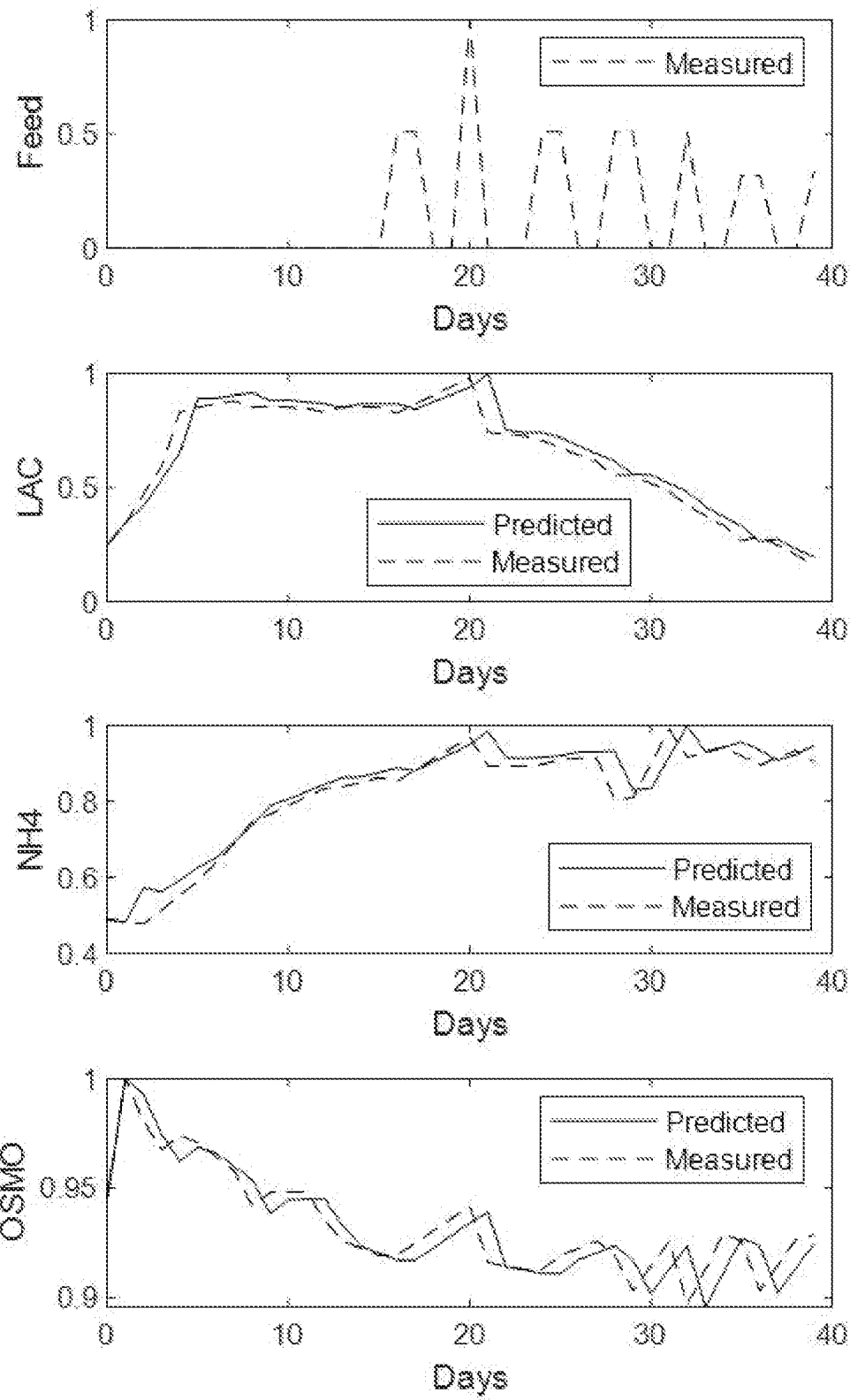

FIGS. 6A-C are normalized plots showing predictive performance of one embodiment of the MPC 142, for various cell culture attributes (glucose concentration (GLC), total cell density (TCD), glutamine concentration (GLN), sodium concentration (Na), viable cell density (VCD), viability (VIAB), glutamate concentration (GLU), potassium concentration (K), lactate concentration (LAC), ammonium concentration (NH4), and osmolality (OSMO)) when using linear regression for the data-driven models (e.g., data-driven model 152) and the first principle model (in this example, a mass balance model) of Equations 2 and 3 in a first cell culture process. "Predicted" traces in FIGS. 6A-C correspond to the predictions made by those models, while the "Measured" traces correspond to actual measurements. The (controlled) feed rate is also shown, in FIG. 6C.

Figure 7A:
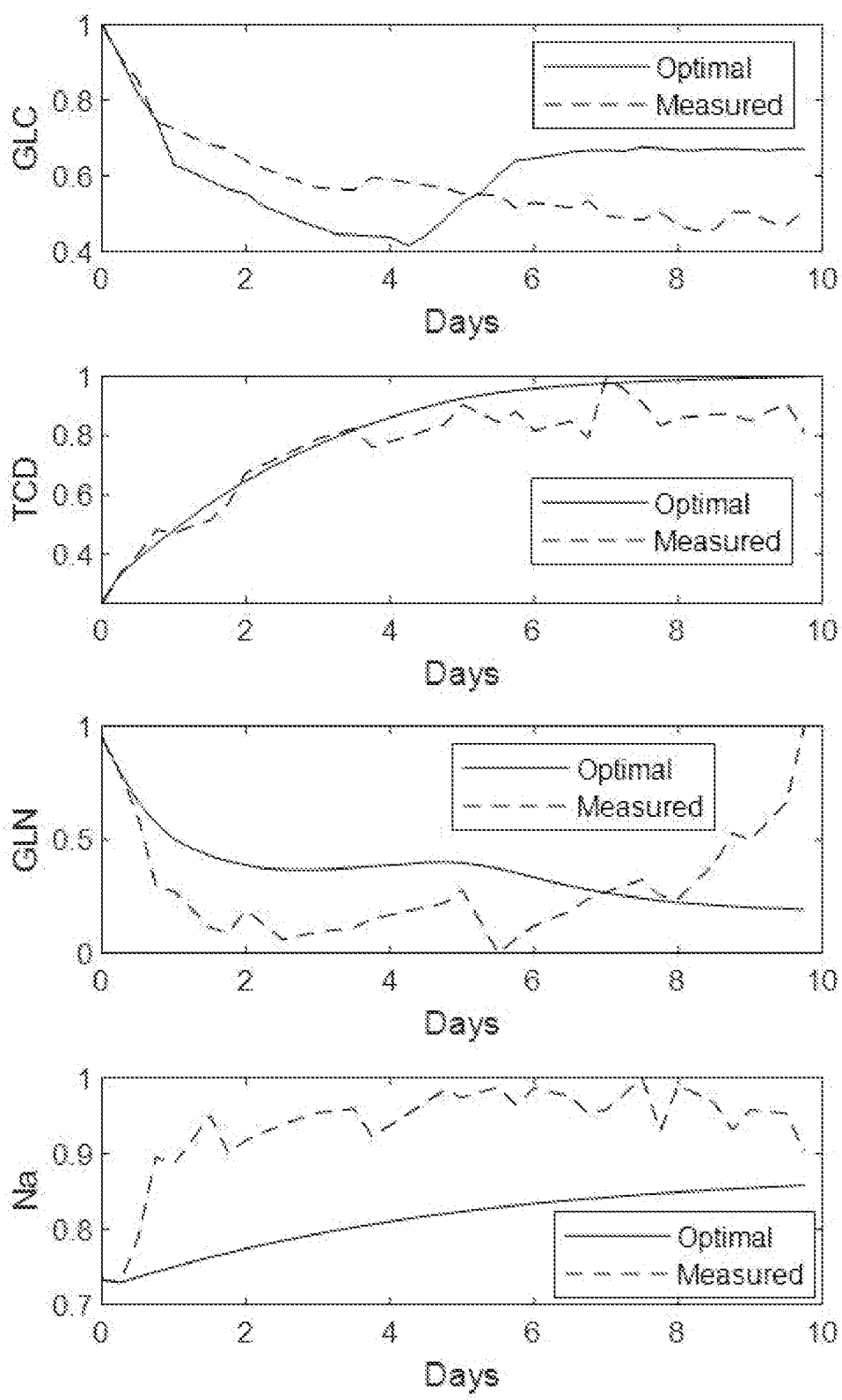
FIGS. 7A-C are normalized plots showing model predictive controller performance for various cell culture attributes when using a linear regressor with a first principle model, for the first cell culture process.
Figure 7B:
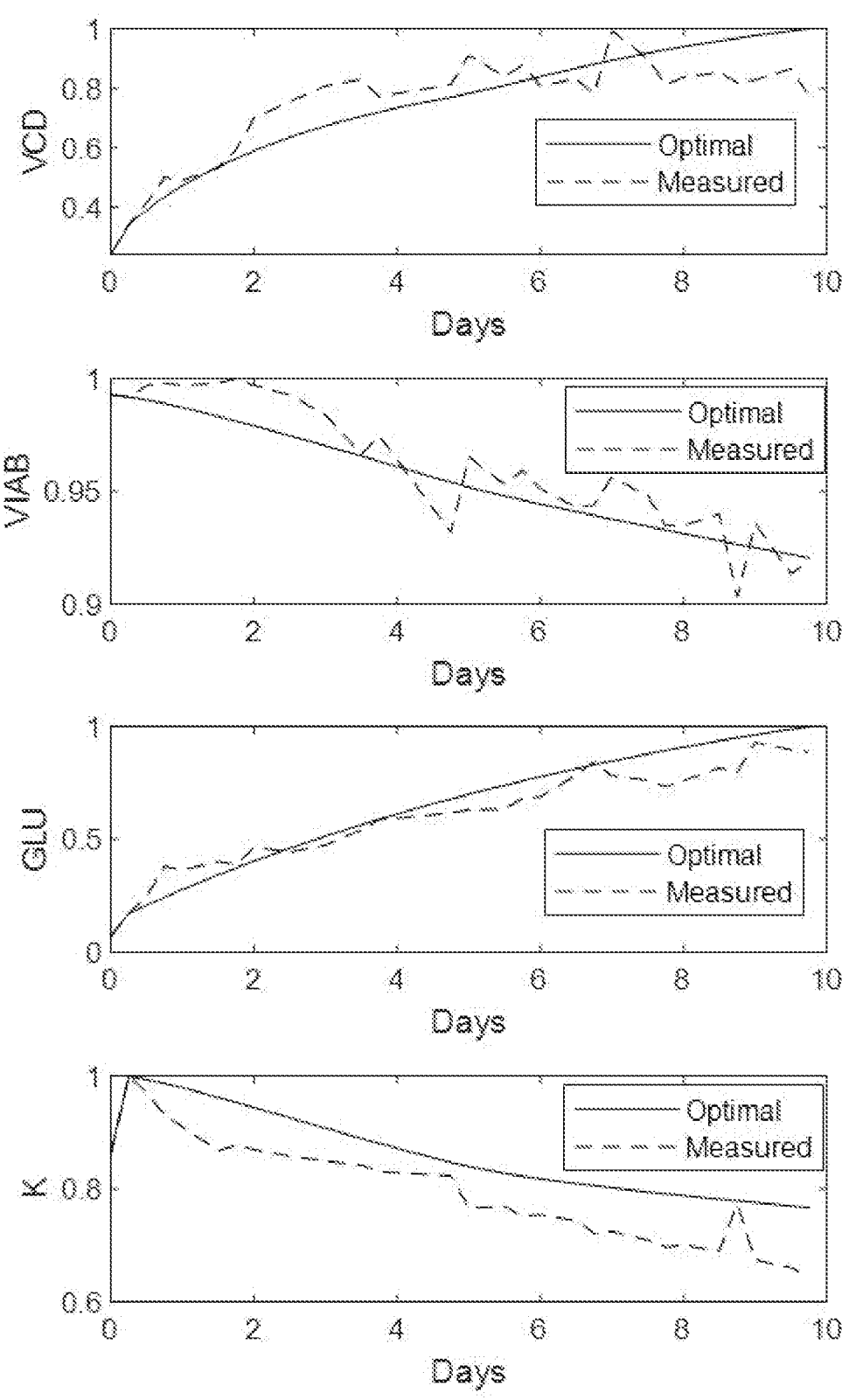
Figure 7C:
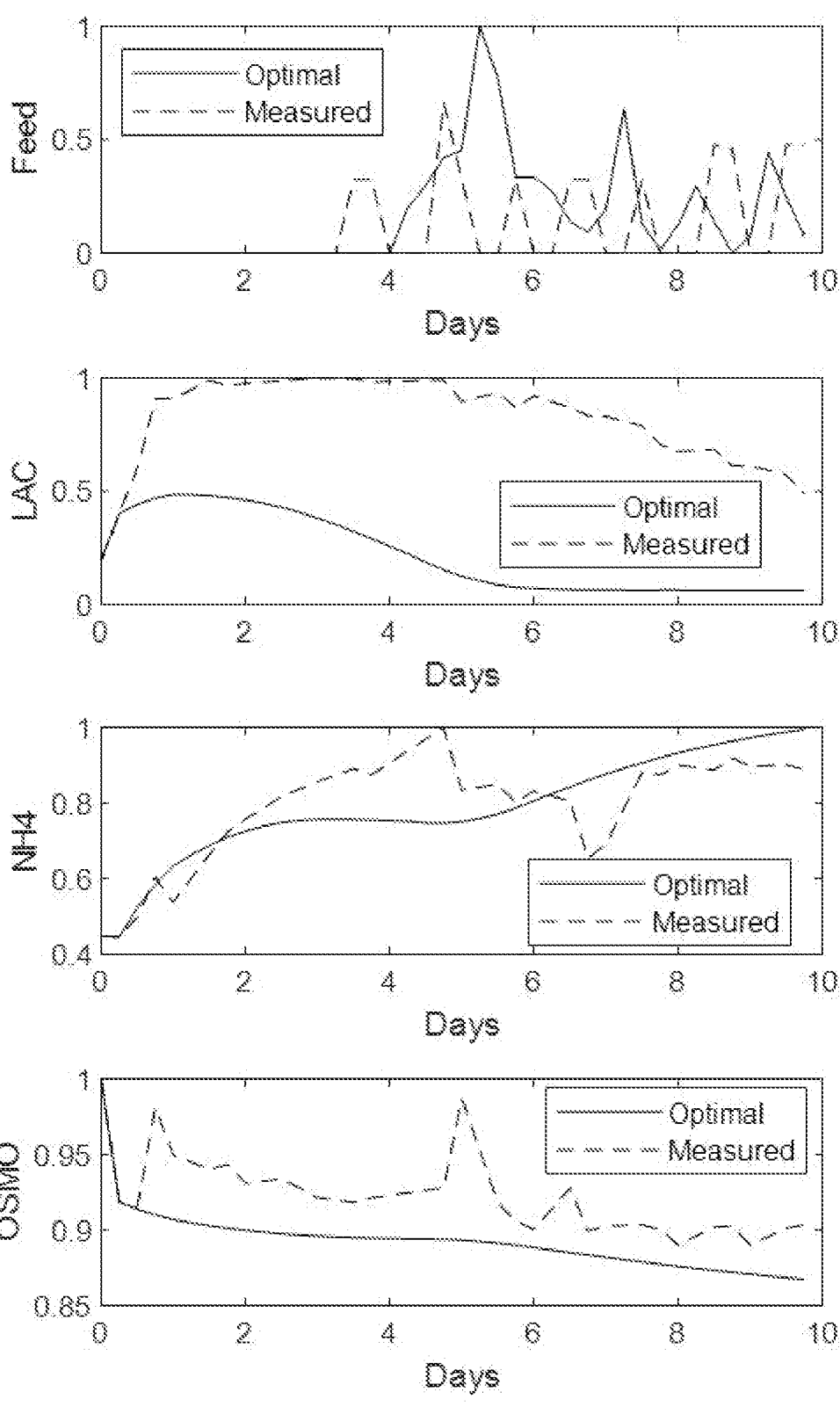

FIGS. 7A-C are normalized plots showing performance of the linear MPC 142 for the same embodiment and same cell culture process reflected in FIGS. 6A-C. Whereas FIGS. 6A-C illustrate how well the hybrid prediction unit 144 predicts various cell culture attributes, FIGS. 7A-C instead illustrate how well the system 100 using a linear model performs (in this particular embodiment), as shown by the "Measured" traces and as compared to the "Optimal" traces representing the solution to the optimization problem as calculated by MPC.

Figure 8A:
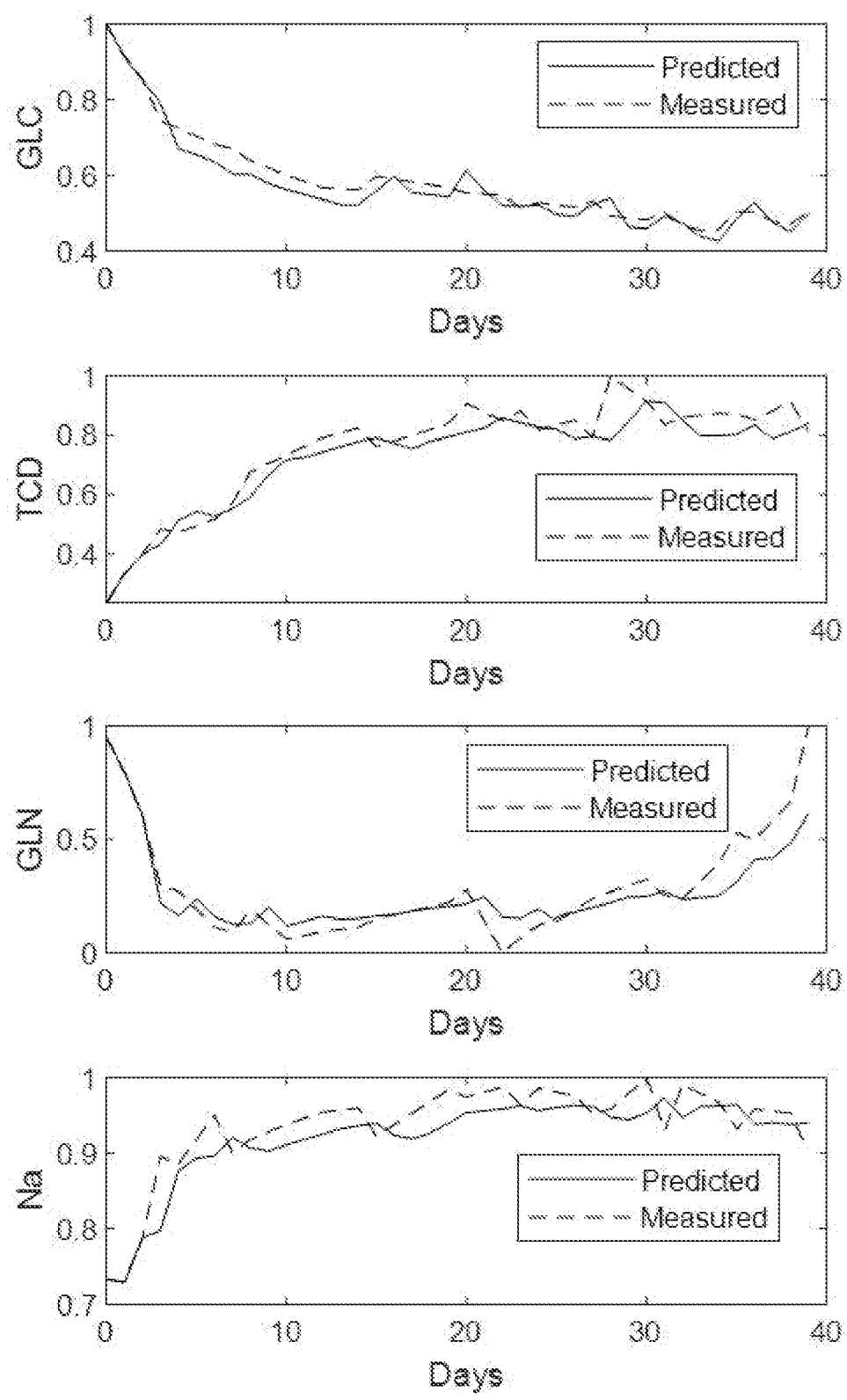
FIGS. 8A-C are normalized plots showing prediction performance for various cell culture attributes when using a neural network with a first principle model, for the first cell culture process.
Figure 8B:
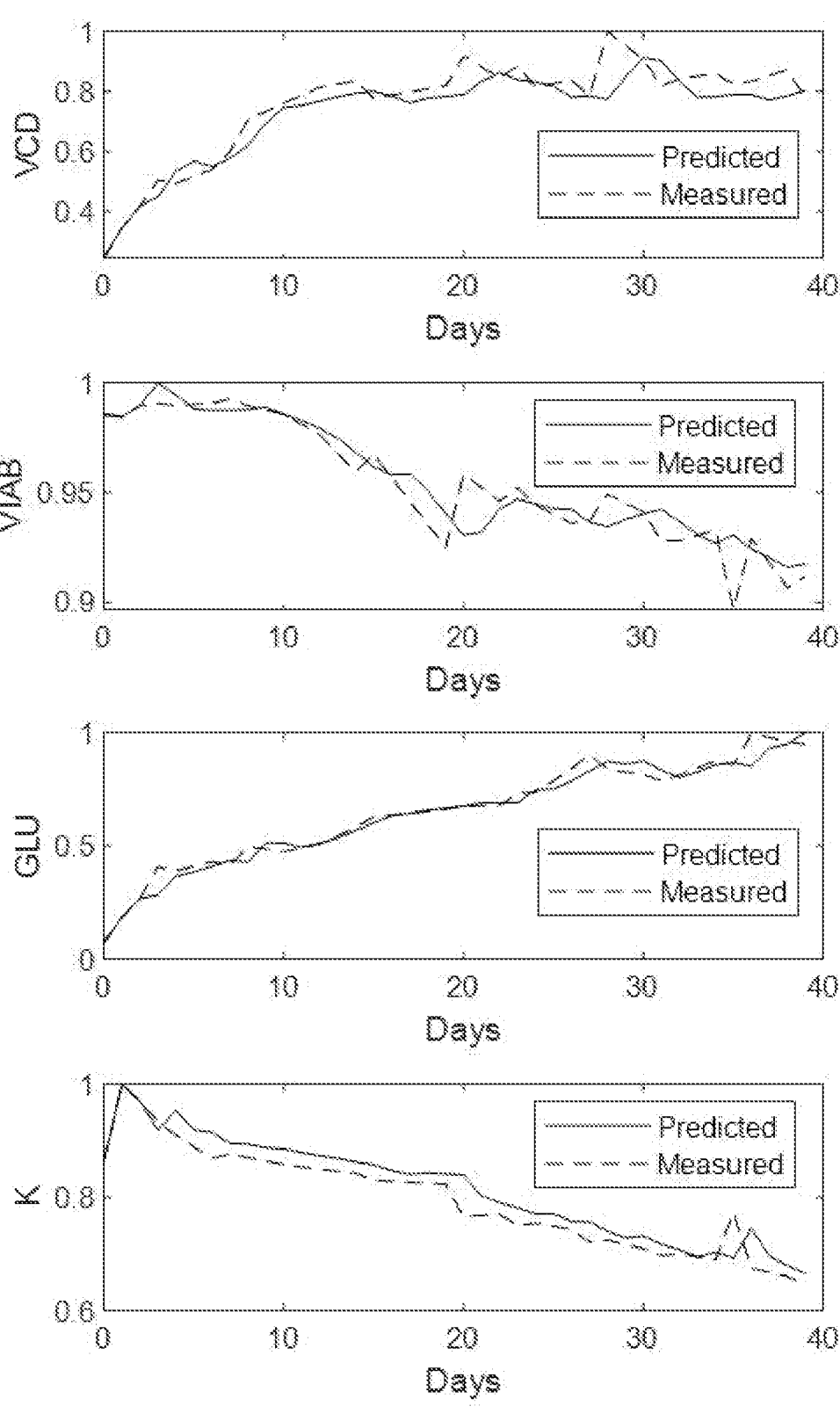
Figure 8C:
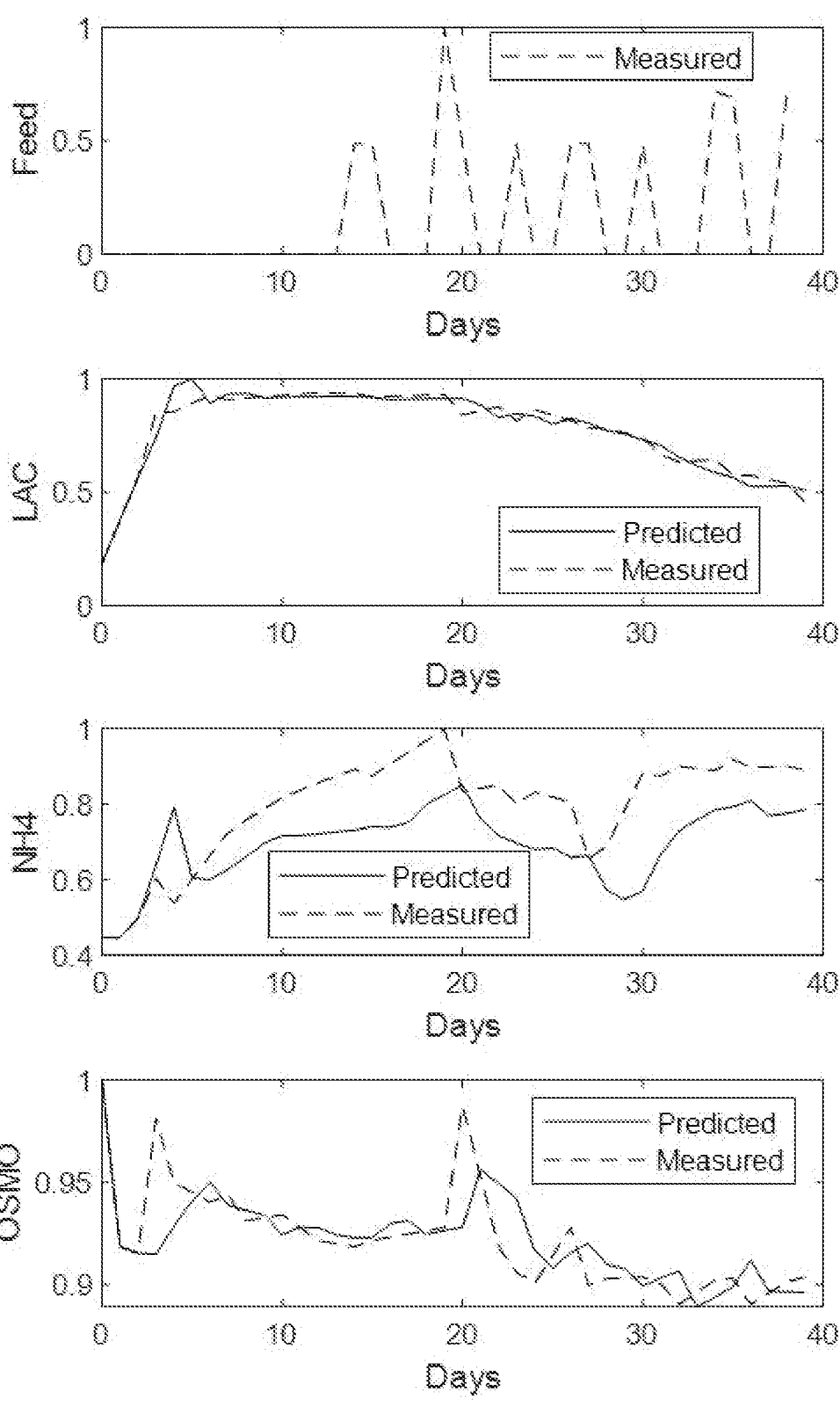

FIGS. 8A-C are normalized plots showing predictive performance of another embodiment of the MPC 142, for the same cell culture attributes and in the same cell culture process as FIGS. 6A-C, but using a feed-forward neural network for the data-driven models (e.g., data-driven model 152) and the first principal of Equations 2 and 3. Again, "Predicted" traces correspond to the predictions made by those models, while the "Measured" traces correspond to actual measurements. The measured feed rate is also shown.

Figure 9A:
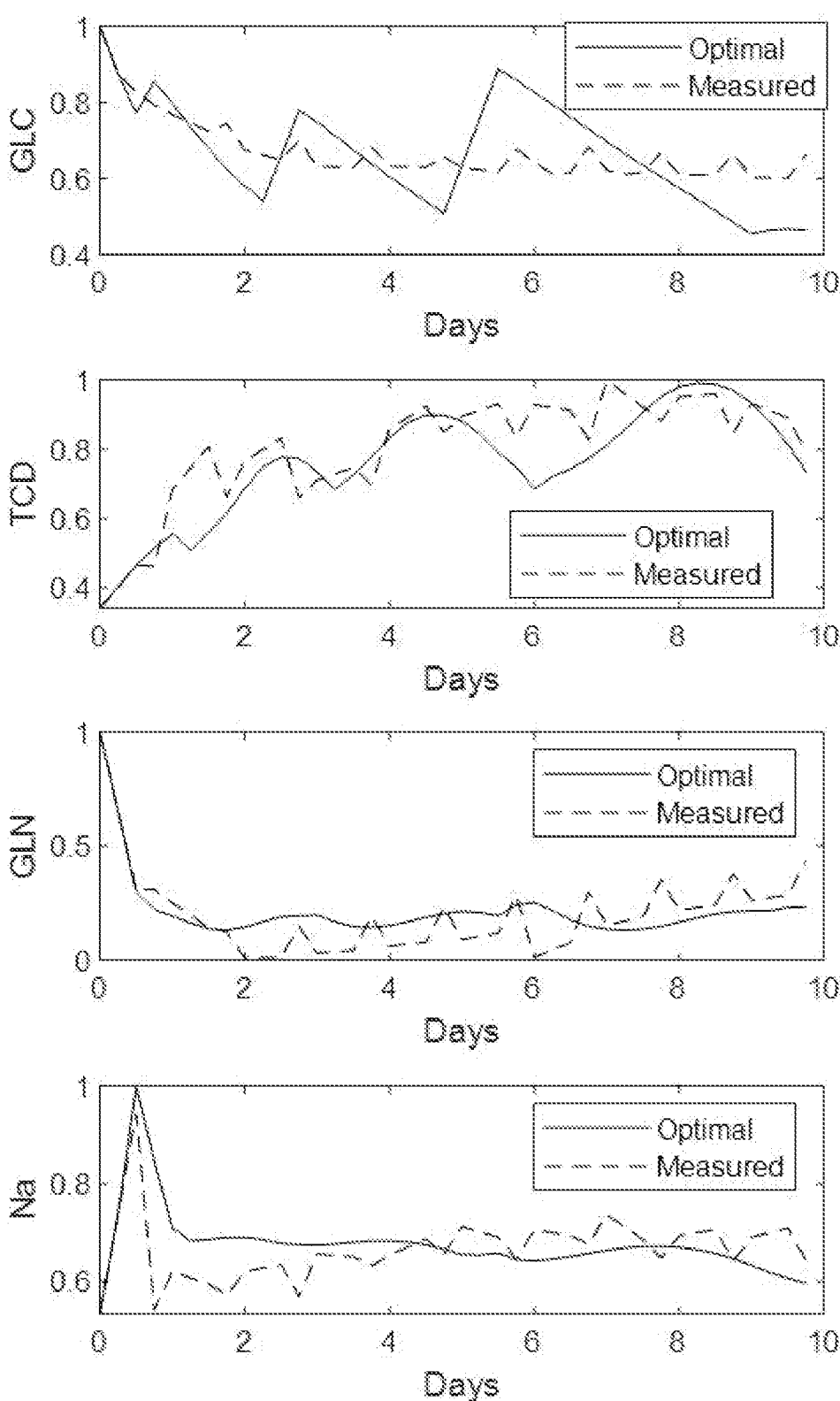
FIGS. 9A-C are normalized plots showing model predictive controller performance for various cell culture attributes when using a neural network with a first principle model, for the first cell culture process.
Figure 9B:
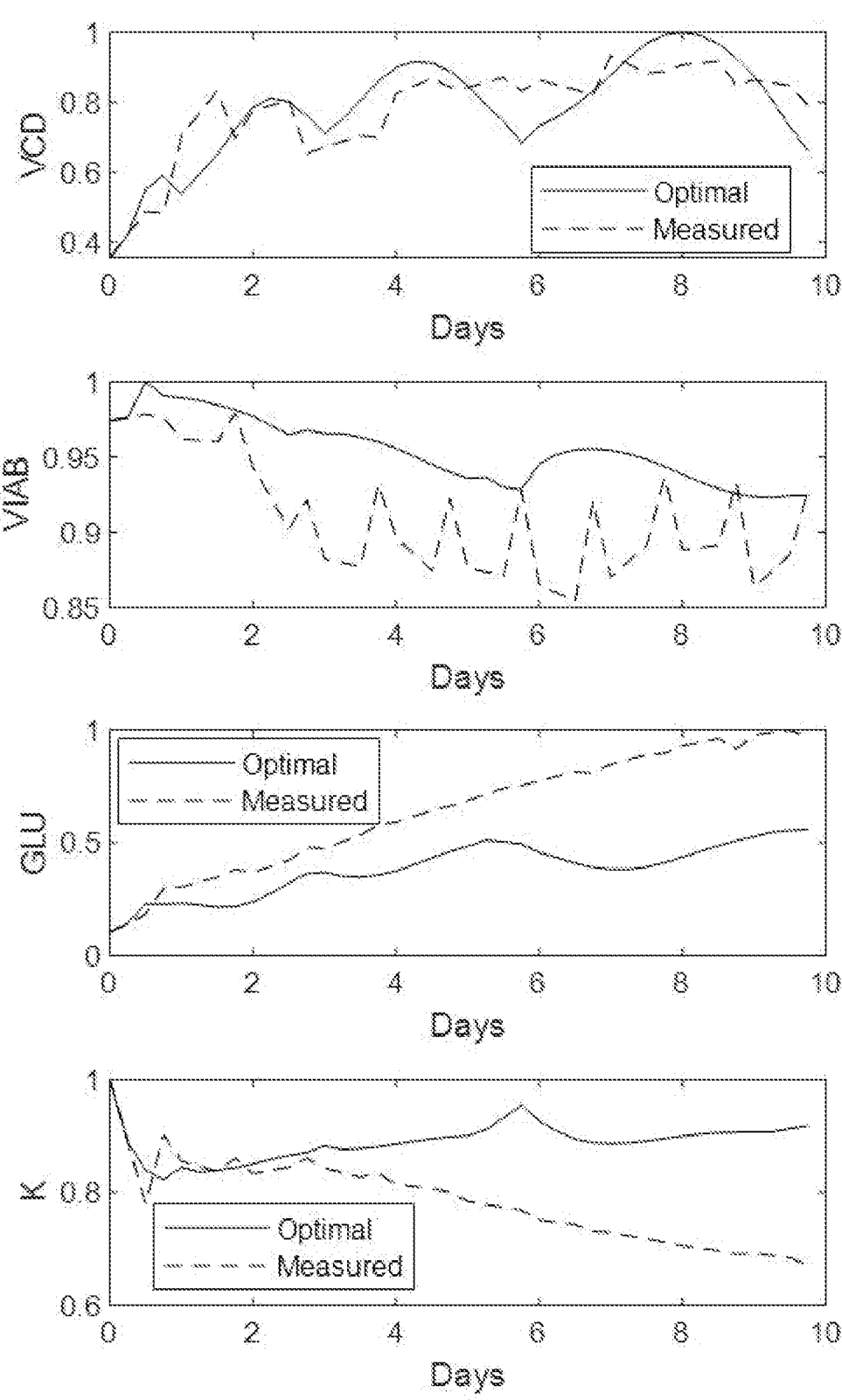
Figure 9C:
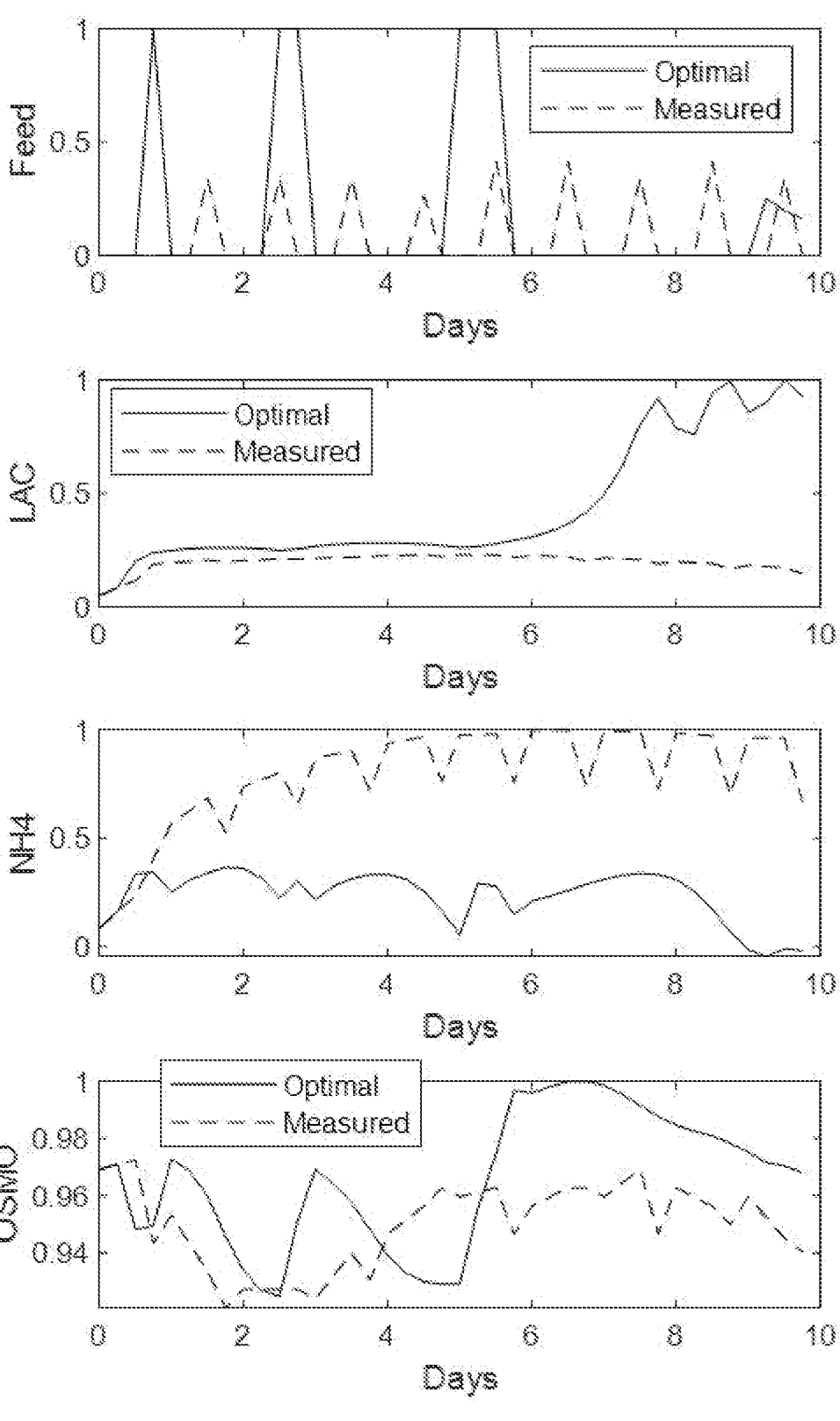

FIGS. 9A-C are normalized plots showing performance of the MPC 142 for the same embodiment and cell culture process reflected in FIGS. 8A-C. Whereas FIGS. 8A-C illustrate how well the MPC 142 (i.e., hybrid prediction unit 144) predicts various cell culture attributes, FIGS. 9A-C instead illustrate how well the system 100 performs (in this particular embodiment), as shown by the "Measured" traces and as compared to the "Optimal" traces representing the solution to the optimization problem as calculated by MPC.

The root mean square error (RMSE) for predictions made using the embodiment represented in FIGS. 6-7 (with a linear model), and using the embodiment represented in FIGS. 8-9 (with a nonlinear model, more specifically a neural network), is shown below in Table 1:

TABLE 1

| Cell Culture Attribute | Linear Model ($1^{st}$ Order) | Nonlinear Model ($3^{rd}$ Order) |
|---|---|---|
| VCD | 1 | 0.95 |
| TCD | 1 | 0.96 |
| VIAB | 1 | 1.04 |
| GLC | 1 | 1.03 |
| LAC | 1 | 1.13 |
| GLN | 1 | 1.26 |
| GLU | 1 | 1.67 |
| NH4 | 1 | 1.68 |
| Na | 1 | 0.97 |
| K | 1 | 1.06 |
| OSMO | 1 | 0.98 |

Figure 10A:
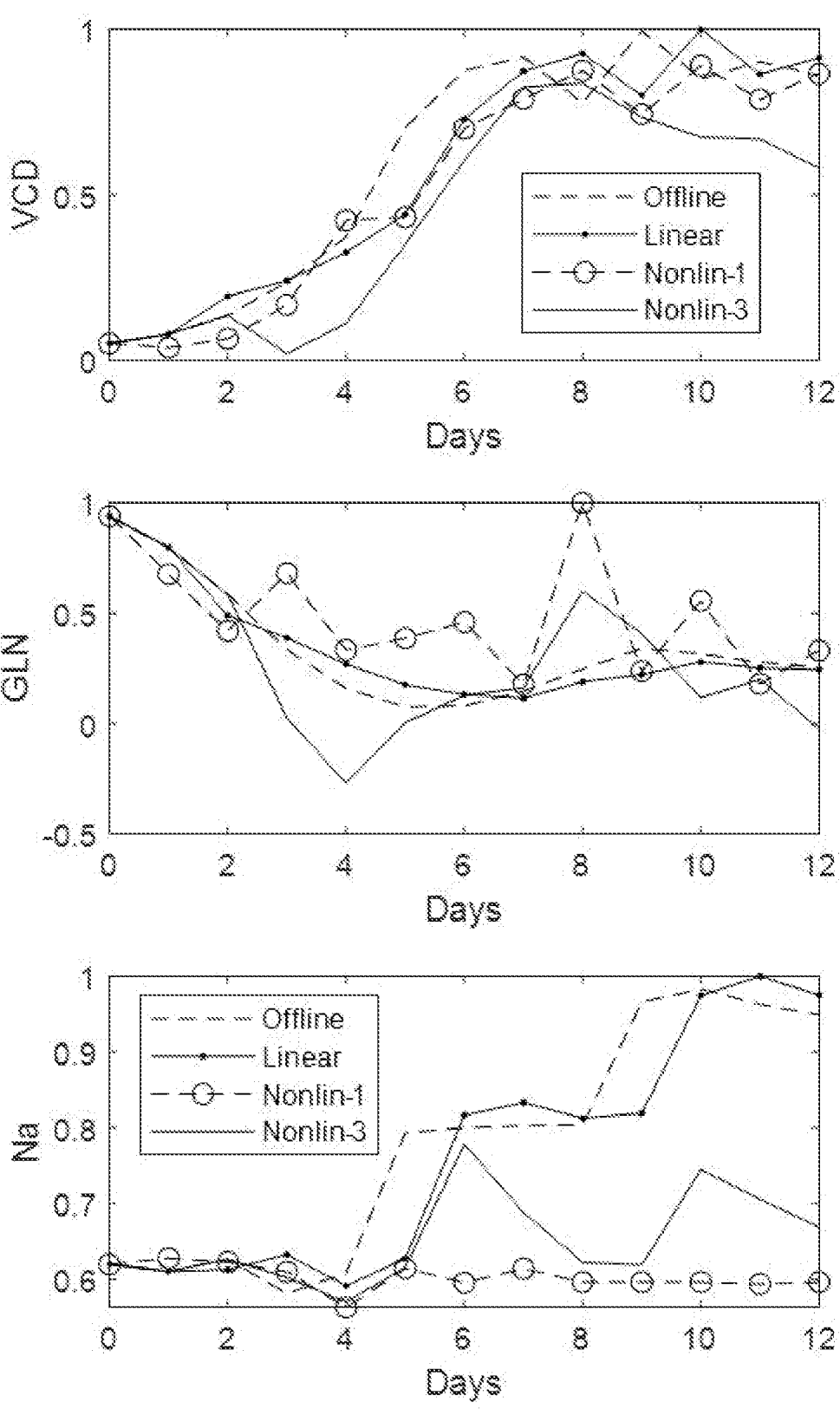
FIGS. 10A-C are normalized plots comparing prediction performance for various cell culture attributes when using a linear or nonlinear data-driven prediction model with a first principle model, for a second cell culture process.
Figure 10B:
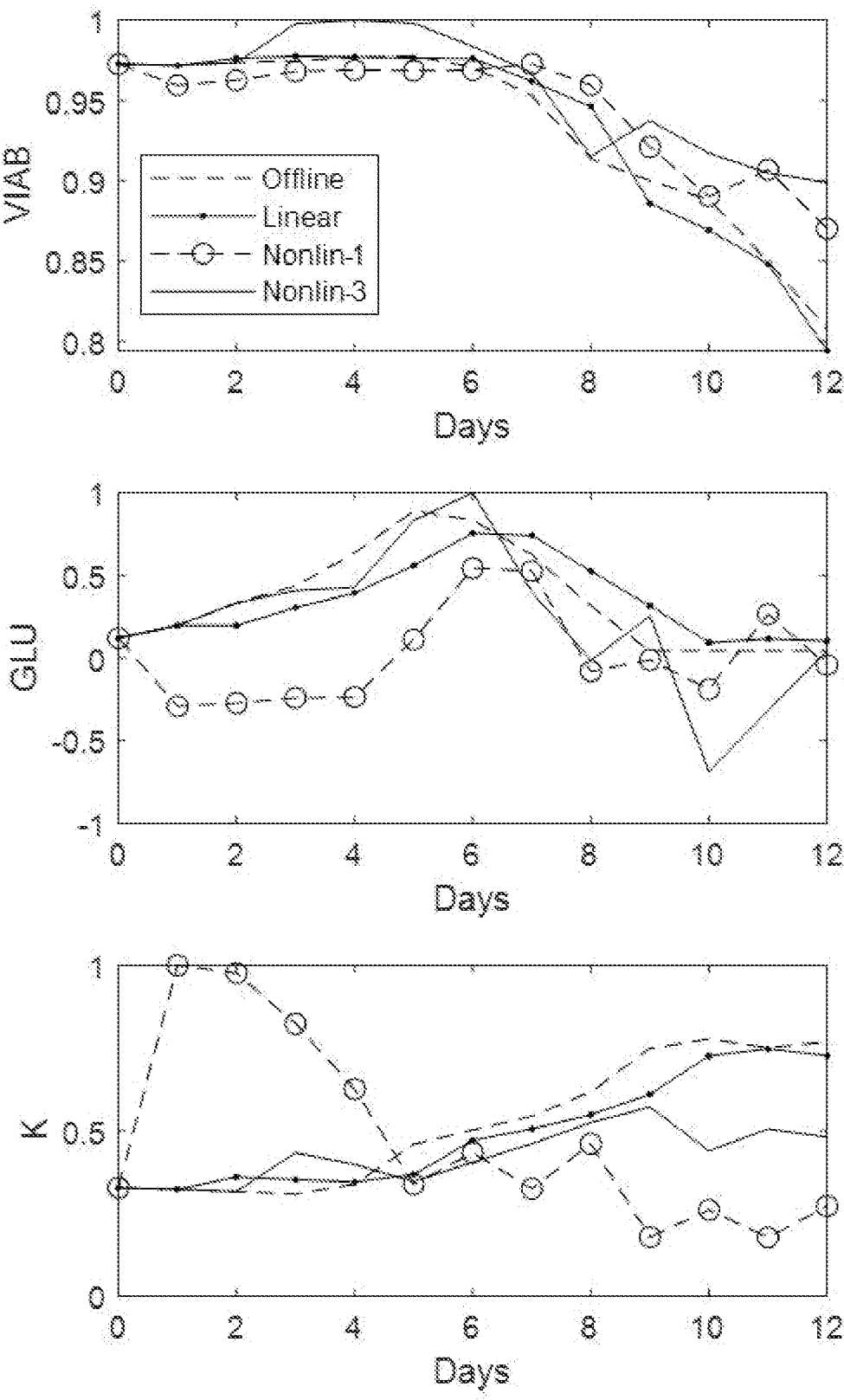
Figure 10C:
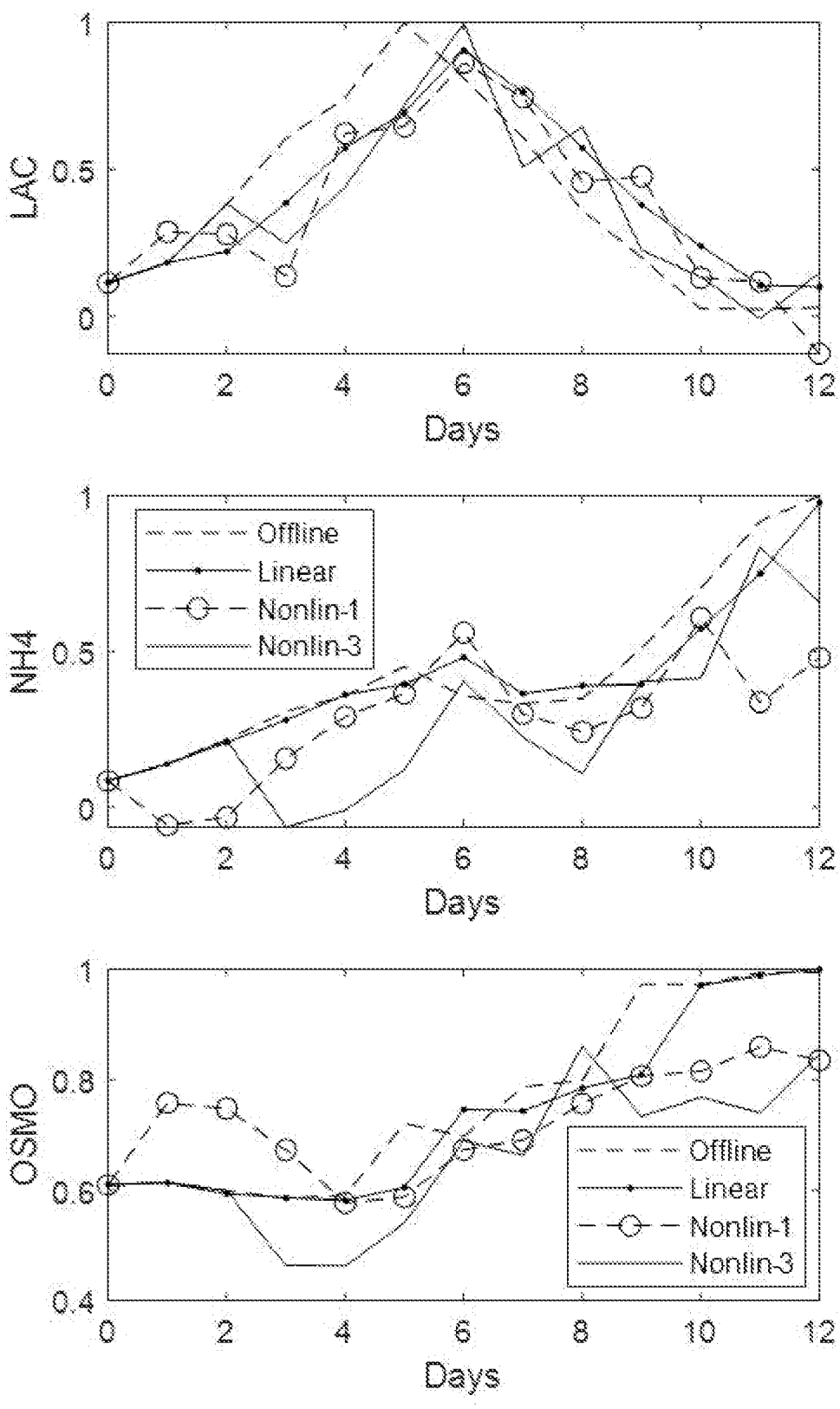
Figure 11A:
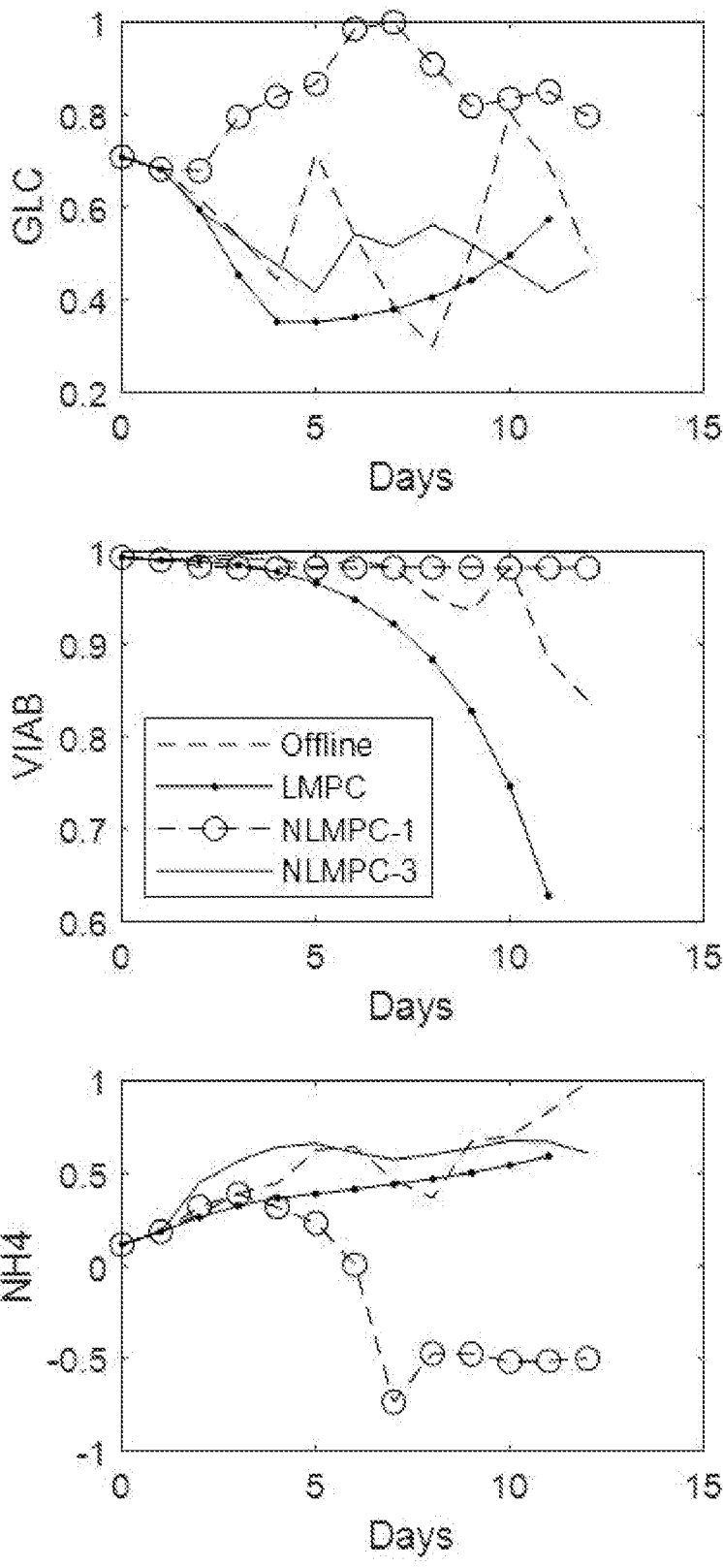
FIGS. 11A-D are normalized plots comparing model predictive controller performance for various cell culture attributes when using a linear or nonlinear data-driven prediction model with a first principle model, for the second cell culture process.
Figure 11B:
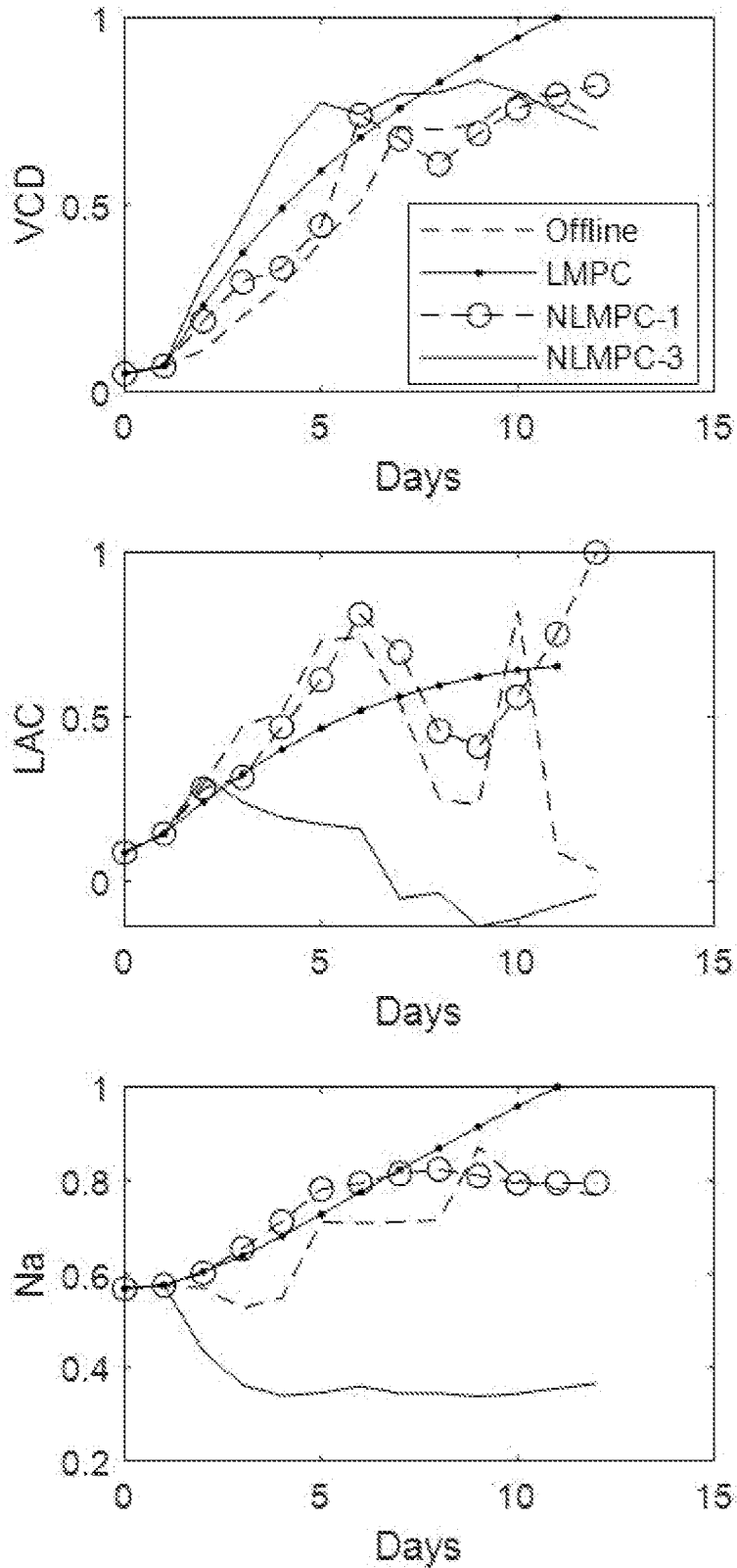
Figure 11C:
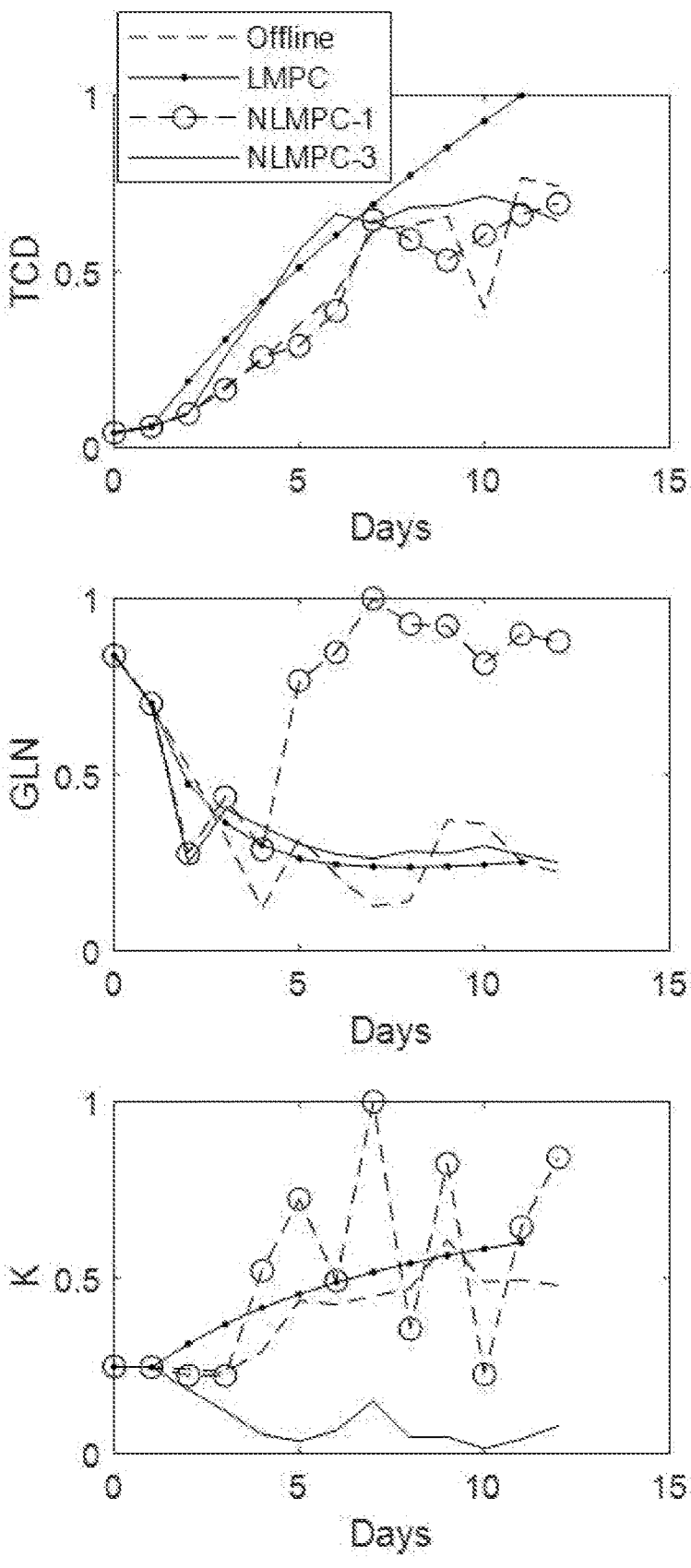
Figure 11D:
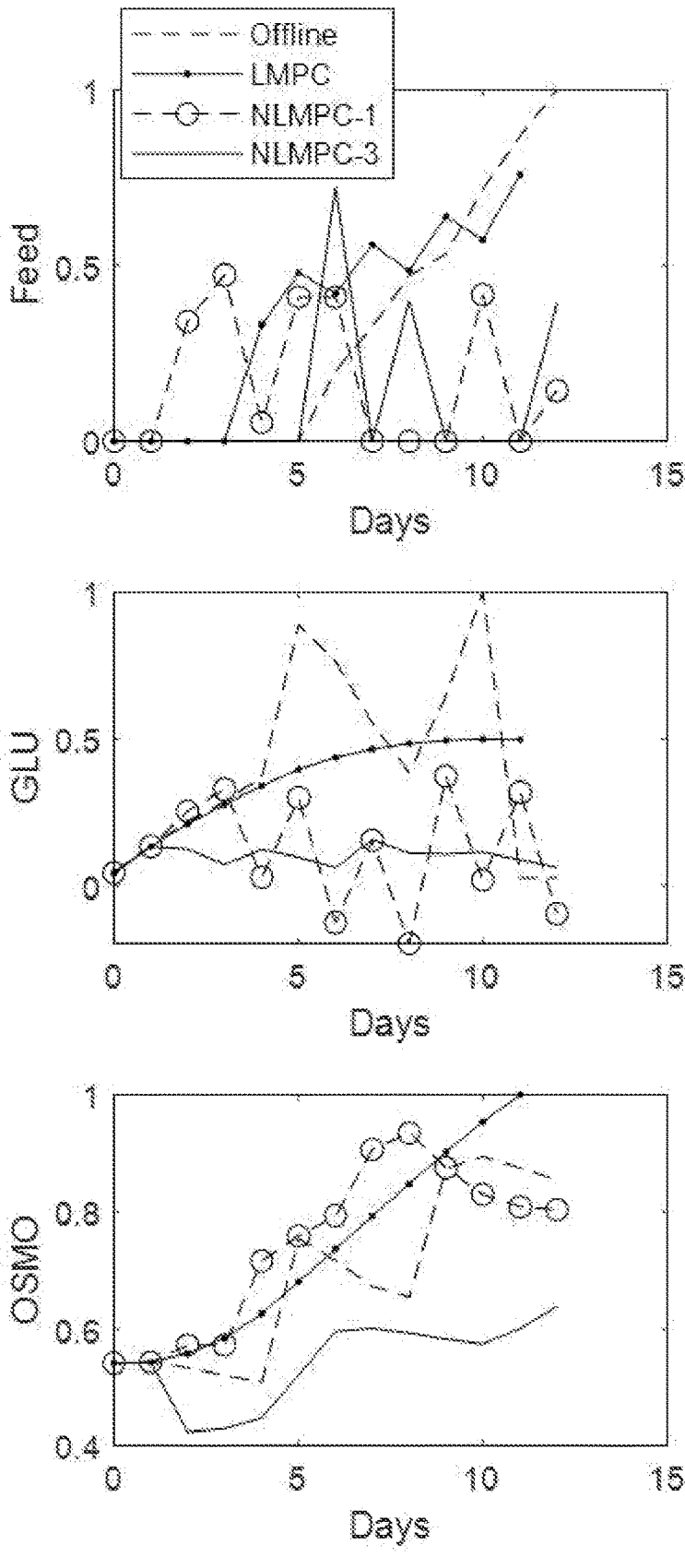

FIGS. 10A-C are normalized plots showing predictive performance of various embodiments of the MPC 142 for a different cell culture process than FIGS. 6-9. In particular, FIGS. 10A-C show predictive performance for embodiments in which the MPC 142 uses a linear regression model, a first-order nonlinear (feed-forward neural network) model, and a third-order nonlinear (feed-forward neural network) model, as compared to a system that did not use these predictive models (labeled "Offline" in FIGS. 10A-C).

FIGS. 11A-D are normalized plots showing performance of the MPC 142 for the same embodiment and same cell culture process reflected in FIGS. 10A-C, again with the "Offline" system results for comparison purposes. In FIGS. 11A-D (and other figures discussed below), "LMPC" represents the performance of the system 100 when the MPC 142 uses the linear regression model of FIGS. 10A-C, "NLMPC-1" represents the performance of the system 100 when the MPC 142 uses the first-order, feed-forward neural network of FIGS. 10A-C, and "NLMPC-3" represents the performance of the system 100 when the MPC 142 uses the third-order, feed-forward neural network of FIGS. 10A-C.

The normalized RMSE values for predictions made using the embodiments and cell culture process represented in FIGS. 10-11 are shown below in Table 2:

TABLE 2

| Cell Culture Attribute | Linear Model ($1^{st}$ Order) | Nonlinear Model (1st Order) | Nonlinear Model (3rd Order) |
|---|---|---|---|
| VCD | 1.00 | 1.22 | 1.92 |
| TCD | 1.00 | 1.35 | 2.16 |
| VIAB | 1.00 | 1.24 | 1.71 |
| GLC | 1.00 | 1.94 | 1.94 |
| LAC | 1.00 | 1.24 | 1.32 |
| GLN | 1.00 | 2.37 | 2.02 |
| GLU | 1.00 | 1.22 | 1.58 |
| NH4 | 1.00 | 2.01 | 1.74 |
| Na | 1.00 | 2.58 | 2.04 |
| K | 1.00 | 2.16 | 1.31 |
| OSMO | 1.00 | 0.97 | 1.39 |

Figure 12A:
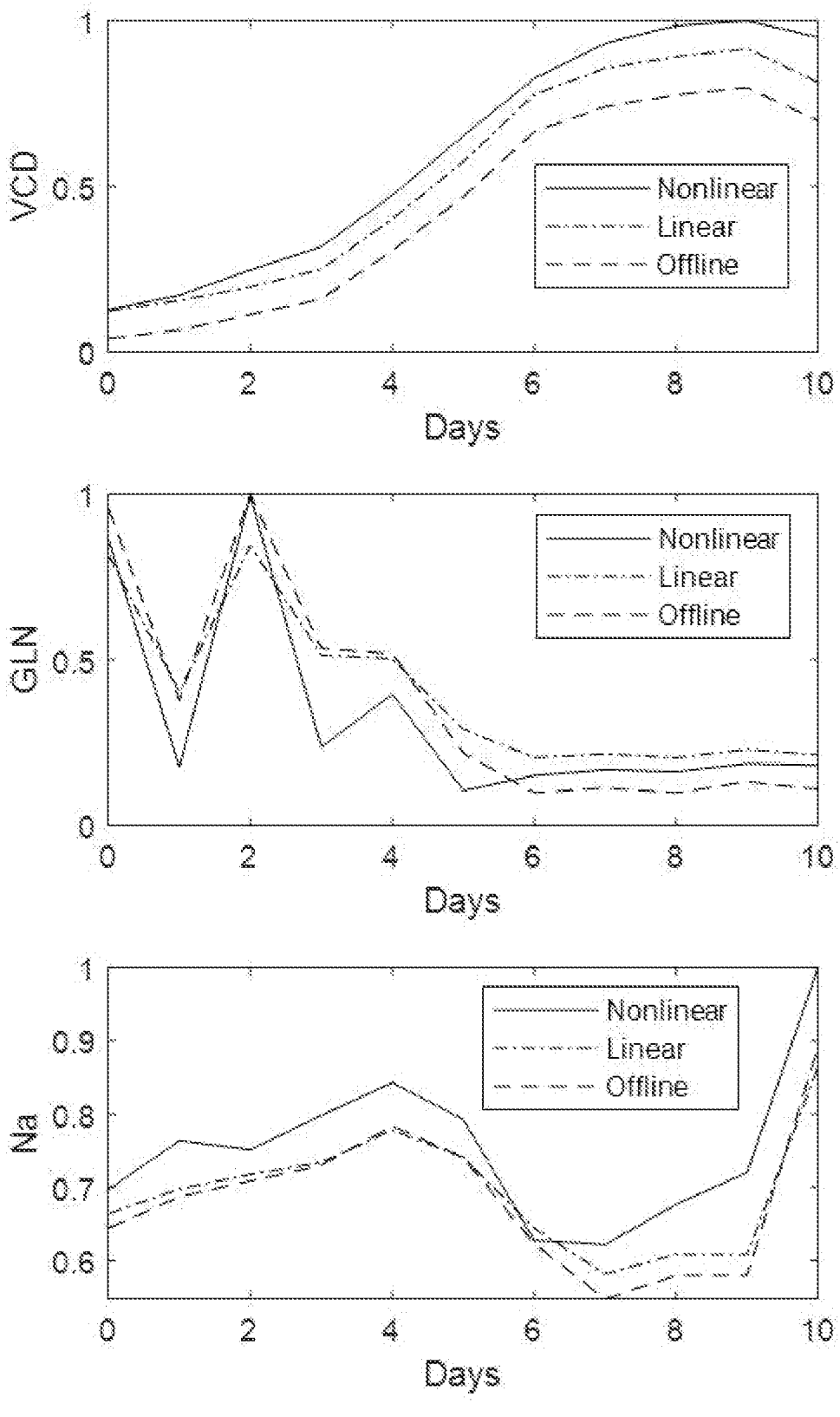
FIGS. 12A-C are normalized plots comparing prediction performance for various cell culture attributes when using a linear or nonlinear data-driven prediction model with a first principle model, for a third cell culture process.
Figure 12B:
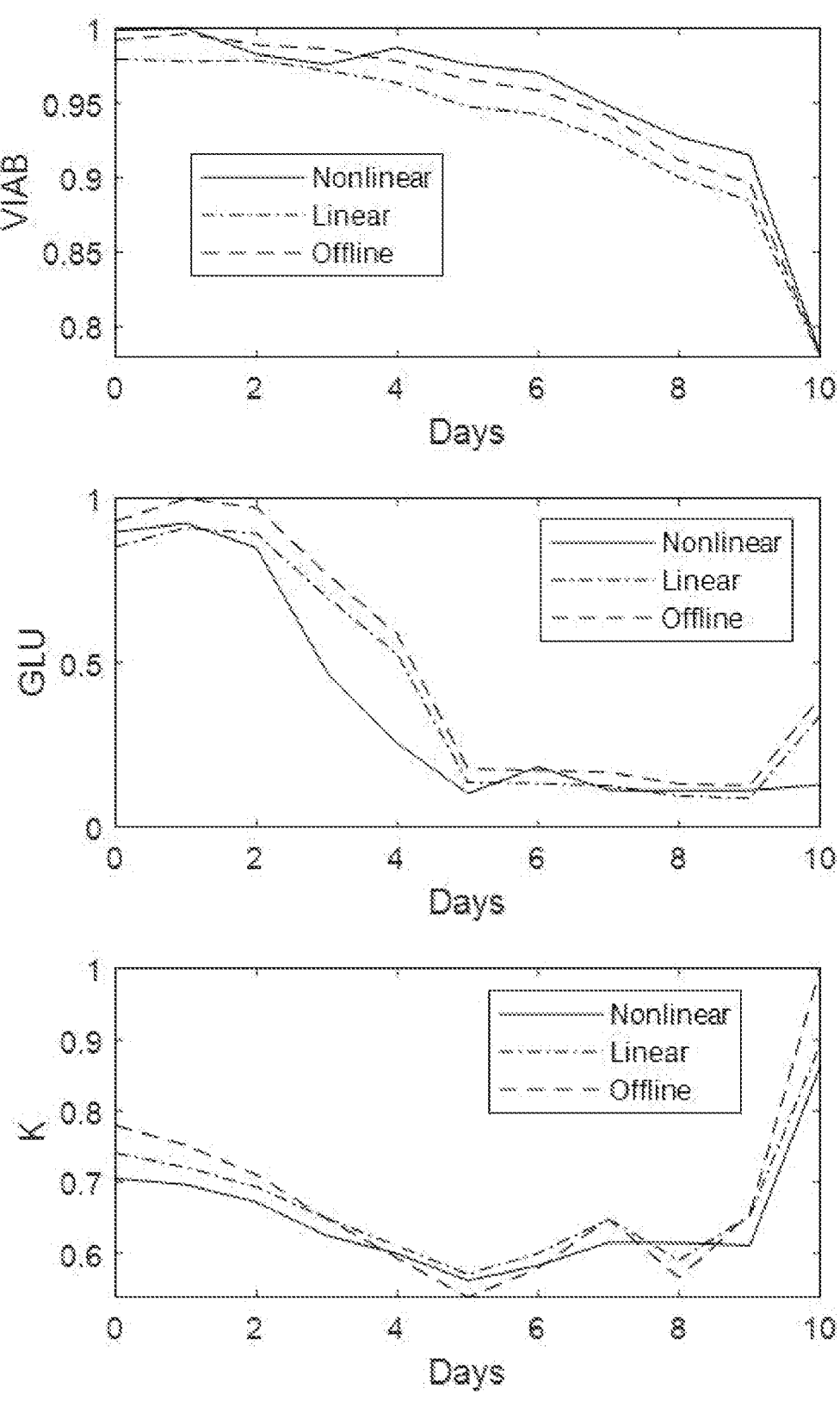
Figure 12C:
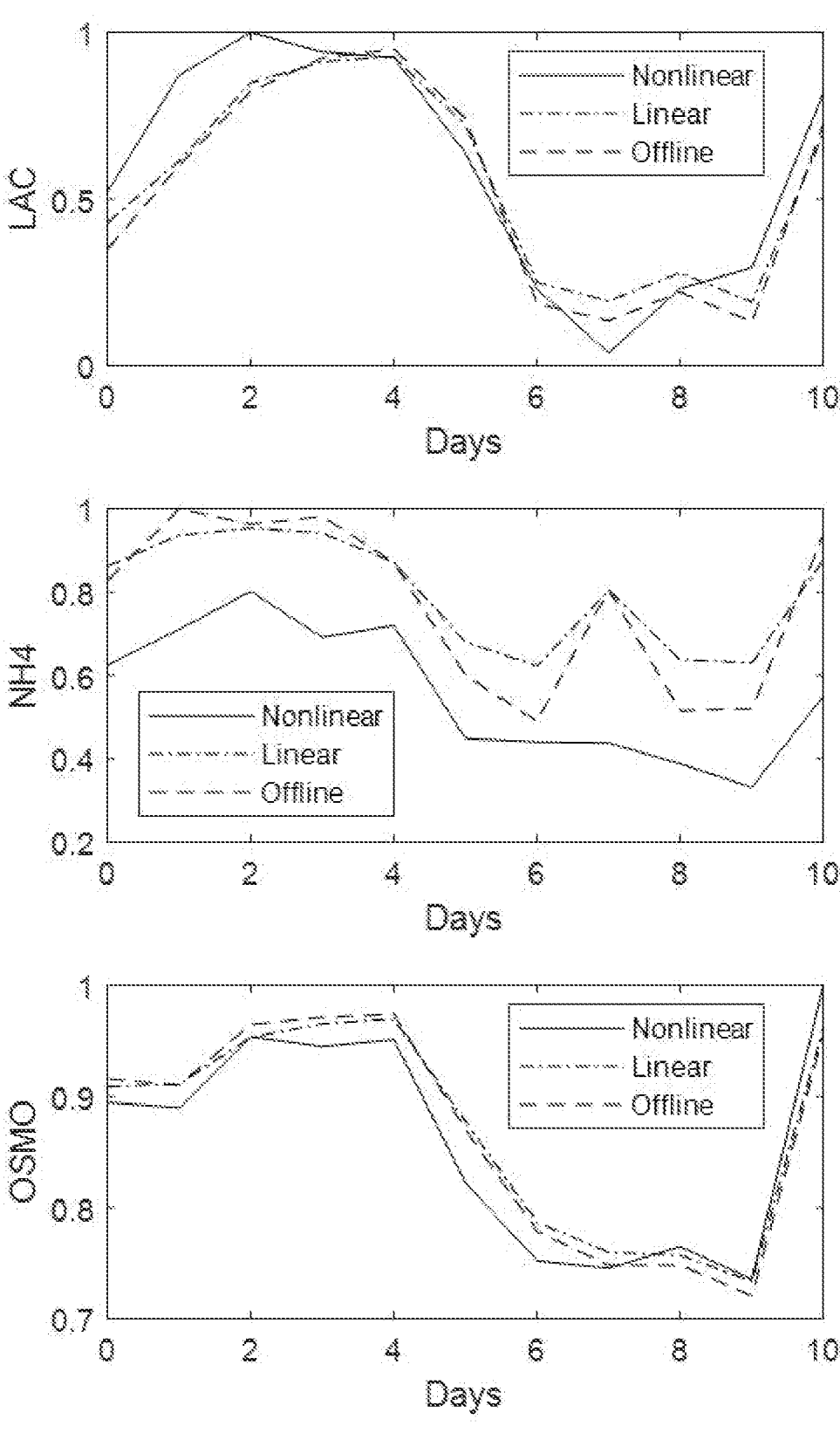
Figure 13A:
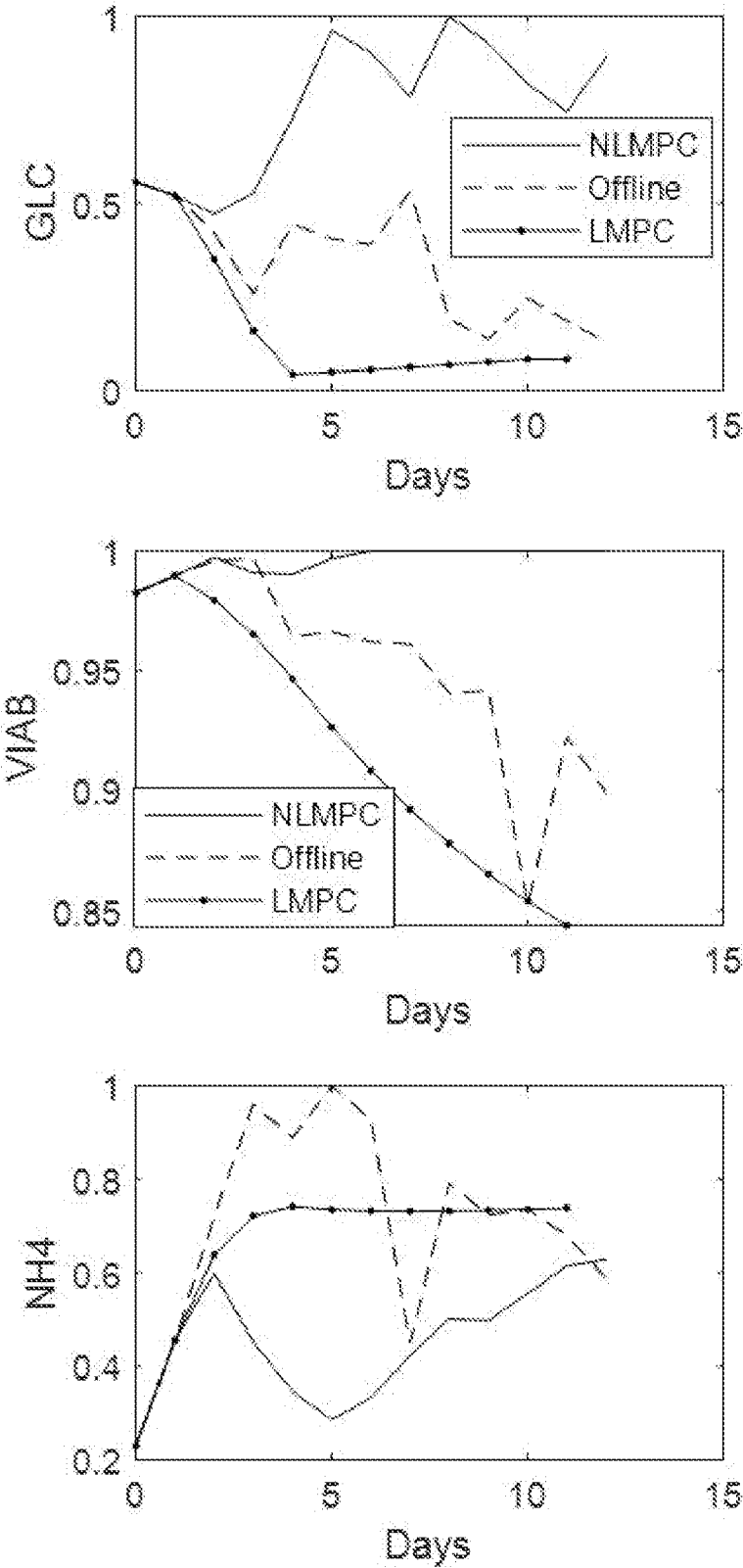
FIGS. 13A-D are normalized plots comparing model predictive controller performance for various cell culture attributes when using a linear or nonlinear data-driven prediction model with a first principle model, for the third cell culture process.
Figure 13B:
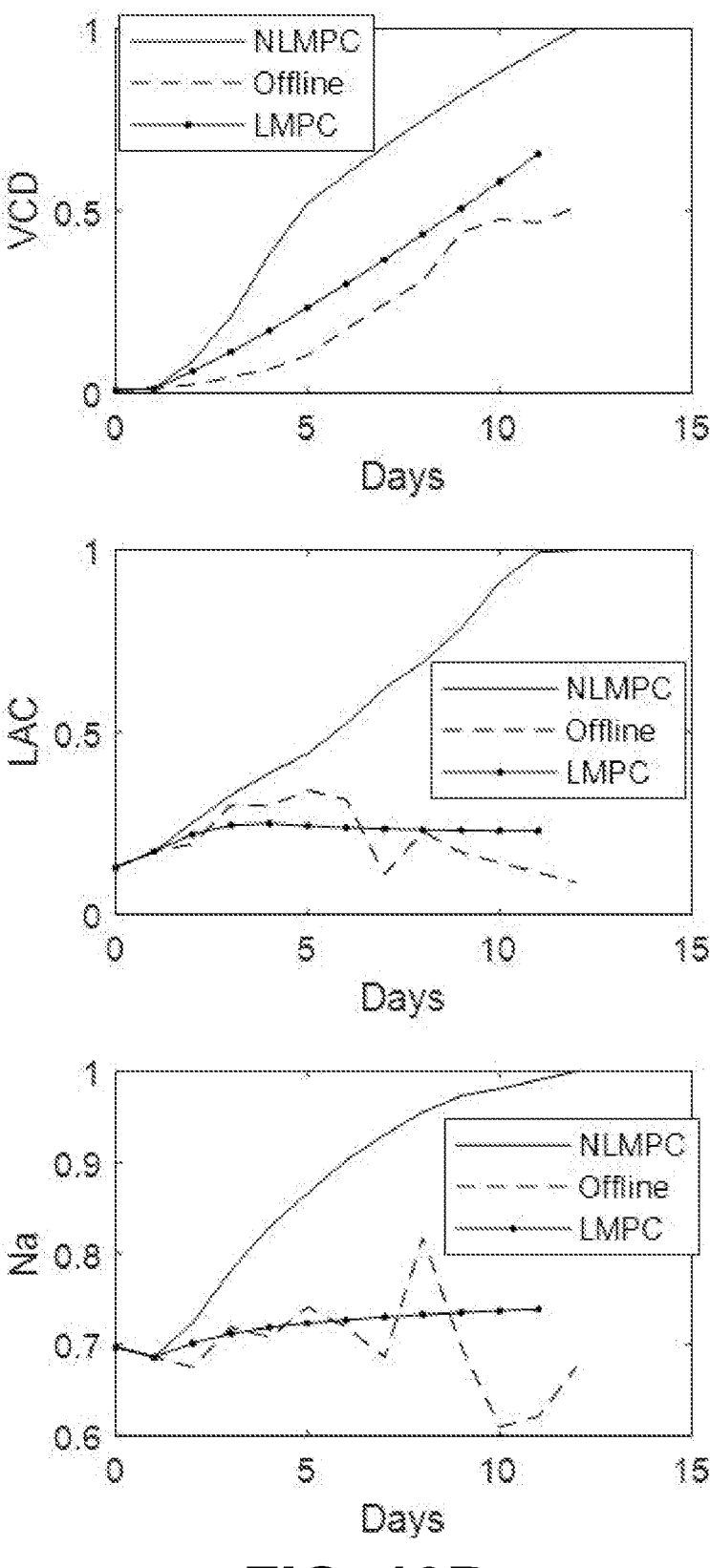
Figure 13C:
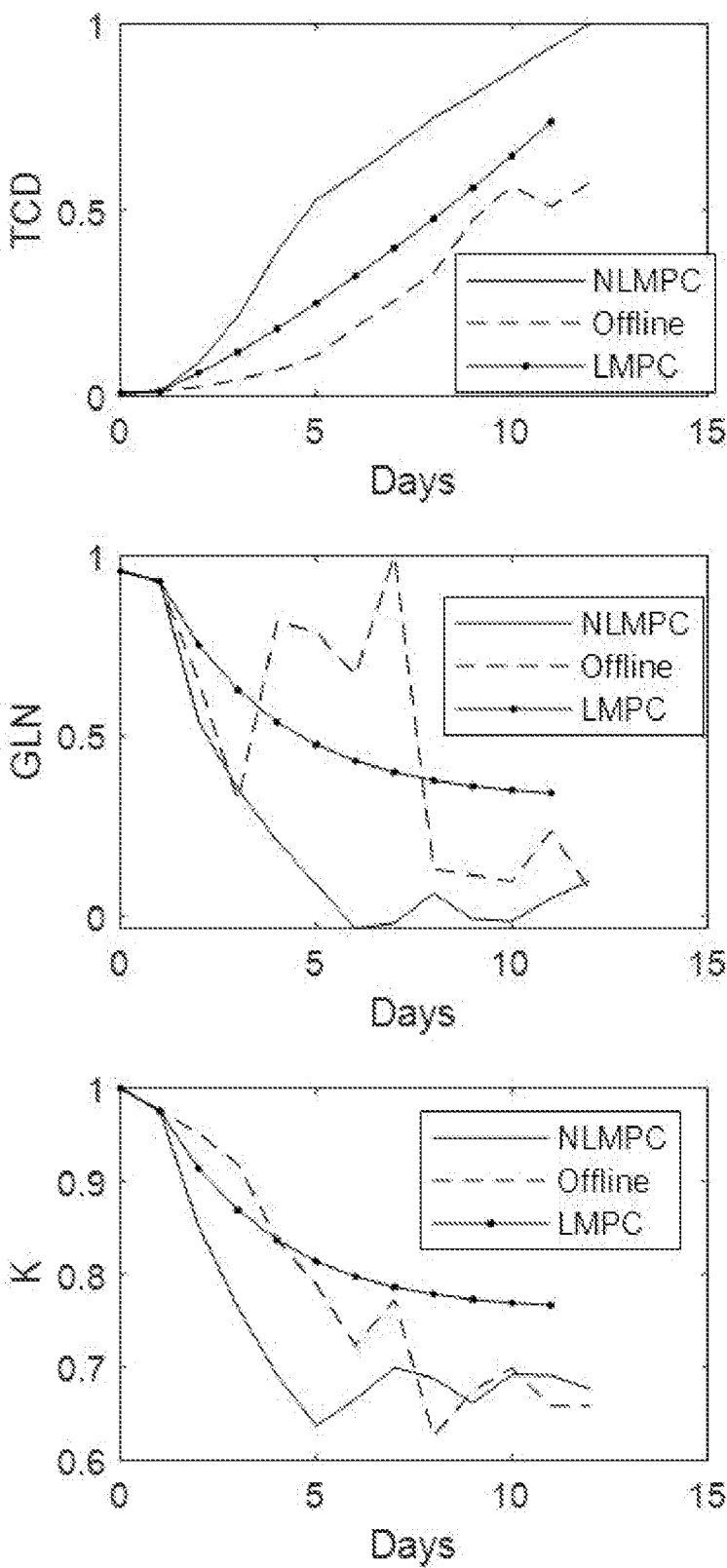
Figure 13D:
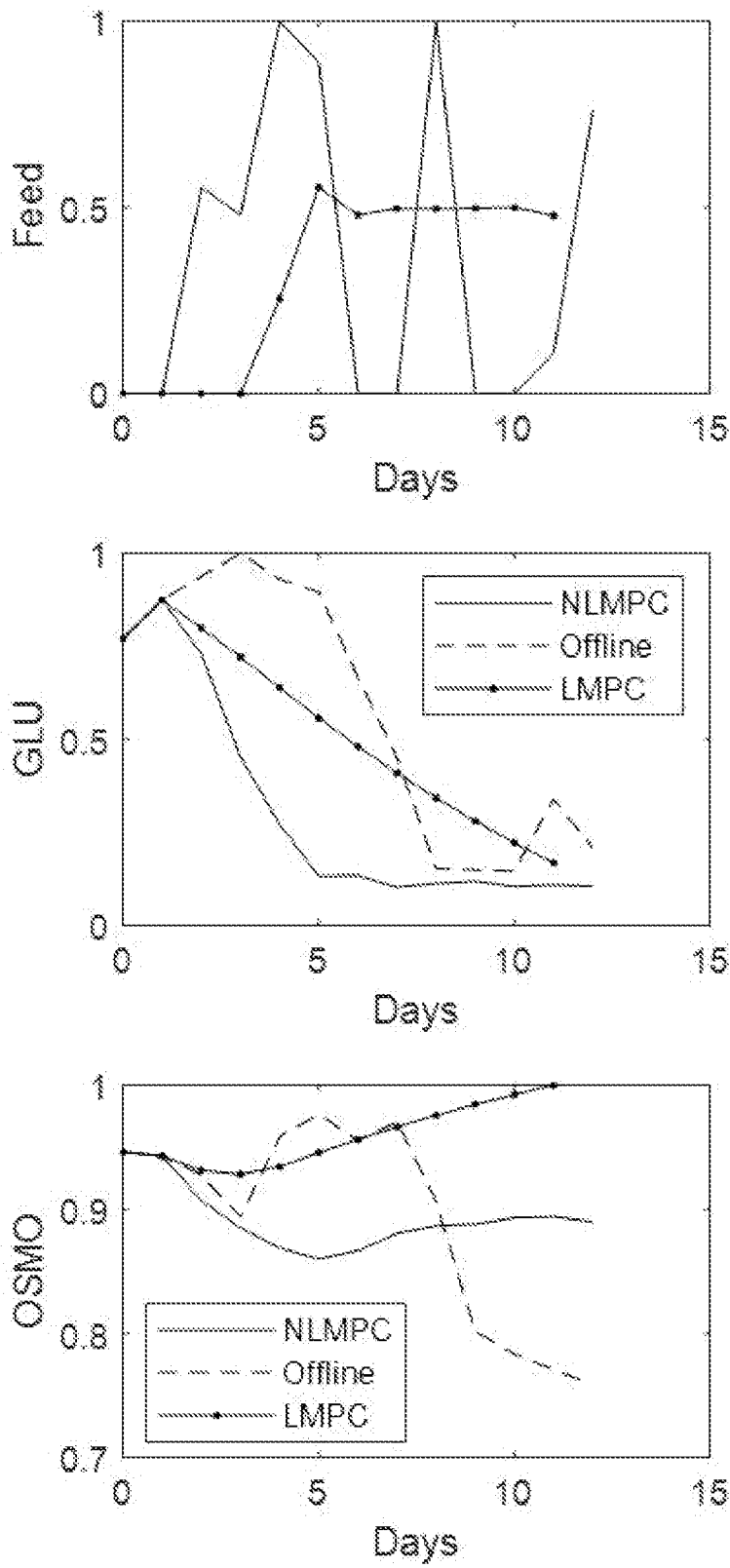

FIGS. 12A-C are normalized plots showing predictive performance of various embodiments of the MPC 142 for yet another cell culture process, different than the cell culture processes of FIGS. 6-9 and FIGS. 10-11. In particular, FIGS. 12A-C show predictive performance for embodiments in which the MPC 142 uses a linear regression model, a first-order nonlinear (feed-forward neural network) model, and a third-order nonlinear (feed-forward neural network) model, as compared to a system that did not use these predictive models (labeled "Offline" in FIGS. 12A-C).

FIGS. 13A-D are normalized plots showing performance of the MPC 142 for the same embodiment and same cell culture process reflected in FIGS. 12A-C, again with the "Offline" system results for comparison purposes. The normalized RMSE values for predictions made using the embodiments and cell culture process represented in FIGS. 12-13 are shown below in Table 3:

TABLE 3

| Cell Culture Attribute | Linear Model ($1^{st}$ Order) | Nonlinear Model ($3^{rd}$ Order) |
|---|---|---|
| VCD | 1.00 | 1.40 |
| TCD | 1.00 | 1.45 |
| VIAB | 1.00 | 0.73 |
| GLC | — | — |
| LAC | 1.00 | 0.63 |
| GLN | 1.00 | 0.53 |
| GLU | 1.00 | 1.00 |
| NH4 | 1.00 | 1.33 |
| Na | 1.00 | 0.65 |
| K | 1.00 | 0.89 |
| OSMO | 1.00 | 0.53 |

Table 4 compares the (normalized) resulting integrated VCD (iVCD) for a system that did not use hybrid predictive models (labeled "Offline" in Table 4), a linear regressor (first order), and a feed-forward neural network (3rd order) for the first cell culture process of FIGS. 6-9, the second cell culture process of FIGS. 10-11, and the third cell culture process of FIGS. 12-13:

TABLE 4

| Cell Culture Process | Offline | Linear Model (1st Order) | Nonlinear Model (3rd Order) |
|---|---|---|---|
| First | 1.00 | 1.02 | 0.86 |
| Second | 1.00 | 1.20 | 0.67 |
| Third | 1.00 | 1.21 | 2.42 |

On the whole, for MPC with a hybrid prediction model linear models provided better RMSE performance than nonlinear models. In addition, from an optimization point of view, the simpler structure of the linear model imposes less complexity for the optimal control, providing yet another benefit over the nonlinear approach. Specifically, a two-regressor (second order) linear model was found to have more accuracy and less complexity than other approaches, for at least some cell culture processes.

To further assess the performance of certain embodiments of the system 100, control experiments using conventional cell culture control methodologies were compared to experiments in which MPC with a hybrid predictive model was utilized for control of the glucose feed. In these experiments, samples/measurements were collected once per day, and (for the MPC with hybrid predictive model) the MPC calculated daily glucose feed strategies to optimize VCD. As a constraint on the optimization stage, the glucose feed rate was capped at 12 g/L, and a minimum feed rate of 3 g/L was also set but did not need to be enforced.

Figure 14:
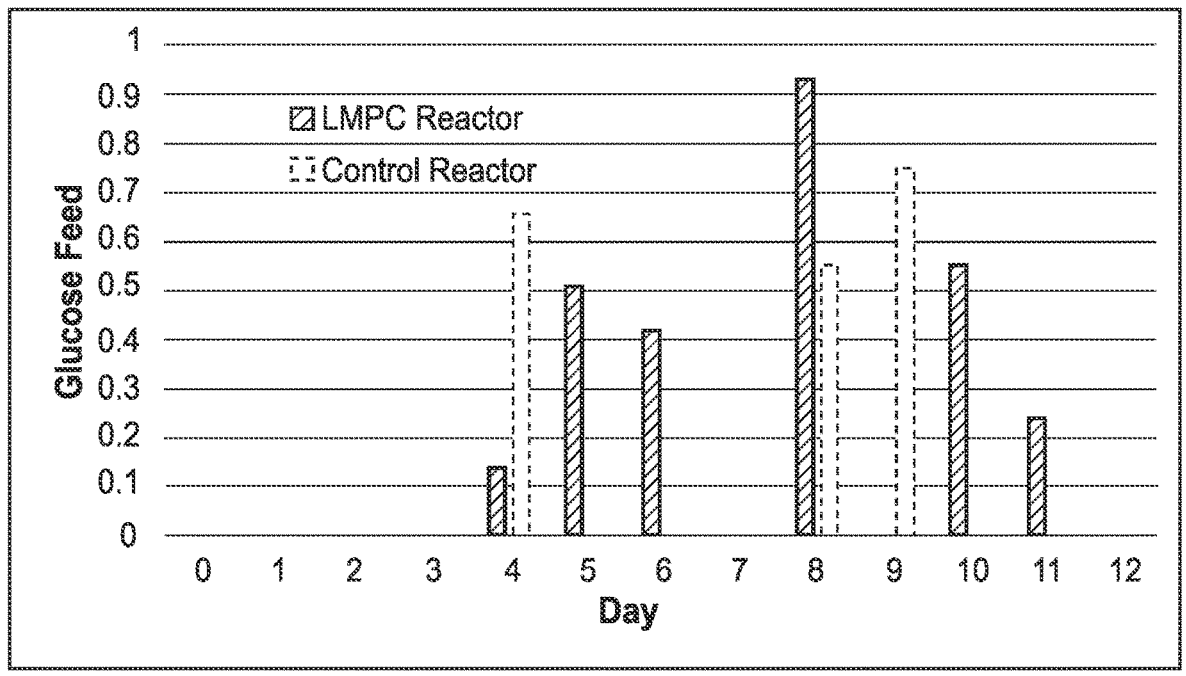
FIG. 14 is a normalized graph comparing glucose feed levels for processes with and without model predictive control and hybrid predictive modeling techniques disclosed herein.
Figure 15:
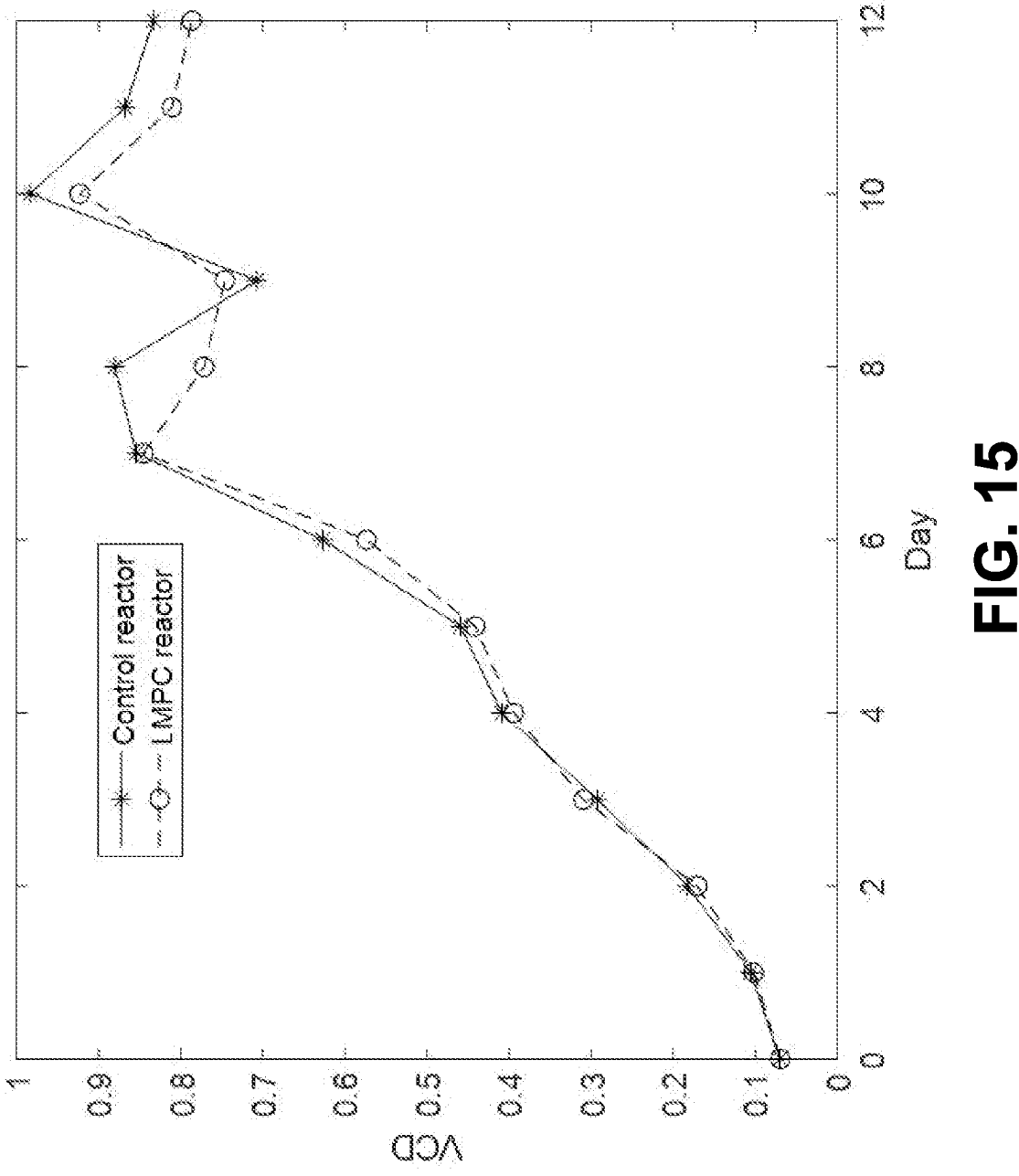
FIG. 15 is a normalized plot comparing viable cell density for processes with and without model predictive control and the hybrid predictive modeling techniques disclosed herein.
Figure 16A:
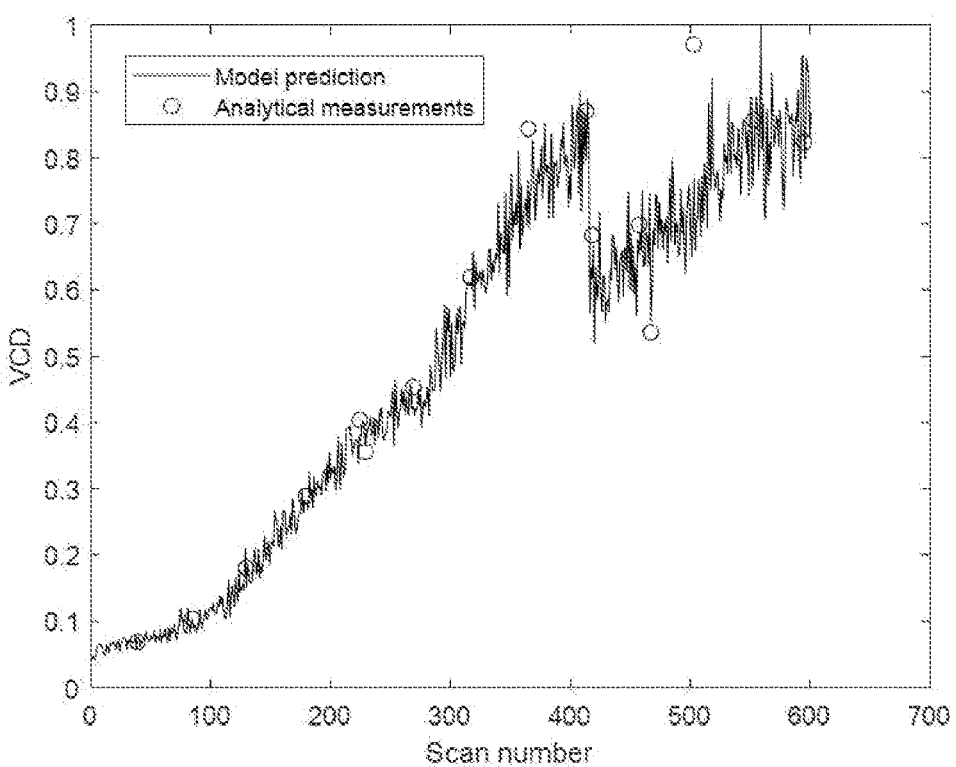
FIGS. 16A and 16B are normalized plots showing predicted versus measured Raman scan vectors for viable cell density, for systems without and with, respectively, model predictive control and hybrid predictive modeling techniques disclosed herein.
Figure 16B:
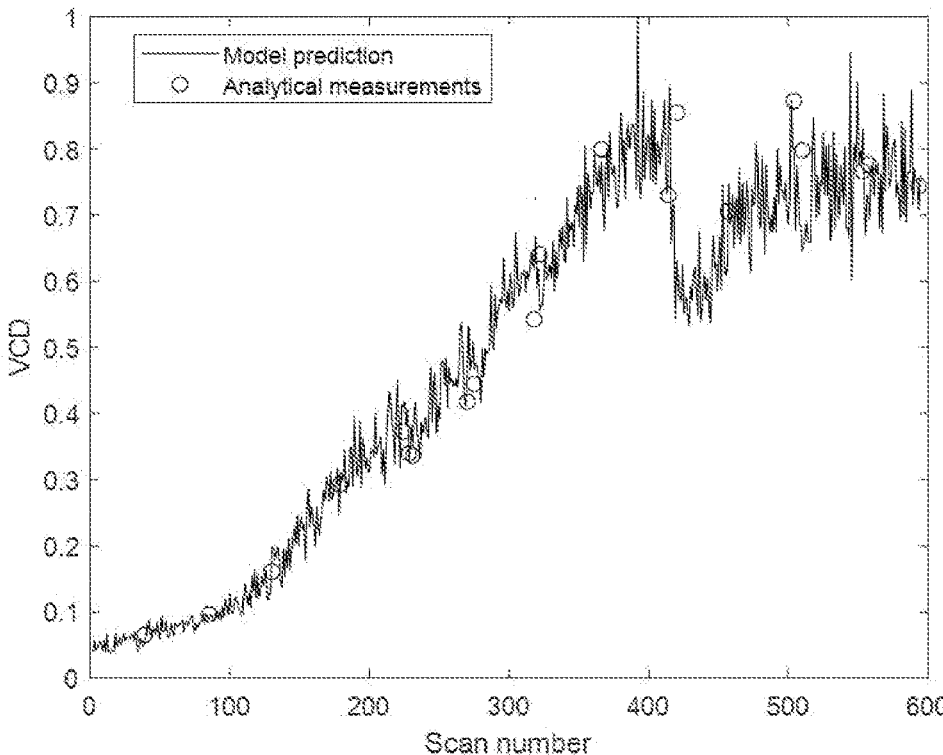

FIGS. 14 and 15 are normalized graphs comparing glucose feed levels and VCD, respectively, for these two experiments (labeled "MPC Reactor" for the embodiment of system 100, and "Control Reactor" for the conventional technique), and FIGS. 16A and 16B show predicted versus measured Raman scan vectors for VCD prediction (for the control reactor and the MPC reactor, respectively).

Figure 17:
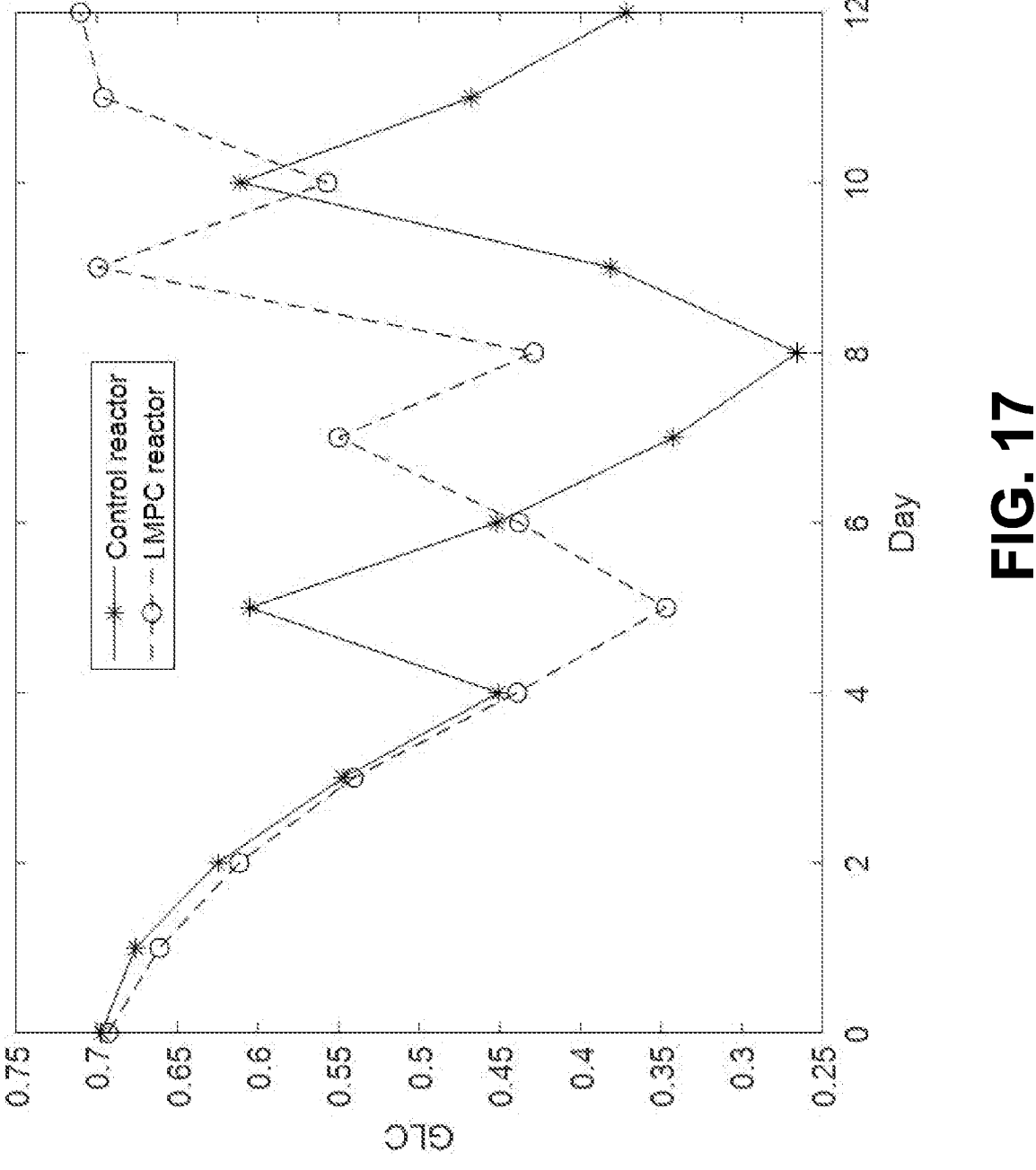
FIG. 17 is a normalized plot comparing glucose concentration for processes with and without model predictive control and the hybrid predictive modeling techniques disclosed herein.
Figure 18A:
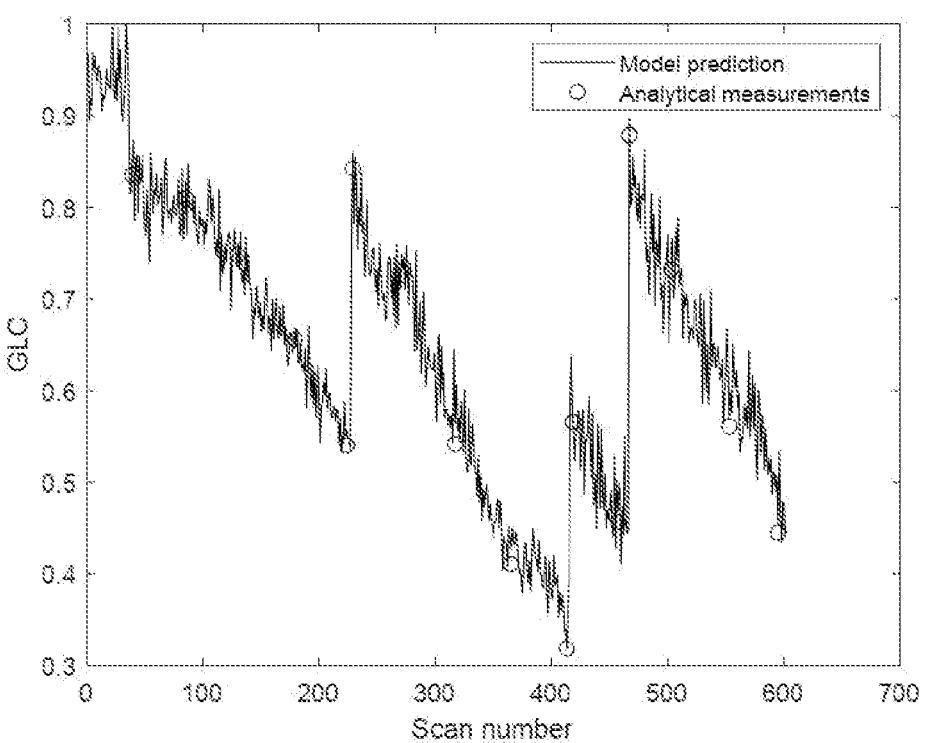
FIGS. 18A and 18B are normalized plots showing predicted versus measured Raman scan vectors for glucose concentration, for systems without and with, respectively, model predictive control and hybrid predictive modeling techniques disclosed herein.
Figure 18B:
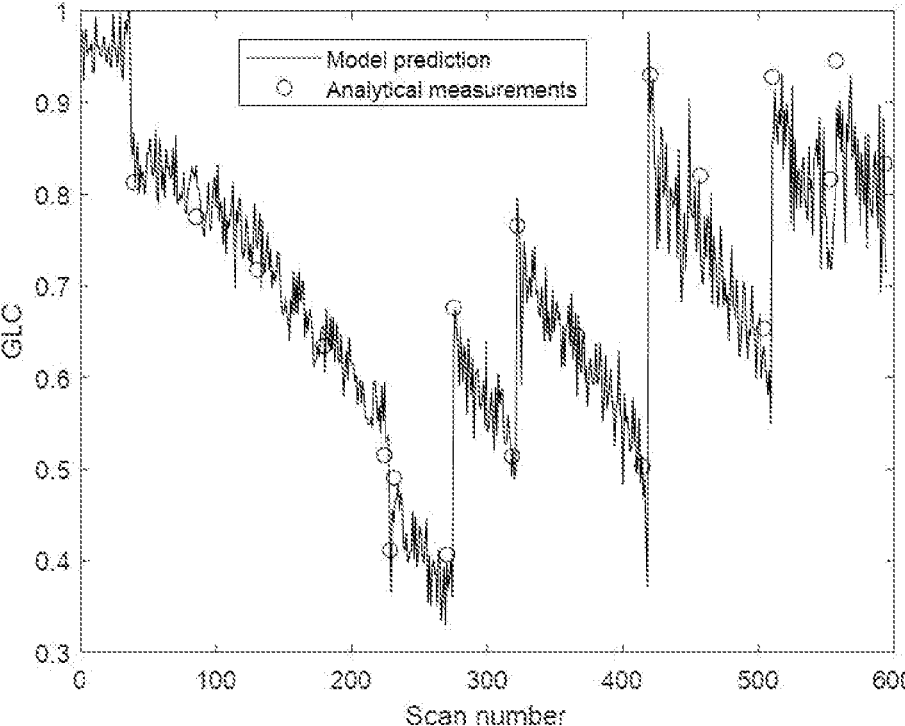
Figure 19:
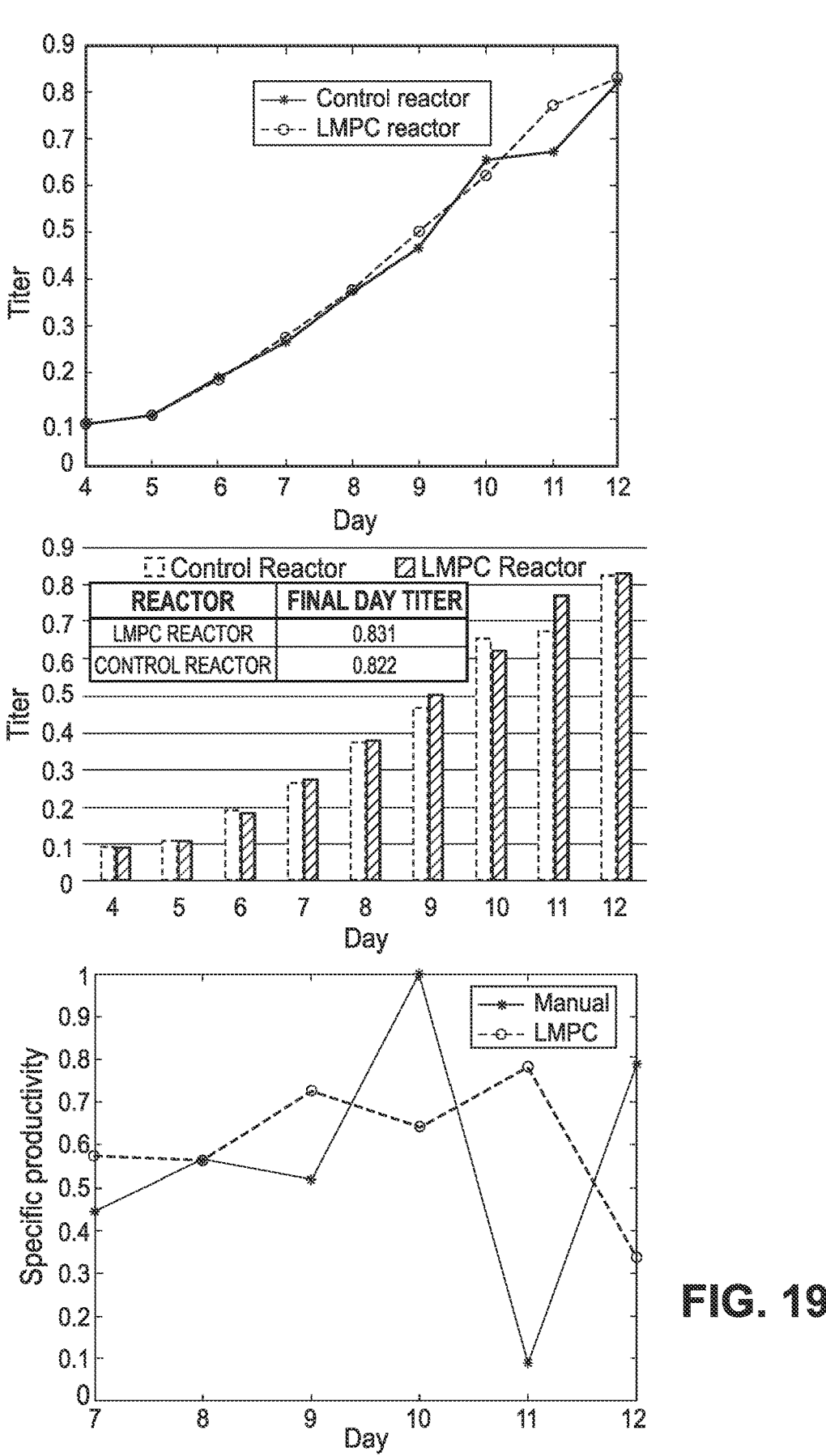
FIG. 19 includes normalized plots comparing titer and specific productivity for processes with and without model predictive control and the hybrid predictive modeling techniques disclosed herein.
Figure 20A:
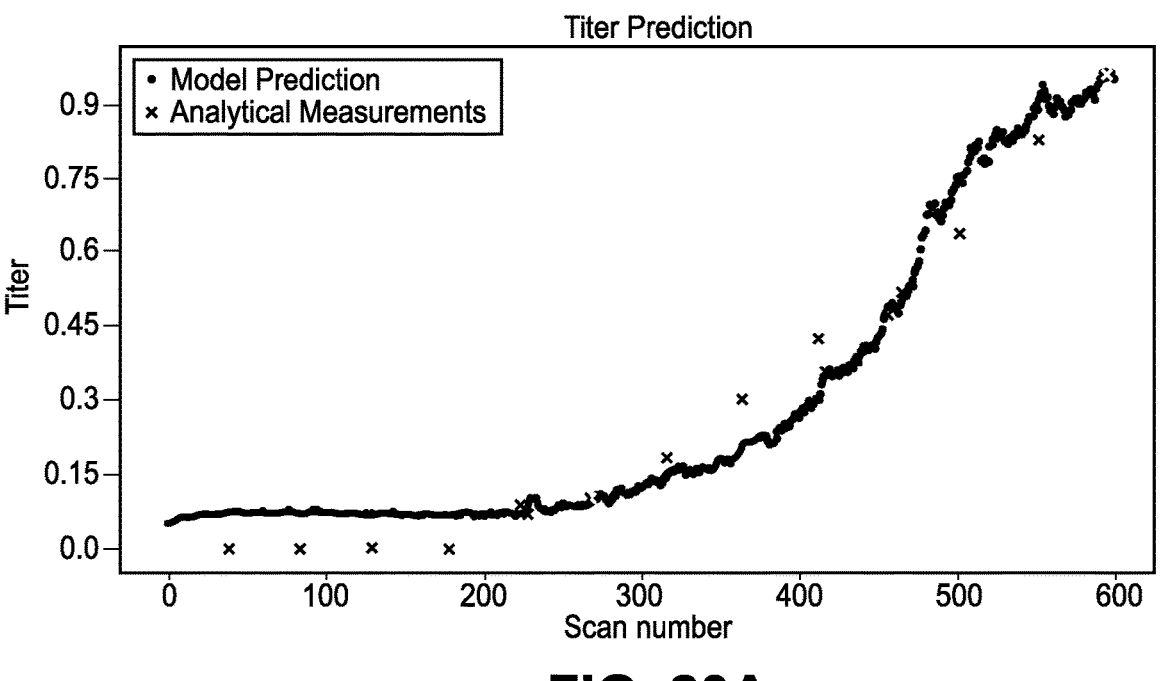
FIGS. 20A and 20B are normalized plots showing predicted versus measured Raman scan vectors for titer, for systems without and with, respectively, model predictive control and hybrid predictive modeling techniques disclosed herein.
Figure 20B:
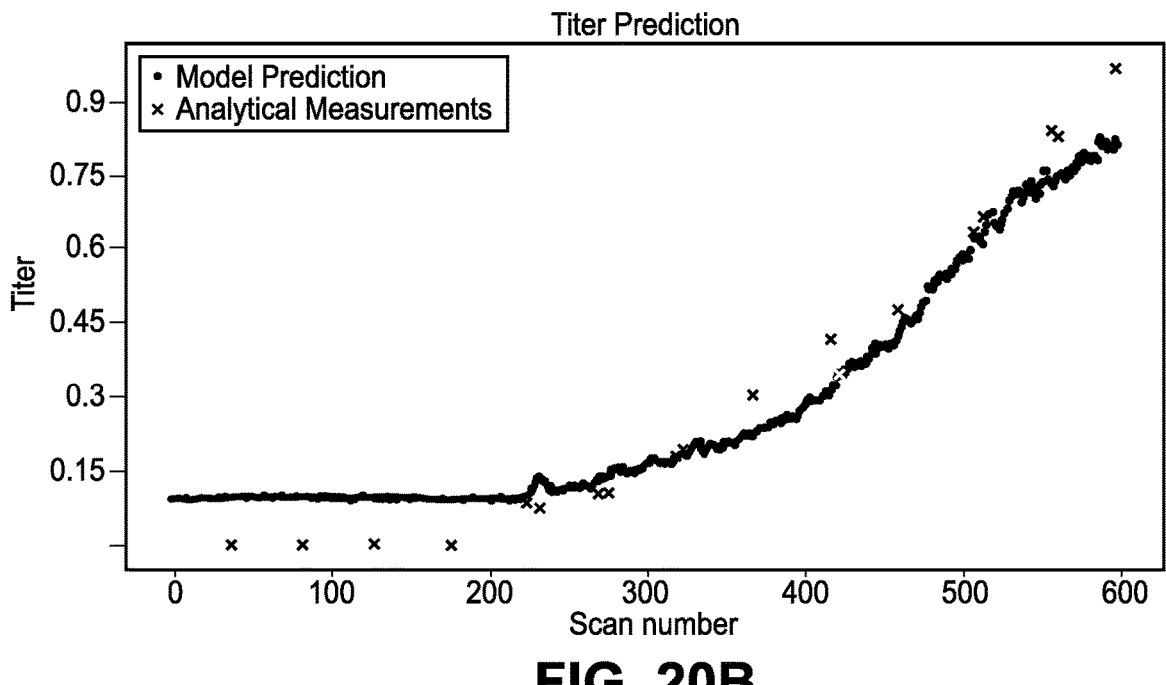

FIG. 17 is a normalized graph comparing glucose for the MPC and control experiments, and FIGS. 18A and 18B show predicted versus measured Raman scan vectors for glucose concentration prediction (for the control reactor and MPC reactor, respectively). FIG. 19 includes a comparison of titer (by process day, and final day titer) and specific productivity for a control system and a system implementing an embodiment of the MPC/hybrid predictive modeling techniques disclosed herein. FIGS. 20A and 20B show predicted versus measured Raman scan vectors for titer prediction (for the control bioreactor and MPC bioreactor, respectively).

Table 5 compares normalized SE-HPLC HMW, rCE LC+HC, and high mannose for the control bioreactor and the MPC/hybrid predictive modeling reactor, with typical acceptance criteria:

TABLE 5

| Reactor | SE-HPLC HMW | rCE LC + HC | High Mannose |
|---|---|---|---|
| Control | 0.8651 | 1.0021 | 0.5398 |
| MPC/Hybrid Prediction | 0.8635 | 1.0031 | 0.6311 |
| Acceptance Criteria | ≤1.0000 | ≥1.0000 | ≤1.0000 |

Table 6 compares normalized acidic peaks, basic peak 3, basic peaks, and main peak for the control bioreactor and the MPC/hybrid predictive modeling bioreactor, with typical acceptance criteria:

TABLE 6

| Reactor | Acidic Peaks | Basic Peak 3 | Basic Peaks | Main Peak |
|---|---|---|---|---|
| Control | 0.6630 | 0.7752 | 0.8441 | 1.0419 |
| MPC/Hybrid Prediction | 0.6327 | 0.6656 | 0.8026 | 1.0667 |
| Acceptance Criteria | 0.4028-1.000 | ≤1.000 | 0.2838-1.000 | ≥1.000 |

As seen in Table 6, the MPC/hybrid prediction bioreactor system had higher main peak and lower basic peak 3, which is favorable. For other parameters shown in Tables 5 and 6, performance for the MPC/hybrid prediction bioreactor system remained within acceptable ranges. As seen throughout FIGS. 6-20, MPC/hybrid prediction bioreactor systems incorporated Raman predictions for VCD, glucose, and titer. Linear MPC/hybrid prediction bioreactor systems generally led to more productive cells instead of more cell production. This is important when considering that the linear MPC/hybrid prediction bioreactor system underfed nutrients by approximately 2%. If the proper amount of nutrients had been fed, the VCD and therefore titer production would likely have been higher. The overall trend of the resulting VCD fluctuates over time and such fluctuation in VCD is expected as the high volume of bolus feed and cell growth would cause the cell density to drop or increase in the culture. Moreover, the linear MPC/hybrid prediction bioreactor system tries to maintain the glucose at a higher level by recommending more feed. Indeed, the linear MPC/hybrid prediction bioreactor system recommended feeding approximately 35% more glucose than the manual condition. However, the linear MPC/hybrid prediction bioreactor system did not feed glucose until a later day, which led to lower VCD for the linear MPC/hybrid prediction bioreactor system on subsequent days. On the other hand, the viability of the cells remained at the same level over the batch, which confirms the linear MPC/hybrid prediction bioreactor system had a healthy environment for the cell.

Further benefits may be obtained by using Gaussian process (GP) regression models. As noted above, uncertainty and scarcity of data can limit the effectiveness of data-driven modeling techniques. Gaussian process regression models can cope with intrinsic uncertainty of the data and perform in a satisfactory manner even with small datasets. In some embodiments, therefore, the data-driven model 152 in the MCP 142 is a GP model. This approach is referred to herein as a "GP-MPC technique" or simply "GP-MPC." The GP-MPC technique models the cell culture process in the bioreactor 102, and may be used to design and decide the best/optimal control action for the cell culture process. Using GP-MPC, the optimal metabolic path that the cells can take to achieve certain goals such as product quality and yield may be identified and enforced, while maintaining process constraints. By combining the superior titer production and the product quality benefits noted above (for main peak and basic peak 3), the linear MPC/hybrid prediction bioreactor system has the potential to reduce costs significantly (e.g., 5% or more).

GP models provide a probabilistic, non-parametric modelling approach for black-box identification of nonlinear dynamic systems. See, e.g., C. E. Rasmussen and C. K. Williams, Gaussian Processes for Machine Learning. The MIT Press: Cambridge USA, 2006. The GP model can predict the conditional posterior distribution of unseen data points conditioned on observed training points, and computes the mean of predicted points as linear combinations of training data with the weights of these linear combinations determined by the kernel distance from the training inputs. The GP model may be trained offline with historical data, as discussed above for the data-driven model 152.

In some embodiments where the data-driven model 152 is a GP model, one or more predictions of the GP model is/are passed to the glucose mass balance equation (e.g., the VCD[i+1] value in Equations 2 and 3). Glucose is not a manipulated variable, but rather is the main composition of the feed. The aim is to maximize VCD while maintaining the glucose concentration within a specific range in the bioreactor 102.

Combining GP with MPC gives rise to multiple challenges, such as the cubical increase of the computational load with the number of training data points. This also increases the overall computations required to solve the resulting optimal control problem. Optimization requires the Jacobian to evaluate the optimal direction and check for the optimality conditions. The GP model can act as a black-box for the optimization problem, without any explicit mathematical expressions. In some embodiments, the optimization problem (i.e., the optimizer 146) calculates the Jacobian using numerical methods such as finite differences. Computing finite difference approximations may require many function evaluations, which slows down the optimization process. To speed up the calculation process, the hybrid prediction unit 144 may evaluate the Jacobian function (matrix) and pass the Jacobian function to the optimization problem (i.e., to the optimizer 146). As discussed above, the GP model gives a posterior distribution over functions mapping input to output. The Gaussian process can be differentiated to obtain a distribution over the gradient. If the covariance function is differentiable, the hybrid prediction unit 144 can calculate the gradients in a closed form. Therefore, the need for finite difference calculations is alleviated. Correspondingly, during the training and tuning of the GP model, the hybrid prediction unit 144 may use covariance functions that are differentiable (e.g., a squared exponential covariance function or other suitable function).

The GP-MPC technique can result in a different feeding strategy as compared to conventional feeding strategies.

Figure 21:
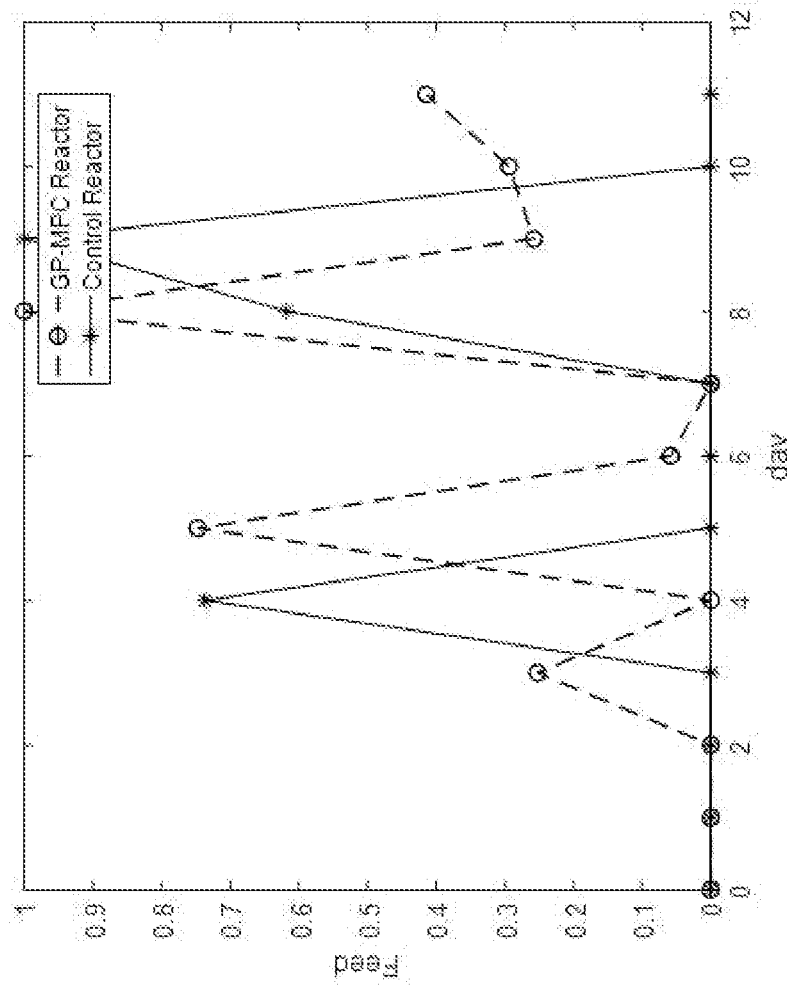
FIG. 21 is a normalized plot comparing glucose feed rates for processes with and without model predictive control and the hybrid predictive modeling techniques disclosed herein, with the use of Gaussian process modeling for the model predictive control.
Figure 22:
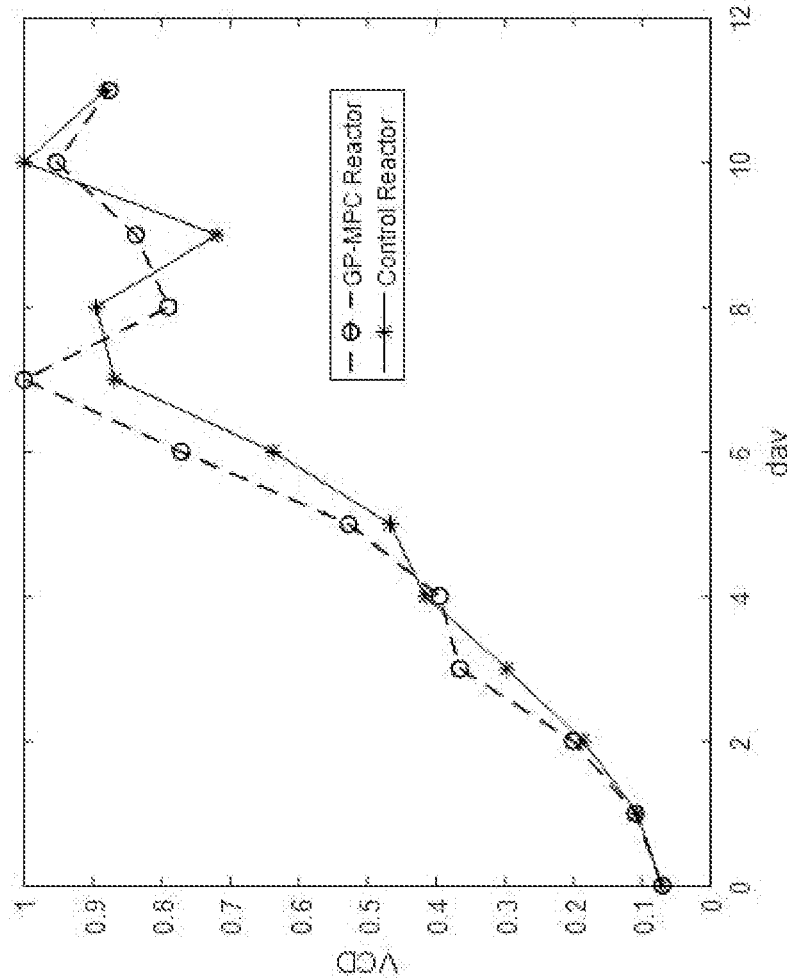
FIG. 22 is a normalized plot comparing viable cell densities for processes with and without model predictive control and the hybrid predictive modeling techniques disclosed herein, with the use of Gaussian process modeling for the model predictive control.

Instead of feeding a bioreactor in only three days, for example, the GP-MPC technique may suggest different feed volumes throughout the entire span of the cell culture process. FIG. 21 is a normalized plot comparing glucose feed rates for processes with a GP-MPC technique, and without ("control data" in FIG. 21). The different feeding strategy translates into a slightly higher integral viable cell density (iVCD), as seen in FIG. 22. The final titer concentration is highly correlated to some of the attributes in the process, such as VCD and osmolality. Targets may be set for all of these attributes, and optimization may be formulated to meet those targets. Several weights can be assigned to the attributes in the objective function to change the driving factors of the controller based on the need of a given manufacturing site, for example. The reasoning behind choosing certain metabolite-related attributes instead of titer to define the objective function is that the metabolite-related measurements (e.g., VCD) are easily accessible at every sampling interval, while accurate titer estimations are typically not readily available.

Figure 23:
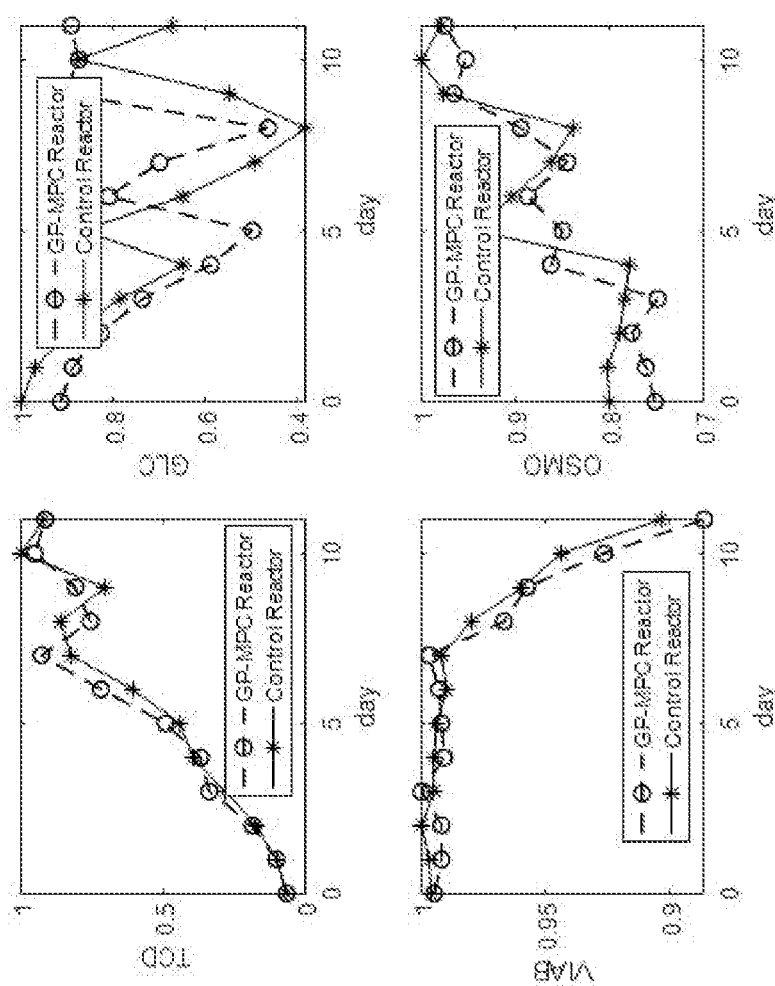
FIG. 23 shows normalized plots comparing total cell density, glucose concentration, viability, and osmolality for processes with and without model predictive control and the hybrid predictive modeling techniques disclosed herein, with the use of Gaussian process modeling for the model predictive control.
Figure 24:
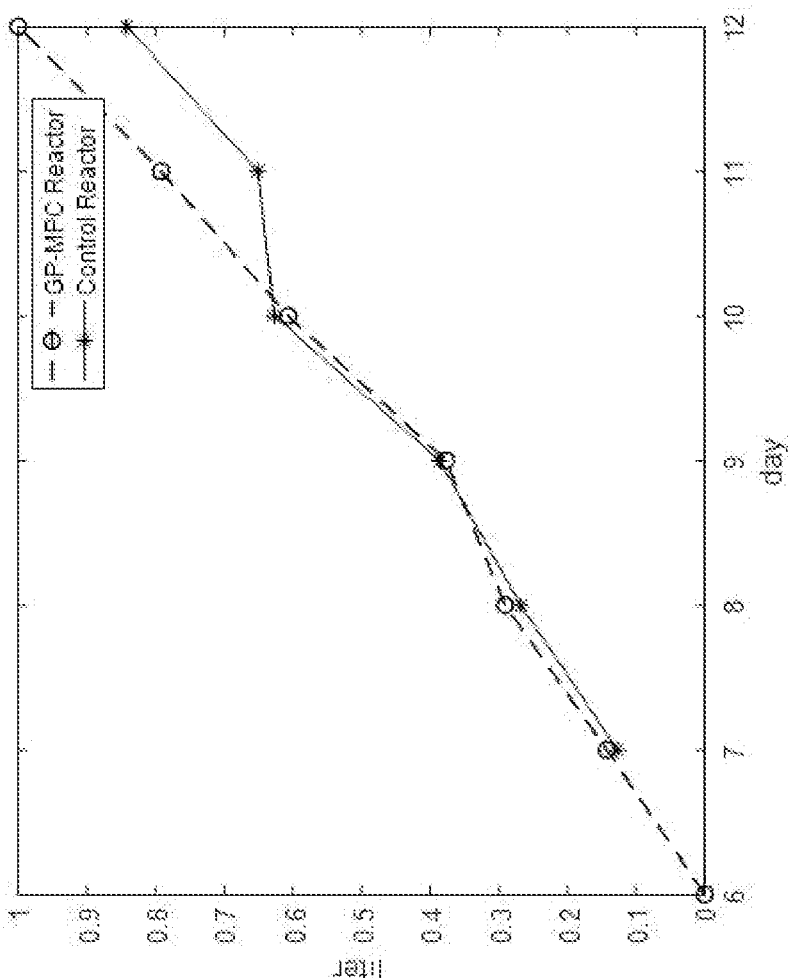
FIG. 24 is a normalized plot comparing titer for processes with and without model predictive control and the hybrid predictive modeling techniques disclosed herein, with the use of Gaussian process modeling for the model predictive control.

In addition to the VCD, the trend for certain other metabolite-related attributes, and their comparison to control data, are shown in FIG. 23. All of the attributes remain in their desired ranges with GP-MPC, and follow a reasonable trend during the process. Titer values for control data and the GP-MPC technique are compared in FIG. 24. Advantageously, the GP-MPC technique results in 15% higher titer compared to the control data at the end of the process.

In summary, the GP-MPC technique enables observation and maintenance of a cell culture process at a consistent state to achieve various objectives, depending on the needs of a given manufacturing site. The designed system may ensure minimal variability to meet quality targets, while optimizing for higher yields by making the necessary adjustments in real-time. The Gaussian processes can highlight regions of the process where prediction quality is poor, due to the lack of data or its complexity, by indicating the higher variance around the predicted mean. This information can be used to modify the process constraints, to enable handling of non-convexity and nonlinearity in specific regions.

FIG. 25 is a flow diagram of an example method 2500 of controlling a cell culture process using hybrid predictive modeling in a model predictive controller. The method 2500 may be implemented by a system such as the system 100 of FIG. 1 (e.g., by the processing hardware 120 executing instructions of the CCPC application 130). The method 2500 may be repeated (e.g., in real-time) for multiple time intervals (e.g., each of multiple days) during the cell culture process, e.g., once per time interval (once per day, or once per hour, etc.), with the time intervals (1) having fixed or variable lengths/durations, and (2) being all of the same length/duration or including two or more different lengths/durations.

At block 2502, current values of cell culture attributes associated with a cell culture (e.g., in a bioreactor such as bioreactor 102) are obtained. Block 2502 may include receiving the current values from another device or system (e.g., from analytical instrument(s) 104), directly measuring some or all of the values (e.g., by analytical instrument(s) 104), and/or inferring or predicting some or all of the values (e.g., based on Raman spectroscopy measurements/scan vectors generated by analytical instrument(s) 104), for example. The cell culture attributes for which values are obtained may include one or more metabolite concentrations (e.g., glucose, lactate, sodium, ammonium, glutamine, glutamate, potassium), VCD, TCD, viability, osmolality, and/or one or more other attributes of the cell culture.

At block 2504, a control value for a physical input to the cell culture process is generated. The physical input may be a glucose feed rate provided by a glucose pump, for example, or another type of physical input (e.g., an input provided by a heating or cooling device if temperature is controlled, or an impeller speed, etc.). Block 2504 includes predicting, at block 2506, based on the current values obtained at block 2502, future values of the cell culture attributes. Block 2506 may include predicting a value for each time interval of a prediction horizon, for example.

The predictions may be based on the most recent measurements of cell culture attributes (i.e., the "current" values obtained at block 2502) and possibly one or more earlier measured values for some or all of those attributes. Block 2506 includes using one or more data-driven models (e.g., data-driven model 152) to predict future values of a first one or more attributes of the cell culture attributes, and using one or more first principle models (e.g., first principle model 150) to predict future values of a second one or more attributes of the cell culture attributes. For example, the first attribute(s) may include VCD, TCD, viability, osmolality, lactate concentration, glutamine concentration, glutamate concentration, ammonium concentration, sodium concentration, and/or potassium concentration, and/or the second attribute(s) may include a glucose concentration of the cell culture. In some embodiments, block 2506 includes applying a predicted future value of a first attribute of the first one or more attributes (e.g., a future VCD value as predicted by one of the data-driven model(s)) as an input to at least one of the first principle model(s). The first principle model(s) may include a mass balance model such as that represented by Equations 2 and 3, for example. The data-driven model(s) may include any one or more of the data-driven model types discussed above. For example, the data-driven model(s) may include a linear regression model of any suitable order, a feed-forward neural network or other nonlinear model of any suitable order, a probabilistic regression model such as a Gaussian process model, and so on.

Block 2504 also includes determining, at block 2508, the control value by optimizing (e.g., minimizing) an objective function subject to the future values predicted at block 2506 and any other constraint(s) (e.g., minimum and maximum glucose feed values). The objective function may have the form of Equations 1A and 1B, for example. Block 2508 may include determining a control value for each time interval of a control horizon, for example.

At block 2510, a physical input to the cell culture process is controlled using the control value (e.g., using the first/earliest control value of a set of control values corresponding to a control horizon). For example, block 2510 may include generating a control signal (e.g., a message compliant with the protocol of the input device 106), and sending the control signal to the appropriate device (e.g., to input device 106). As a more specific example, block 2510 may include controlling a glucose feed rate by generating a control signal (e.g., a message/command specifying a setpoint) and sending the signal to a glucose pump.

Additional considerations pertaining to this disclosure will now be addressed.

Some of the figures described herein illustrate example block diagrams having one or more functional components. It will be understood that such block diagrams are for illustrative purposes and the devices described and shown may have additional, fewer, or alternate components than those illustrated. Additionally, in various embodiments, the components (as well as the functionality provided by the respective components) may be associated with or otherwise integrated as part of any suitable components.

Embodiments of the disclosure relate to a non-transitory computer-readable storage medium having computer code thereon for performing various computer-implemented operations. The term "computer-readable storage medium" is used herein to include any medium that is capable of storing or encoding a sequence of instructions or computer codes for performing the operations, methodologies, and techniques described herein. The media and computer code may be those specially designed and constructed for the purposes of the embodiments of the disclosure, or they may be of the kind well known and available to those having skill in the computer software arts. Examples of computer-readable storage media include, but are not limited to: magnetic media such as hard disks, floppy disks, and magnetic tape; optical media such as CD-ROMs and holographic devices; magneto-optical media such as optical disks; and hardware devices that are specially configured to store and execute program code, such as ASICs, programmable logic devices ("PLDs"), and ROM and RAM devices.

Examples of computer code include machine code, such as produced by a compiler, and files containing higher-level code that are executed by a computer using an interpreter or a compiler. For example, an embodiment of the disclosure may be implemented using Java, C++, or other object-oriented programming language and development tools. Additional examples of computer code include encrypted code and compressed code. Moreover, an embodiment of the disclosure may be downloaded as a computer program product, which may be transferred from a remote computer (e.g., a server computer) to a requesting computer (e.g., a client computer or a different server computer) via a transmission channel. Another embodiment of the disclosure may be implemented in hardwired circuitry in place of, or in combination with, machine-executable software instructions.

As used herein, the singular terms "a," "an," and "the" may include plural referents, unless the context clearly dictates otherwise.

As used herein, the terms "approximately," "substantially," "substantial" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, two numerical values can be deemed to be "substantially" the same if a difference between the values is less than or equal to ±10% of an average of the values, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified.

While the present disclosure has been described and illustrated with reference to specific embodiments thereof, these descriptions and illustrations do not limit the present disclosure. It should be understood by those skilled in the art that various changes may be made and equivalents may be substituted without departing from the true spirit and scope of the present disclosure as defined by the appended claims. The illustrations are not necessarily drawn to scale. There may be distinctions between the artistic renditions in the present disclosure and the actual apparatus due to manufacturing processes, tolerances and/or other reasons. There may be other embodiments of the present disclosure which are not specifically illustrated. The specification (other than the claims) and drawings are to be regarded as illustrative rather than restrictive. Modifications may be made to adapt a particular situation, material, composition of matter, technique, or process to the objective, spirit and scope of the present disclosure. All such modifications are intended to be within the scope of the claims appended hereto. While the techniques disclosed herein have been described with reference to particular operations performed in a particular order, it will be understood that these operations may be combined, sub-divided, or re-ordered to form an equivalent technique without departing from the teachings of the present disclosure. Accordingly, unless specifically indicated herein, the order and grouping of the operations are not limitations of the present disclosure.

What is claimed:

1. A method of controlling a cell culture process using hybrid predictive modeling in a model predictive controller, the method comprising, for a plurality of time intervals during the cell culture process:

obtaining current values of cell culture attributes associated with a cell culture;

generating, by processing hardware, a control value for a physical input to the cell culture process, wherein generating the control value includes predicting, based on the current values, future values of the cell culture attributes, at least by (i) using one or more data-driven models to predict future values of a first one or more attributes of the cell culture attributes, and (ii) using one or more first principle models to predict future values of a second one or more attributes of the cell culture attributes, and determining the control value by optimizing an objective function subject to the predicted future values of the cell culture attributes; and controlling, by the processing hardware and using the control value, the physical input to the cell culture process.

2. The method of claim 1, wherein:

the physical input to the cell culture process is a glucose feed rate;

the second one or more attributes include a glucose concentration of the cell culture; and controlling the physical input to the cell culture process includes controlling the glucose feed rate by sending a control signal to a glucose pump.

3. The method of claim 2, wherein the first one or more attributes include viable cell density, total cell density, viability, osmolality, lactate concentration, glutamine concentration, glutamate concentration, ammonium concentration, sodium concentration, and/or potassium concentration.

4. The method of claim 1, wherein using the one or more first principle models to predict the future values of the second one or more attributes includes applying a predicted future value of a first attribute of the first one or more attributes as an input to at least one of the one or more first principle models.

5. The method of claim 4, wherein the first attribute is viable cell density.

6. The method of claim 1, wherein the one or more data-driven models include a linear regression model or a probabilistic regression model.

7. The method of claim 6, wherein the one or more data-driven models include a Gaussian process regression model.

8. The method of claim 1, wherein the one or more data-driven models include a feed-forward neural network.

9. The method of claim 1, wherein predicting the future values of the cell culture attributes is based on (i) the current values of the cell culture attributes and (ii) one or more earlier values of the cell culture attributes.

10. The method of claim 1, wherein using the one or more first principle models to predict the future values of the second one or more attributes includes applying one or more previous control values as inputs to the one or more first principle models.

11. One or more non-transitory, computer-readable media storing instructions that, when executed by processing hardware of a computing system and for a plurality of time intervals during a cell culture process, cause the computing system to:

obtain current values of cell culture attributes associated with a cell culture;

generate a control value for a physical input to the cell culture process, wherein generating the control value includes predicting, based on the current values, future values of the cell culture attributes, at least by (i) using one or more data-driven models to predict future values of a first one or more attributes of the cell culture attributes, and (ii) using one or more first principle models to predict future values of a second one or more attributes of the cell culture attributes, and determining the control value by optimizing an objective function subject to the predicted future values of the cell culture attributes; and control the physical input to the cell culture process using the control value.

12. The one or more non-transitory, computer-readable media of claim 11, wherein:

the physical input to the cell culture process is a glucose feed rate;

the second one or more attributes include a glucose concentration of the cell culture; and controlling the physical input to the cell culture process includes controlling the glucose feed rate by sending a control signal to a glucose pump.

13. The one or more non-transitory, computer-readable media of claim 11, wherein the first one or more attributes include viable cell density, total cell density, viability, osmolality, lactate concentration, glutamine concentration, glutamate concentration, ammonium concentration, sodium concentration, and/or potassium concentration.

14. The one or more non-transitory, computer-readable media of claim 11, wherein using the one or more first principle models to predict the future values of the second one or more attributes includes applying a predicted future value of a first attribute of the first one or more attributes as an input to at least one of the one or more first principle models.

15. The one or more non-transitory, computer-readable media of claim 14, wherein the first attribute is viable cell density.

16. The one or more non-transitory, computer-readable media of claim 11, wherein the one or more data-driven models include a linear regression model or a probabilistic regression model.

17. The one or more non-transitory, computer-readable media of claim 16, wherein the one or more data-driven models include a Gaussian process regression model.

18. The one or more non-transitory, computer-readable media of claim 11, wherein the one or more data-driven models include a feed-forward neural network.

19. The one or more non-transitory, computer-readable media of claim 11, wherein predicting the future values of the cell culture attributes is based on (i) the current values of the cell culture attributes and (ii) one or more earlier values of the cell culture attributes.

20. The one or more non-transitory, computer-readable media of claim 11, wherein using the one or more first principle models to predict the future values of the first attribute includes applying one or more previous control values as inputs to the one or more first principle models.

21. A system comprising:

a bioreactor configured to hold a cell culture during a cell culture process;

an electronically-controllable input device configured to provide physical input to the cell culture process;

one or more analytical instruments configured to measure one or more cell culture attributes associated with the cell culture; and a computing system configured to, for one or more time intervals during the cell culture process, obtain, based on measurements by the one more analytical instruments, current values of cell culture attributes associated with the cell culture, generate a control value for the physical input to the cell culture process, wherein generating the control value includes predicting, based on the current values, future values of the cell culture attributes, at least by (i) using one or more data-driven models to predict future values of a first one or more attributes of the cell culture attributes, and (ii) using one or more first principle models to predict future values of a second one or more attributes of the cell culture attributes, and determining the control value by optimizing an function equation subject to the predicted future values of the cell culture attributes, and control the physical input to the cell culture process using the control value, by sending a control signal to the electronically-controllable input device.

22. The system of claim 21, wherein:

the electronically-controllable input device includes a glucose pump;

the physical input to the cell culture process is a glucose feed rate; and the second one or more attributes include a glucose concentration of the cell culture.

* * * * *